United States Patent
Tabata et al.

(10) Patent No.: US 9,243,272 B2
(45) Date of Patent: Jan. 26, 2016

(54) ENZYME PREPARATION CONTAINING THERMOSTABLE DNA POLYMERASE, METHOD FOR PRODUCING SAME, AND METHOD FOR DETECTING SUBJECT ORGANISM TO BE DETECTED

(75) Inventors: Homare Tabata, Takigawa (JP); Hiroshi Minami, Sunagawa (JP); Hideki Niimi, Toyama (JP); Isao Kitajima, Toyama (JP); Tomohiro Ueno, Isui (JP); Shiroh Hayashi, Toyama (JP); Masashi Mori, Ishikawa-gun (JP)

(73) Assignees: HOKKAIDO MITSUI CHEMICALS INC., Hokkaido (JP); NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 1141 days.

(21) Appl. No.: 13/144,175

(22) PCT Filed: Jan. 15, 2010

(86) PCT No.: PCT/JP2010/050443
§ 371 (c)(1),
(2), (4) Date: Jul. 12, 2011

(87) PCT Pub. No.: WO2010/082640
PCT Pub. Date: Jul. 22, 2010

(65) Prior Publication Data
US 2012/0094296 A1 Apr. 19, 2012

(30) Foreign Application Priority Data

| Jan. 15, 2009 | (JP) | 2009-006556 |
| Feb. 4, 2009 | (JP) | 2009-023707 |
| Feb. 23, 2009 | (JP) | 2009-040052 |
| Aug. 4, 2009 | (JP) | 2009-181755 |

(51) Int. Cl.
*C12Q 1/68* (2006.01)
*C12P 19/34* (2006.01)
*C12N 9/12* (2006.01)

(52) U.S. Cl.
CPC .............. *C12P 19/34* (2013.01); *C12N 9/1252* (2013.01); *C12Q 1/68* (2013.01)

(58) Field of Classification Search
CPC .................................. C12Q 1/68; C12P 19/34
USPC .................................................. 435/6.1, 91.2
See application file for complete search history.

(56) References Cited

U.S. PATENT DOCUMENTS

| 5,314,809 A | 5/1994 | Erlich et al. | |
| 5,753,482 A * | 5/1998 | Ishino et al. | 435/194 |
| 6,054,301 A | 4/2000 | Kitabayashi et al. | |
| 6,444,424 B1 * | 9/2002 | Chatterjee et al. | 435/6.12 |
| 2002/0082234 A1 * | 6/2002 | Black et al. | 514/44 |
| 2003/0175769 A1 | 9/2003 | Heindl et al. | |
| 2009/0061446 A1 | 3/2009 | Niimi et al. | |

FOREIGN PATENT DOCUMENTS

| EP | 0 745 675 A2 | 12/1996 |
| EP | 1 350 841 A2 | 10/2003 |
| EP | 1 997 886 A1 | 12/2008 |
| JP | 05-292968 A | 11/1993 |
| JP | 06-090799 A | 4/1994 |
| JP | 08-322597 A | 12/1996 |
| JP | 2002-291490 A | 10/2002 |
| JP | 2003-259882 A | 9/2003 |
| JP | 2006-180886 A | 7/2006 |
| JP | 2006-254784 A | 9/2006 |
| WO | WO 2007/097323 A1 | 8/2007 |

OTHER PUBLICATIONS

Extended European Search Report dated Nov. 28, 2012, issued by the European Patent Office in the corresponding European Application No. 10731309.0. (10 pages).

Klaschik, et al., "Comparison of Different Decontamination Methods for Reagents to Detect Low Concentrations of Bacterial 16S DNA by Real-Time-PCR", Molecular Biotechnology, 2002, vol. 22, No. 3, pp. 231-242.

Niimi, et al., "A Novel Eukaryote-Made Thermostable DNA Polymerase which is Free from Bacterial DNA Contamination", Journal of Clinical Microbiology, Jul. 20, 2011, vol. 49, No. 9, pp. 3316-3320.

International Search Report (PCT/ISA/210) issued on Apr. 13, 2010, by Japanese Patent Office as the International Searching Authority for International Application No. PCT/JP2010/050443.

Written Opinion (PCT/ISA/237) issued on Apr. 13, 2010, by Japanese Patent Office as the International Searching Authority for International Application No. PCT/JP2010/050443.

H. Niimi et al., "Real-time PCR-ho o Mochiita Jinsoku na Haiketsusho Kiinkin Dotei System no Kochiku ni Kansuru Kenkyu", Japanese Journal of Clinical Laboratory Automation, 2007, p. 745, vol. 32, No. 4 (in Japanese).

N. Jothikumar et al., "Real-Time Multiplex SYBR Green I-Based PCR Assay for Simultaneous Detection of *Salmonella serovars* and *Listeria monocytogenes*", Journal of Food Protection, 2003, pp. 2141-2145, vol. 66, No. 11.

M. Mori, "Real-time PCR kit for sepsis", Journal of Analytical Bio-Science, 2005, pp. 400-404, vol. 28, No. 5.

European Search Report dated May 23, 2014, issued in EP 10 731 309.0 (7 Pages).

Mroczkowski et al., *Secretion of Thermostable DNA Polymerase Using a Novel Baculovirus Vector*, 269(18) The Journal of Biological Chemistry 13522-13528 (May 6, 1994).

* cited by examiner

*Primary Examiner* — Ardin Marschel
(74) *Attorney, Agent, or Firm* — Buchanan, Ingersoll & Rooney PC

(57) ABSTRACT

Disclosed is a thermostable DNA polymerase preparation which can illimitably reduce the risk of false positivity in the detection of a subject microorganism utilizing a gene amplification reaction and therefore enables the selective amplification of DNA for detecting the subject microorganism even when the amount of the subject microorganism is small and therefore the amount of DNA collected therefrom is extremely small, and can be produced at a reduced cost. Also disclosed is a method for quantifying or quantifying/identifying a subject organism to be detected rapidly, conveniently and with high sensitivity using the preparation of the present invention.

15 Claims, 23 Drawing Sheets

| Host | n.d. | | | n.d. | | | S.Cerevisiae | | |
|---|---|---|---|---|---|---|---|---|---|
| DNA Polymerase | TaKaRa TaKaRa Taq | | | ABI AmpliTaq Gold LD | | | Taq DNA Polymerase | | |
| E.Coli DNA | - | - | ○ | - | - | ○ | - | - | ○ |
| PCR cycle | 40 | 60 | 30 | 40 | 60 | 30 | 40 | 60 | 30 |
| Lane | 1 | 2 | 3 | 4 | 5 | 6 | 7 | 8 | 9 |

| Host | n.d. | | | n.d. | | | S.Cerevisiae | | |
|---|---|---|---|---|---|---|---|---|---|
| DNA Polymerase | TaKaRa TaKaRa Taq | | | ABI AmpliTaq Gold LD | | | Taq DNA Polymerase | | |
| E.Coli DNA | - | - | ○ | - | - | ○ | - | - | ○ |
| PCR cycle | 40 | 60 | 30 | 40 | 60 | 30 | 40 | 60 | 30 |
| Lane | 10 | 11 | 12 | 13 | 14 | 15 | 16 | 17 | 18 |

(A)

(B)

(A)

(B)

(B)

(A)

(C)

(A)

(B)

(A)

(B)

(A)

(B)

ENZYME PREPARATION CONTAINING THERMOSTABLE DNA POLYMERASE, METHOD FOR PRODUCING SAME, AND METHOD FOR DETECTING SUBJECT ORGANISM TO BE DETECTED

TECHNICAL FIELD

The present invention relates to an enzyme preparation containing a thermostable DNA polymerase, a method for producing the same, and a method for detecting a subject organism to be detected.

BACKGROUND ART

In recent years, a polymerase chain reaction (PCR) intended for detecting specific fungi, bacteria, viruses, or other organisms has enhanced its popularity in the medical, veterinary, food, and other fields because the analysis results can be known in a short period of time such as about 2 hours. However, a technology for detecting unspecified fungi, bacteria, viruses or other organisms in a short period of time has yet been established.

Very great merits are expectable when a trace of an unspecific organism can be detected, identified, and quantified from a place which should be in a sterile environment in nature. For example, blood, cerebrospinal fluid, amniotic fluid, urea, or the like can be used as a sample for analysis to early detect and identify the infection of humans or domestic animals, leading to the administration of an effective antibiotic at an early stage. In addition, the state of recovery can be monitored using the quantitative value of infecting bacteria. Great merits in the field of quality control of daily life water, foods, cosmetics, and the like can also be expected. For example, the presence of undesired, unspecified bacteria, fungi, viruses or other organisms can be quickly detected and identified in daily life water which persons have a possibility of inhaling (drinking) in life. Such water includes, tap water, water from a water tank, air-conditioning circulating water, water from a humidifier, hot spring water, and swimming pool water, foods, and cosmetics. In addition, the presence level can be monitored with high sensitivity. Thus, it is assumed that establishment of a method for simply and rapidly quantifying or identifying a subject microorganism to be detected in a sample with high sensitivity renders the rippling field of the technology very wide; thus, there is strong need therefore.

Sepsis is a serious systemic infection and in whose definite diagnosis the detection/identification of a causative microorganism in the blood is mandatory. The number of patients having sepsis has recently increased with the sophistication of medical treatment such as cancer treatment or organ transplantation. In view of in-hospital infections, multidrug-resistant bacteria including methicillin-resistant *Staphylococcus aureus* (MRSA) often constitutes a causative bacterium of sepsis; thus, to select a suitable antibiotic for the life saving of patients, it is clinically important to detect and identify a causative microorganism in the blood as rapidly as possible.

Intrauterine infection, which is the most common cause of premature birth, is a serious infection fatal to fetuses; thus, it will be important for the life saving of fetuses to detect and identify a causative microorganism thereof in the amniotic fluid as rapidly as possible, and to administer the most suitable antibiotic at an early stage of the occurrence thereof. Similarly, in the veterinary field, bovine mammitis is a very serious disease for milk cows, for example; when the treatment thereof is delayed, there is often no means other than removal, also leading to industrial problems.

However, culture methods using culture bottles and selective media are typically used in current detection methods for infecting microorganisms. They take at least several days to obtain the results thereof. Thus, clinically, at present, empiric therapy is forced to be carried out until the results are revealed. As a result, an antibiotic is forced to be blindly selected, which represents a major disadvantage, while the detection is required to be rapid. Some microorganisms may have antibiotic resistance genes. Therefore, a drug susceptibility test is often performed in parallel; however, it takes several days to produce results as with the detection method for identification. As a result, the appearance of multidrug-resistant bacteria due to the use of broad-spectrum antibiotics and the inappropriate choice of antibiotics cause a situation, for example, that patients with sepsis and fetuses with intrauterine infection cannot be saved; and that milk cows with mastitis are forced to be removed. In addition, the detection of heterotrophic bacteria has a high risk of producing false-negative results because it needs special culture conditions.

Against such a background, the detection of unidentified bacteria has been studied using PCR: an attempt has been made to detect and identify a causative microorganism of sepsis by amplifying a trace of DNA of the causative microorganism by PCR; and hybridizing the amplified causative microorganism DNA to a strain-specific nucleotide probe targeted at an empirically assumed microorganism (JP06-90799A). In addition, the development of an detection technique for sepsis using real-time PCR employing hybridization probes as a basic principle has been studied for more rapid detection/identification of a causative microorganism (Journal of Analytical Bio-Science, Vol. 28, No. 5 (2005) 400-404). A rapid detection/identification method for a causative microorganism has been studied by performing gene amplification by PCR using microorganism DNA as a template and a specific primer set, and then analyzing the combination of melting temperatures (Tm values) of the resultant products, specific for microorganisms or the difference between the Tm values (WO2007/097323). However, accuracy must also be ensured in the results obtained in a short period of time using PCR. Thus, for PCR, it can also be said to be important to make sensitivity compatible with specificity. These prior techniques apply gene amplification techniques using PCR, but they are methods limited to assumed target microorganisms. Thus, they cannot detect microorganisms when outside the scope of the assumption. Even when they are used as detection/identification methods for unidentified microorganisms, a technique for quantifying them has not been established and has been impossible.

Real-time PCR is a sole method through which a curve of amplification with time can be displayed. Therefore, today, it provides a crucial detection technique for the quantitative determination of gene expression. Particularly, detection methods using intercalators such as SYBR Green are world-widely and frequently used, because they have low cost and are simple and convenient. However, the real-time PCR using an intercalator detects not only a target but also non-specific amplification products, posing a problem that the detection sensitivity thereof is decreased. A particularly problematical non-specific amplification product thus formed is a primer dimer. To suppress the formation of a primer dimer, various means are proposed by devising design of primers, using the Hot Start method, an amplification method using modified primers (JP2002-291490A), a Hot Start PCR using an improved reagent for PCR (JP2003-259882A), and a method involving adding a substance binding to the primer dimer to a sample (JP2006-254784A). However, it is extremely difficult to completely inhibit the formation of non-specific amplification products including a primer dimer. Even when various methods for suppressing the formation of the primer dimer are used, non-specific amplification products are detected depending on the increased number of PCR cycles, which is the major factor for the decreased sensitivity in the quantitative measurement using the real-time PCR. Even in qualitative detection, the Tm (melting temperature) value must be checked in each measurement to exclude "false-positive" due to the primer dimer, for example, which has become a major problem for the real-time PCR measurement system.

To provide a DNA polymerase used for PCR, a method for producing a DNA polymerase preparation using a genetic recombination technology has been studied (JP2006-180886A). Among commercial thermostable DNA polymerase preparations commonly used for PCR reaction, high purity preparations are also commercially available; however, even in the PCR reaction using each of these high purity preparations, non-specific amplification products of unknown origin are detected, for example, when the gene amplification reaction needs to be performed in conventional (about 30) cycles or more, which has limited the use thereof.

Various techniques have been developed to secure high specificity in the PCR method. The simplest method is a nested PCR method, which, however, needs the labor and time of performing PCR two times. Accordingly, a "nested amplification method" which involves carrying out nested PCR by a single PCR process (JP05-292968A) is proposed. This method is an excellent method in which nested PCR can be performed using only a single thermal cycling profile; however, it has not yet been put to practical use possibly due to the absence of technique by which the Tm values of primers and an amplification product could be easily measured at the time of the application. This method can be put to practical use at present that a real-time PCR technique is available. Other methods such as a method using Hybri-Probe and a TaqMan PCR method are generally used; however, the preparation of probes used for these methods is not easy for everyone and the cost for the preparation thereof is also expensive. Therefore, at present, there not yet exists such a method satisfying all of rapidity, simplicity, and economical efficiency, has been not provided yet.

As described above, when simply amplifying DNA from a trace of a sample microorganism and analyzing, in particular, performing the quantification or identification analysis of the DNA in a short time can be carried out, the analysis of even a trace level of a gene previously incapable of being analyzed can be achieved. In addition, rapid and accurate determination in the fields of medicine, veterinary, and analysis of various samples such as daily life water and foods can be carried out. Meanwhile, however, in PCR for the amplification of a trace of sample microorganism DNA, the control of both sensitivity and specificity to high degrees has not yet been achieved and rapid quantification or quantification/identification for unidentified microorganisms has also not yet been achieved.

SUMMARY OF INVENTION

Technical Problem

An object of the present invention is to provide a thermostable DNA polymerase preparation best suited to the amplification of a trace of sample microorganism DNA using a PCR method and to provide an analysis method suitable for the initial analysis of a trace of a sample microorganism using the DNA polymerase preparation.

Solution of Problem

The present specification includes the following inventions.

(I) A thermostable DNA polymerase preparation, wherein:
(1) the thermostable DNA polymerase has contamination with 10 fg or less of bacterially-derived nucleic acid other than the gene encoding the thermostable DNA polymerase based on 1 unit of the DNA polymerase, and
(2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

(II) A production method for a thermostable DNA polymerase preparation, comprising:
(1) transforming eukaryotic cells with a gene encoding the thermostable DNA polymerase to provide thermostable DNA polymerase gene-expressing transformant cells;
(2) culturing the transformant cells; and
(3) obtaining an extract containing the thermostable DNA polymerase from the cultured transformant cells, followed by subjecting the extract to heat treatment; or
subjecting the cultured transformant cells to heat treatment, followed by obtaining an extract containing the thermostable DNA polymerase from the heat-treated transformant cells.

(III) A detection method for a subject organism to be detected in a sample, comprising:
(1) an amplification step of performing a nucleic acid amplification reaction using nucleic acid prepared from the sample, primers for amplifying an intended gene specific for the subject organism to be detected, and a thermostable DNA polymerase preparation; and
(2) a detection step of detecting an amplification product of the intended gene in amplification products in the amplification step,
wherein the thermostable DNA polymerase preparation is any one of:
(A) a thermostable DNA polymerase preparation produced using eukaryotic cells as a host; and
(B) a thermostable DNA polymerase preparation, wherein:
(B-1) the thermostable DNA polymerase has contamination with 10 fg or less of bacterially-derived nucleic acid other than the gene encoding the thermostable DNA polymerase based on 1 unit of the DNA polymerase, and
(B-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

(IV) A quantification/identification method for a subject organism to be detected in a sample, comprising:
(1) a first amplification step of performing a nucleic acid amplification reaction using nucleic acid prepared from the sample, primers (B) and (M), for amplifying an intended gene specific for the subject organism to be detected, and a thermostable DNA polymerase preparation,
(2) a first quantification/identification step of analyzing a combination of melting temperatures (Tm values) of a plurality of amplification products (3 to 10 products) in the first amplification step based on a combination of melting temperatures (Tm values) specific for amplification products of the intended gene to perform the quantification/identification of the subject organism to be detected in the sample, (3) a second amplification step of performing a nucleic acid amplification reaction using nucleic acid prepared from the sample, primers (F), for amplifying an intended gene specific for the subject organism to be detected, and a thermostable DNA polymerase preparation produced using a bacterium as a host, and (4) a second quantification/identification step of analyzing a combination of melting temperatures (Tm values) of a plurality of amplification products (3 to 10 products) in the second amplification step based on a combination of melting temperatures (Tm values) specific for an amplification product of the intended gene to quantify the amplification products in the first quantification/identification step of quantifying/identifying the subject organism to be detected and the second amplification step to perform the quantification/identification of the subject organism to be detected in the sample from the quantification results obtained, wherein the primers (B), (F), and (M) are:

(B) a primer set capable of amplifying a plurality of regions of the 16S rRNA genes of all bacteria and primers containing all or ⅓ or more of each of the base sequences of the above primers, (F) a primer set capable of amplifying a plurality of regions of the 18S rRNA gene of all fungi, wherein each primer comprising entire, or ⅓ or more of each of the base sequences thereof, and (M) a primer set specifically amplifying an antibiotic resistance gene reflecting a spread epidemic of the current time such as a mec A gene exhibiting methicillin resistance wherein the thermostable DNA polymerase preparation in the first amplification step is any one of:

(A) a thermostable DNA polymerase preparation produced using eukaryotic cells as a host; and (B) a thermostable DNA polymerase preparation, wherein:

(B-1) the thermostable DNA polymerase has contamination with 10 fg or less of bacterially-derived nucleic acid other than the gene encoding the thermostable DNA polymerase based on 1 unit of the DNA polymerase, and (B-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

(V) A quantification/identification method for a subject organism to be detected in a sample, comprising:

(1) a first amplification step of performing a nucleic acid amplification reaction using nucleic acid prepared from the sample, primers (B) for amplifying an intended gene specific for the subject organism to be detected, and a thermostable DNA polymerase preparation, (2) a first quantification/identification step of analyzing a combination of melting temperatures (Tm values) of a plurality of amplification products (3 to 10 products) in the first amplification step based on a combination of melting temperatures (Tm values) specific for amplification products of the intended gene to perform the quantification/identification of the subject organism to be detected in the sample, (3) a second amplification step of performing a nucleic acid amplification reaction using nucleic acid prepared from the sample, primers (F), for amplifying an intended gene specific for the subject organism to be detected, and a thermostable DNA polymerase preparation produced using a bacterium as a host, (4) a second quantification/identification step of analyzing a combination of melting temperatures (Tm values) of a plurality of amplification products (3 to 10 products) in the second amplification step based on a combination of melting temperatures (Tm values) specific for amplification products of the intended gene to quantify the amplification products in the first quantification/identification step of quantifying/identifying the subject organism to be detected and the second amplification step to perform the quantification/identification of the subject organism to be detected in the sample from the quantification results obtained, (5) a third amplification step of performing a nucleic acid amplification reaction using nucleic acid prepared from the sample, primers (M) for amplifying an intended gene specific for the subject organism to be detected, and a thermostable DNA polymerase preparation, and (6) a third quantification/identification step of analyzing melting temperatures (Tm values) of amplification products in the third amplification step based on melting temperatures (Tm values) specific for amplification products of the intended gene to perform the quantification/identification of the subject organism to be detected in the sample, wherein the primers (B), (F) and (M) are:

(B) a primer set capable of amplifying a plurality of regions of the 16S rRNA genes of all bacteria wherein each primer comprising entire, or ⅓ or more of each of the base sequences thereof, (F) a primer set capable of amplifying a plurality of regions of the 18S rRNA gene of all fungi, wherein each primer comprising entire, or ⅓ or more of each of the base sequences thereof, and (M) a primer set specifically amplifying an antibiotic resistance gene reflecting a spread epidemic of the current time such as a mec A gene exhibiting methicillin resistance, wherein the thermostable DNA polymerase preparations in the first and third amplification steps are:

(A) a thermostable DNA polymerase preparation produced using eukaryotic cells as a host; and (B) a thermostable DNA polymerase preparation, wherein:

(B-1) the thermostable DNA polymerase has contamination with 10 fg or less of bacterially-derived nucleic acid other than the gene encoding the thermostable DNA polymerase based on 1 unit of the DNA polymerase, and (B-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

(VI) A set for quantifying and/or identifying a subject organism to be detected contained in a sample, comprising a thermostable DNA polymerase preparation for amplifying nucleic acid prepared from the sample and primers for amplifying an intended gene specific for the subject organism to be detected, wherein the thermostable DNA polymerase preparations are:

(A) a thermostable DNA polymerase preparation produced using eukaryotic cells as a host; and (B) a thermostable DNA polymerase preparation, wherein:

(B-1) the thermostable DNA polymerase has contamination with 10 fg or less of bacterially-derived nucleic acid other than the gene encoding the thermostable DNA polymerase based on 1 unit of the DNA polymerase, and (B-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

(VII) A set for quantifying and/or identifying a subject organism to be detected contained in a sample, comprising: any one of (A) a thermostable DNA polymerase preparation produced using eukaryotic cells as a host; and (B) a thermostable DNA polymerase preparation, wherein:

(B-1) the thermostable DNA polymerase has contamination with 10 fg or less of bacterially-derived nucleic acid other than the gene encoding the thermostable DNA polymerase based on 1 unit of the DNA polymerase, and (B-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase for amplifying nucleic acid prepared from the sample, a thermostable DNA polymerase preparation for amplifying nucleic acid prepared from the sample, produced using bacterial cells as a host, and primers for amplifying an intended gene specific for the subject organism to be detected.

(VIII) A system for quantifying and/or identifying a subject organism to be detected contained in a sample, comprising:

(1) an amplifier for performing a nucleic acid amplification reaction using nucleic acid prepared from the sample, primers for amplifying an intended gene specific for the subject organism to be detected, and a thermostable DNA polymerase, (2) a quantification device for quantifying the amplified product in the amplification step, (3) a computer for calculating the amount of the subject organism to be detected in the sample from the quantification results of the amplification product of the intended gene, and (4) a data base for calculating the amount of the subject organism to be detected in the sample from the quantification results of the amplification product of the intended gene, wherein the system is for performing the detection method or the quantification/identification method.

Advantageous Effects of Invention

Regarding the detection of the sample microorganism using a gene amplification reaction, a thermostable DNA polymerase preparation can be provided according to the present invention. The thermostable DNA polymerase preparation according to the present invention not only enables the selective amplification of DNA for detecting a sample microorganism even when the amount of the sample microorganism is limited and the amount of DNA collected therefrom is extremely small, but also permits the reduction of production cost.

In addition to the thermostable DNA polymerase preparation, use of a masked Primer Dimer method enables quantitative detection without reducing sensitivity and eliminates the risk of false positivity due to a primer dimer in qualitative detection, because the formation of the primer dimer no longer becomes a hindrance for the real-time PCR method using an intercalator. Thus, it makes quantification accurate to the detection sensitivity limit (sensitive quantification procedure) possible. In addition, this method is simple and economical compared to conventional methods such as a Hot Start method using an anti-Taq antibody.

In addition, highly specific nested PCR typically requiring two rounds of PCR can be rapidly performed in only one round (one step), by applying a "nested amplification method" (JP05-292968A) or devising the extension time for PCR. The design of primers is simple and economical compared to that for the Hybri Probe method, the TaqMan method, or the like.

In addition to the thermostable DNA polymerase preparation of the present invention, the masked Primer Dimer method and the one-step nested PCR method can be used in combination to perform highly sensitive, highly specific PCR rapidly and simply.

According to the present invention, a method can rapidly be provided for simply quantifying or identifying a subject organism to be detected with high sensitivity by genetic examination. This method also enables the rapid, simple and highly sensitive quantification of a subject organism to be detected for any sample which should be in a sterile environment or in which contamination with a trace of the subject organism to be detected is a problem. In addition, this quantification or quantification/identification method enables the monitoring of a state in which the number of bacteria is controlled or changed in the body of a patient, for the maintenance of a sterile condition or the number of bacteria, confirmation of a therapeutic effect based on a change in the amount of infecting bacteria, or the like. The combination of the culturing of a sample and the highly sensitive quantification method of the present invention enables drug susceptibility testing to be performed rapidly.

BRIEF DESCRIPTION OF DRAWINGS

FIG. 1 is a diagram related to a genealogical tree analysis carried out based on the gene sequences of bacterial 16s rRNA and eukaryotic cell 18s rRNA.

FIG. 2 is an SDS-PAGE photograph after heat-treatment.

FIG. 3 shows a detection limit of PCR using a thermostable DNA polymerase preparation using *Escherichia coli* DNA as a template.

FIG. 4 shows results of verification of contamination of non-specific nucleic acid using a thermostable DNA polymerase preparation.

FIG. 5(A) is a graph showing an amplification curve analysis of the real-time PCR using AmpliTaq Gold LD; and FIG. 5(B) is a graph showing an amplification curve analysis of the real-time PCR using a thermostable DNA polymerase preparation produced by using *S. cerevisiae* as a host.

FIG. 6(A) is a graph showing a melting curve analysis of the real-time PCR using AmpliTaq Gold LD; and FIG. 6(B) is a graph showing a melting curve analysis of the real-time PCR using a thermostable DNA polymerase preparation produced by using *S. cerevisiae* as a host.

FIG. 7 shows results of verification of contamination of non-specific nucleic acid using a thermostable DNA polymerase preparation produced by using *A. oryzae* as a host.

FIG. 8 is a graph showing an amplification curve analysis of the real-time PCR using a masked Primer Dimer method. FIG. 8(A) shows an analysis using a *T. aquaticus*-derived thermostable DNA polymerase preparation produced by using *S. cerevisiae* as a host, FIG. 8(B) shows an analysis using a mutant *P. furiosus*-derived thermostable DNA polymerase preparation produced by using *S. cerevisiae* as a host, FIG. 8(C) shows an analysis using a mutant *T. gorgonarius*-derived thermostable DNA polymerase preparation produced by using *S. cerevisiae* as a host, FIG. 8(D) shows an analysis using a *T. aquaticus*-derived thermostable DNA polymerase preparation produced by using *P. pastoris* as a host, and FIG. 8(E) shows an analysis using a *T. aquaticus*-derived thermostable DNA polymerase preparation produced by using Tobacco BY-2 as a host.

FIG. 9 is a graph showing a melting curve analysis of the real-time PCR. FIG. 9(A) shows an analysis using a *T. aquaticus*-derived thermostable DNA polymerase preparation produced by using *S. cerevisiae* as a host, FIG. 9(B) shows an analysis using a mutant *P. furiosus*-derived thermostable DNA polymerase preparation produced by using *S. cerevisiae* as a host, FIG. 9(C) shows an analysis using a mutant *T. gorgonarius*-derived thermostable DNA polymerase preparation produced by using *S. cerevisiae* as a host, FIG. 9(D) shows an analysis using a *T. aquaticus*-derived thermostable DNA polymerase preparation produced by using *P. pastoris* as a host, and FIG. 9(E) shows an analysis using a *T. aquaticus*-derived thermostable DNA polymerase preparation produced by using Tobacco BY-2 as a host.

FIG. 10(A) is a graph showing a conventional PCR condition setting and a fluorescence detection point, and FIG. 10(B) is a graph showing a fluorescence detection point in a masked Primer Dimer method.

FIG. 11(A) shows arrangement of primers and amplification products in a One Step semi-nested PCR method. FIG. 11(B) shows arrangement of primers and amplification products in One Step nested PCR. FIG. 11(C) shows a plurality of Tm values (Bac1 to Bac5) obtained from bacteria and the relative values (d1 to d5) from the average of the Tm values.

FIG. 12 is a block diagram showing one example of a system for carrying out quantification and/or identification of a target organism to be detected in accordance with the present invention.

FIG. 13 is a graph showing an amplification curve analysis carried out in the program conditions described in Table 1. In this drawing, "A" shows an amplification curve of *E. coli*, and "B" shows an amplification curve of distilled water (D.W.).

FIG. 14 is a graph showing a melting curve analysis carried out in the program conditions described in Table 1. In this drawing, "A" shows a melting curve of *E. coli*, and "B" shows a melting curve of a primer dimer.

FIG. 15(A) is a graph showing an amplification curve of results of the real-time PCR in the program conditions described in Table 2. In this drawing, "A" shows an amplification curve of *E. coli*, and "B" shows an amplification curve of distilled water (D.W.). FIG. 15(B) is a graph showing the result of an examination of infectious bacteria/fungi using a DNA extraction solution of each test sample as a template. In this drawing, "A" is an amplification curve of *C. albicans* as a positive control, "B" is an amplification curve of distilled water (D.W.), tap water, spring water, hot spring water, and air-conditioning water. FIG. 15(C) is a graph showing the result of measurement of infectious bacteria using a DNA extraction solution of each test sample as a template. In this drawing, "A" is an amplification curve of *E. coli* (number of cycles: 14.47) as a positive control, "B" is an amplification curve of hot spring water (number of cycles: 30.54), "C" is an amplification curve of air-conditioning water (number of cycles: 28.96), and D is an amplification curve of amplification curve of distilled water (D.W.), tap water, and spring water, respectively.

FIG. 16 is a graph showing a result of examination of infectious fungi when a cream puff is used as a sample. FIG. 16(A) is a proliferation curve when a fresh cream puff is used. In this drawing, "A" is a proliferation curve of *C. albicans* as a positive control (number of cycles: 23.78), and "B" is a proliferation curve of distilled water (D.W.) and a cream puff (cream) (number of cycles: 45.71). FIG. 16(B) is a proliferation curve when an old cream puff is used. In this drawing, "A" is a proliferation curve of *C. albicans* as a positive control (number of cycles: 23.78), and "B" is a proliferation curve of distilled water (D.W.) and a cream puff (cream) (number of cycles: 44.37).

FIG. 17 is a graph showing a result of examination of infectious bacteria when a cream puff is used as a sample. FIG. 17(A) is a proliferation curve when a fresh cream puff is used. In this drawing, "A" is a proliferation curve of *E. coli* as a positive control (number of cycles: 26.55), and "B" is a proliferation curve of distilled water (D.W.) and a cream puff (cream). FIG. 17(B) is a proliferation curve when an old cream puff is used. In this drawing, "A" is a proliferation curve of *E. coli* as a positive control (number of cycles: 23.78), "B" is a proliferation curve of a cream puff (cream) (number of cycles: 24.48), and "C" is a proliferation curve of distilled water (D.W.).

FIG. 18 is a graph showing a result of examination using a blood sample of septicemia patient A with by *C. albicans*. FIG. 18(A) is a proliferation curve of a fungal universal primer. In this drawing, A is a proliferation curve of *C. albicans* as a positive control (number of cycles: 27.51), B is a proliferation curve of a blood sample (patient A: number of cycles: 33.70), and C is a proliferation curve of distilled water (D.W.). FIG. 18(B) is a proliferation curve of a bacterial universal primer. In this drawing, "A" is a proliferation curve of *E. coli* as a positive control (number of cycles: 33.70), and "B" is a proliferation curve of a blood test sample (patient A) and distilled water (D.W.).

FIG. 19 is a graph showing a result of examination using a blood sample of septicemia patient B by *Bacillus* species. FIG. 19(A) is a proliferation curve of a fungal universal primer. In this drawing, "A" is a proliferation curve of *C. albicans* as a positive control, and "B" is a proliferation curve of a blood sample (patient B) and distilled water (D.W.). FIG. 19(B) is a proliferation curve of a bacterial universal primer with respect to a blood sample. In this drawing, "A" is a proliferation curve of *E. coli* as a positive control (number of cycles: 22.53), "B" is a proliferation curve of a blood sample (patient B: number of cycles: 34.07), and "C" is a proliferation curve of a distilled water (D.W.). FIG. 19(C) shows a proliferation curve of a bacterial universal primer with respect to a blood culture test sample. In this drawing, "A" is a proliferation curve of a blood culture test sample (patient B: number of cycles: 14.47), "B" is a proliferation curve of *E. coli* as a positive control (number of cycles: 25.64), and "C" is a proliferation curve of a distilled water (D.W.).

FIG. 20 shows a result of the real-time PCR using DNA of MRSA as a template, and using a primer specific to MRSA. "A" is a proliferation curve with a Spa primer, "B" is a proliferation curve with a mecA primer, "C" is a proliferation curve with a bacterial universal primer, and "D" is a proliferation curve with a fungal universal primer.

FIG. 21(A) is a graph showing measurement of drug sensitivity of detected *Staphylococcus epidermidis* with respect to gentamicin (GM) and erythromycin (EM) from the enrichment amount overtime. FIG. 21(B) is a graph showing measurement of drug sensitivity of *Bacillus cereus* with respect to cefazolin (CZ), ampicillin (AP), and erythromycin (EM) from the enrichment rate overtime.

Figure 22:
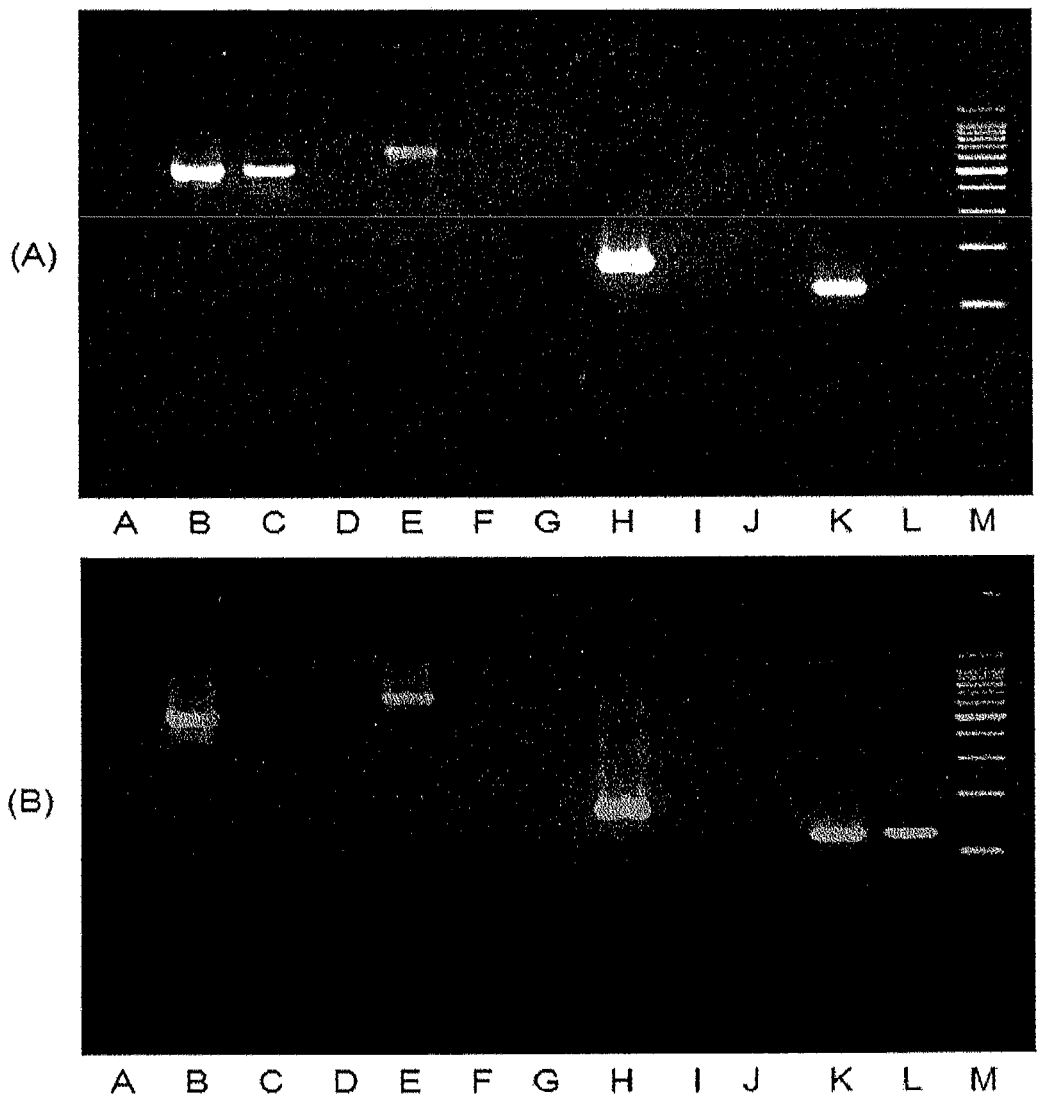
[FIG. 22]

FIG. 22(A) shows the result of the measurement of infectious bacteria/fungi in an amniotic fluid sample No. 1 with intrauterine infection, and FIG. 22 (B) shows the result of the measurement of infectious bacteria/fungi in an amniotic fluid sample No. 2 with threatened premature delivery. "A" to "C" are results of detection attempted by using bacterial universal primers, and "A": distilled water, "B": *E. coli* as a positive control, and "C": amniotic fluid sample are shown. "D" to "F" are results of detection attempted by using fungal universal primers, and "D": distilled water, "E": *C. albicans* as a positive control, and "F": amniotic fluid sample are shown. "G" to "H" are results of detection attempted by using a primer specific to the genus *Mycoplasma*, and "G": distilled water, "H": *Mycoplasma* positive control, "I": amniotic fluid sample are shown. "J" to "L" are results of detection attempted by using a primer specific to the genus *Ureaplasma*, and "J": distilled water, "K": *Ureaplasma* positive control, and "L": amniotic fluid sample are shown.

Figure 23:
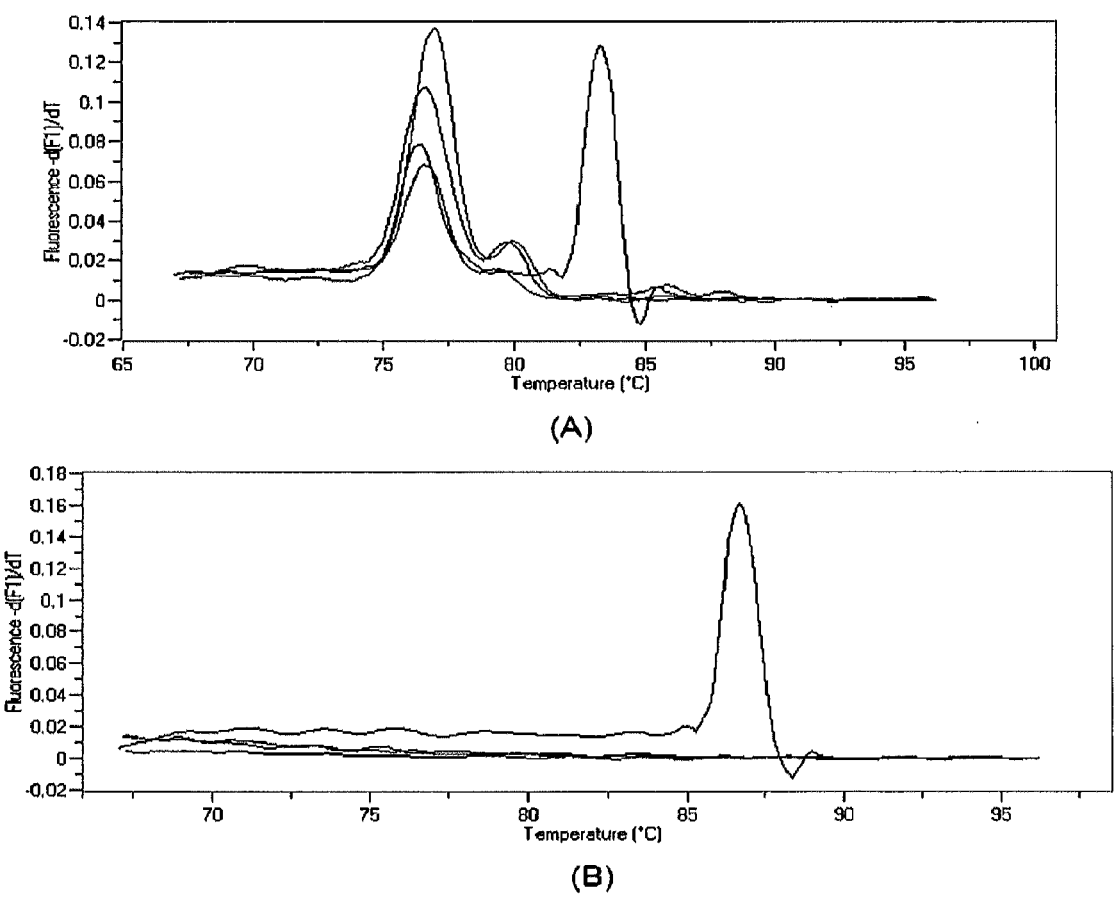

[FIG. 23] FIG. 23 shows a confirmation of whether or not nested PCR is well carried out by using a Tm value of an amplification product by mixing three primers including a semi-nested primer. FIG. 23 (A) shows that only an outer amplification product I (Tm value: 87° C.) is amplified when only the Amplification 1 in Tables 3 and 4 is carried out. FIG. 23 (B) shows that only an inner nested amplification product II (Tm value: 83° C.) (others are primer dimers) is amplified when only the Amplification 2 in Tables 3 and 4 is carried out.

Figure 24:
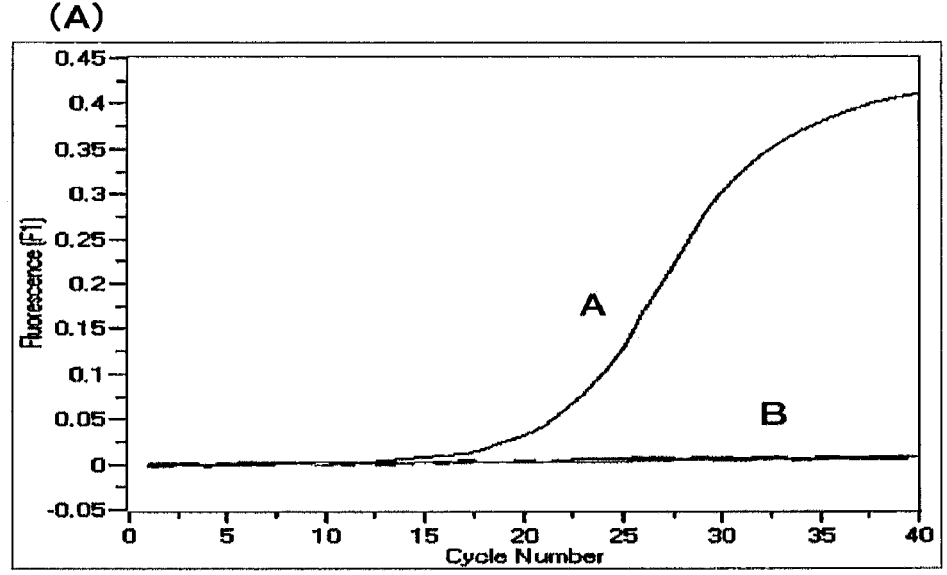
Figure 24:
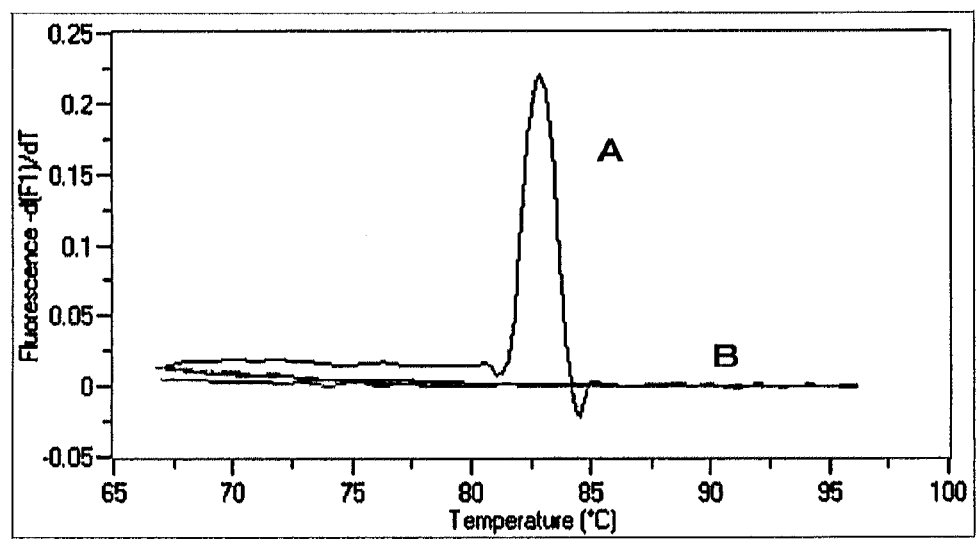

[FIG. 24] FIG. 24 shows confirmation that highly sensitive and highly specific PCR is well carried out by mixing a highly sensitive detection method using e-DNAP, a non-display method and a One Step nested PCR method by using an actual sample. FIG. 24(A) is a proliferation curve when a program of Table 3 or Table 4 is carried out with a primer specific to *E. coli*. In this drawing, "A" is a proliferation curve of *E. coli*, and "B" is a proliferation curve of distilled water (D.W.) and *S. aureus*, Human DNA. FIG. 24 (B) is a melting curve when a program of Table 3 or Table 4 is carried out with a primer specific to *E. coli*. "A" is a melting curve of *E. coli*, and "B" is a melting curve of distilled water (D.W.) and *S. aureus*, Human DNA. The amplification product in this drawing is only the inner nested amplification product II (Tm value: 83° C.), and other amplification products such as amplification products of distilled water (D.W.), *S. aureus*, and Human DNA are not observed.

Figure 25:
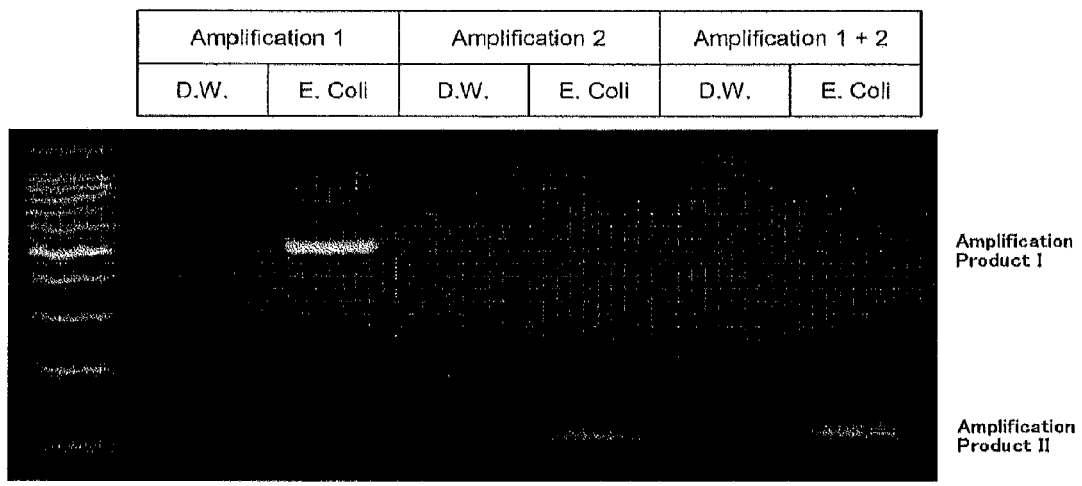

[FIG. 25] FIG. 25 shows confirmation whether or not nested PCR is well carried out from the size of an amplification product by mixing three primers including a semi-nested primer. When only Amplification 1 is carried out, only the outer amplification product I (548 bp) is amplified. When only Amplification 2 is carried out, only the inner nested amplification product II (110 bp) is amplified. When Amplifications 1+2 are carried out, only the inner nested amplification product II (110 bp) is amplified.

DESCRIPTION OF EMBODIMENTS (1) Thermostable DNA Polymerase Preparation

The present inventors produced a thermostable DNA polymerase utilizing genetic recombination using a bacterium as a host by the same manner for the commercial thermostable DNA polymerase preparation, and studied the application of the produced thermostable DNA polymerase preparation to PCR for detecting a target organism to be detected contained in a sample. However, regarding the detection of the subject microorganism to be detected using PCR even when the amount of the microorganism in a sample is small and the amount of DNA collected therefrom is extremely small, no thermostable DNA polymerase preparation could be provided by the conventional process, which could increases the number of PCR cycles and selectively amplify DNA for detecting a subject microorganism to be detected, and enabled the reduction of production cost.

Figure 1:
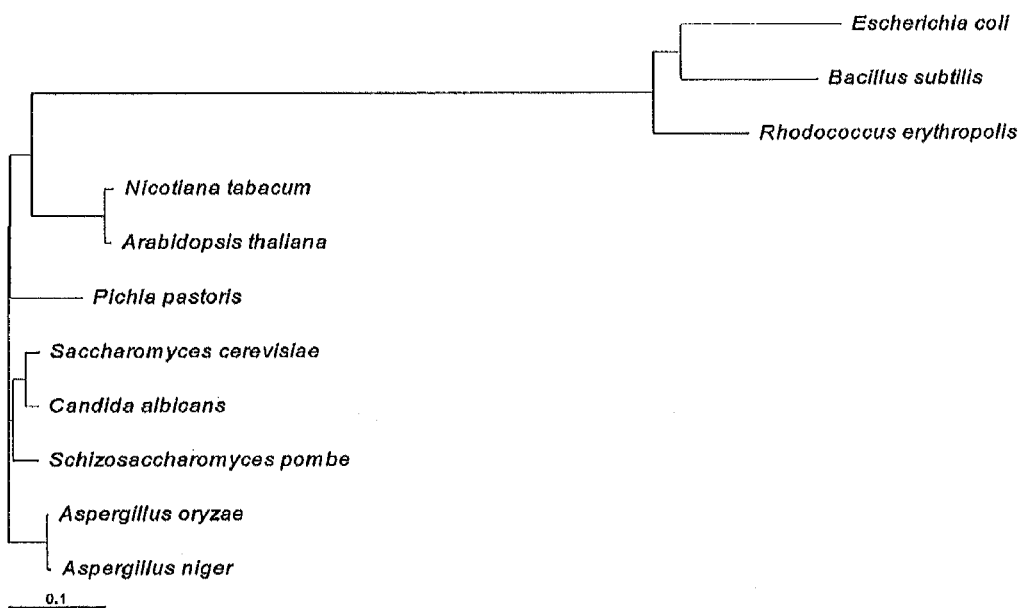
[FIG. 1]

Accordingly, considering the suitability of a host, the purification efficiency for a thermostable DNA polymerase, and the like, the present inventors have verified the distant relationship between organisms, referring to a phylogenetic tree (see Carl R. Woese, "Bacterial Evolution", Micro. Biol. Reviews, 51:221-271 (1987) and FIG. 1), and have focused attention on eukaryotic cells capable of being utilized as a host. As a result of studying the production of a thermostable DNA polymerase using eukaryotic cells as a host, it has been found that the majority of the thermostable DNA polymerase is produced as an insoluble matter in the culture extract precipitate thus obtained and irreversibly solubilized by subjecting the precipitate and the supernatant to heat treatment. This heating step can easily recover a thermostable DNA polymerase which is active and highly purified. In various studies, it has been found that the thermostable DNA polymerase preparation at least has the feature of causing no DNA amplification when a template is not added in the genetic width of bacterial 16S rRNA.

The present invention will be described below in detail.

The thermostable DNA polymerase preparation used in the present invention is a preparation containing a thermostable DNA polymerase and has at least one feature of the following requirements (A) and (B).

(A) A thermostable DNA polymerase preparation satisfying the following requirements (1) and (2):

(1) The thermostable DNA polymerase has contamination with 10 fg or less of bacterially-derived nucleic acid other than the gene encoding the thermostable DNA polymerase based on 1 unit of the DNA polymerase.

(2) No amplification products of the bacterially-derived nucleic acid are detected even when 32 cycles or more of gene amplification reaction are performed under conditions containing no template, but using primers capable of amplifying only the bacterially-derived nucleic acid other than the gene encoding the thermostable DNA polymerase for the preparation.

(B) A thermostable DNA polymerase preparation produced using eukaryotic cells as a host.

The contamination with "10 fg or less" of the bacterially-derived nucleic acid refers to the case in which the contamination level is determined to be "10 fg or less" by a detection method in "(6-3) Detection Limit of PCR" in Example 2-1 to be described later.

For the purpose of the present invention, the "extract" may be a composition containing the thermostable DNA polymerase taken out of cells or fungal cells. The solvent and extraction method used for obtaining the extract are not particularly limited. Examples of the method for obtaining the extract can include the following methods:

(1) A method comprising treating eukaryotic cells having produced the thermostable DNA polymerase with an enzyme lysing cell walls such as Zymolyase, cellulase, chitinase, chitobiase, Chitosanase β-1,3-glucanase, or lysozyme;

(2) A method comprising using a physical method employing an ultrasonic wave, French press, or glass beads, a method comprising rupturing the cell wall or cell membrane by heating, or the like to extract a composition contained in cells or fungal cells employing a solvent such as water or a buffer solution to provide an extract; and (3) A method comprising extracting, outside fungal cells, a thermostable DNA polymerase produced using a method comprising causing the extracellular secretory production of the thermostable DNA polymerase by adding a secretory signal peptide and the like, upstream of the thermostable DNA polymerase gene to provide an extract.

For the purpose of the present invention, the "thermostable DNA polymerase preparation" is a preparation containing a thermostable DNA polymerase, and can be obtained as the extract itself or through various treatments such as purification, dilution, and mixing with a different substance or compound. Examples of the preparation can also include the following:

(A) the extract-derived thermostable DNA polymerase as it is being dissolved in a buffer solution containing phosphoric acid, boric acid, carbonic acid, citric acid, acetic acid, tris, tricine, bis-tricine, veronal, Hepes, Pipes, Caps, Taps, Tes, Mops, Mes, or the like as an ingredient having a buffer action.

(B) the polymerase as it is present together with $MgCl_2$, dNTPs, or the like in a solution.

(C) the solutions (A) and (B) as they are dried by a method such as lyophilization.

Methods for obtaining the "thermostable DNA polymerase preparation" from the "extract" may further include purification, dilution, and mixing with a different substance or compound.

Examples of the purification method include the following methods:

(I) A method using electric charges in ion-exchange chromatography, hydroxyapatite chromatography, or the like, for an extract of a culture medium or the like containing a thermostable DNA polymerase.

(II) A method using specific affinity such as affinity chromatography and a method using difference in hydrophobicity such as reverse phase chromatography.

(III) A column chromatography method using a method utilizing difference in molecular weight such as gel filtration, or the like.

(IV) A method comprising fractionation using ammonium sulfate precipitation, acetone precipitation, PEG precipitation, pH precipitation, or the like.

(V) A method for removing nucleic acid using polyethylenimine or the like.

These methods may be used in a combination of two or more thereof. These methods can concentrate the thermostable DNA polymerase contained in the extract or reduce or remove contaminating protein, nucleic acid and the like derived from the host.

Examples of the dilution method include a method which comprises adding, to the extract, a solvent for mixing with the extract, such as water or the buffer solution.

For the method of mixing with a different substance or compound, the mixed substance or compound is not particularly limited; however, examples thereof include one or two or more selected from the group consisting of potassium chloride, potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, lithium acetate, calcium chloride, β-mercaptoethanol, dithiothreitol, DMSO, glycerol, formamide, tetramethylammonium chloride, PEG, Tween 20, Tween 80, Triton X 100, NP40, DNA, RNA, proteins (enzymes, antibodies, BSA, etc.), dATP, dGTP, dCTP, dTTP, dUTP, dNTPs, SYBR Green, evergreen, SYTO9, and wax.

The "thermophilic bacteria" refers to eubacteria or ancient bacteria (archaebacteria) having an optimal growth temperature of 45° C. or more or viable at 55° C. or more. The thermophilic bacteria which can be applied to the present invention are not particularly limited provided that they fall within the above definition.

The "hyper-thermophilic bacteria" refers to eubacteria or ancient bacteria (archaebacteria) having an optimal growth temperature of 80° C. or more or viable at 90° C. or more. The hyper-thermophilic bacteria which can be applied to the present invention are not particularly limited provided that they fall within the above definition. Currently, 100 types or more of thermophilic and hyper-thermophilic bacteria are isolated and identified, and these may be each applied to the present invention. Examples of such thermophilic or hyper-thermophilic bacteria can include thermophilic or hyper-thermophilic bacteria belonging to the genera *Thermus, Bacillus, Thermococcus, Pyrococcus, Aeropyrum, Aquifex, Sulfolobus, Pyrolobus,* or *Methanopyrus*.

More specific examples thereof include *Thermus aquatics, Thermus thermophilus, Bacillus stearothermophilus, Aquifex pyrophilus, Geothermobacterium ferrireducens, Thermotoga maritime, Thermotoga neopolitana, Thermotoga petrophila, Thermotoga naphthophila, Acidianus infernus, Aeropyrum pernix, Archaeoglobus fulgidus, Archaeoglobus profundus, Caldivirga maquilingensis, Desulfurococcus amylolyticus, Desulfurococcus mobilis, Desulfurococcus mucosus, Ferroglobus placidus, Geoglobus ahangari, Hyperthermus butylicus, Ignicoccus islandicus, Ignicoccus pacificus, Methanococcus jannaschii, Methanococcus fervens, Methanococcus igneus, Methanococcus infernus, Methanopyrus kandleri, Methanothermus fervidus, Methanothermus sociabilis, Palaeococcus ferrophilus, Pyrobaculum aerophilum, Pyrobaculum calidifontis, Pyrobaculum islandicum, Pyrobaculum oguniense, Pyrococcus furiosus, Pyrococcus abyssi, Pyrococcus horikoshii, Pyrococcus woesei, Pyrodictium abyssi, Pyrodictium brockii, Pyrodictium occultum, Pyrolobus fumarii, Staphylothermus marinus, Stetteria hydrogenophila, Sulfolobus solfataricus, Sulfolobus shibatae, Sulfolobus tokodaii, Sulfophobococcus zilligii, Sulfurisphaera ohwakuensis, Thermococcus kodakaraensis, Thermococcus celer, Thermococcus litoralis, Thermodiscus maritimus, Thermofilum pendens, Thermoproteus tenax, Thermoproteus neutrophilus, Thermosphaera aggregans, Vulcanisaeta distributa,* and *Vulcanisaeta souniana*.

The production method for a thermostable DNA polymerase preparation according to the present invention comprises producing a thermostable DNA polymerase using host cells, wherein eukaryotic cells are used as the host cells.

Eukaryotic cells include fungi, animal cells, plant cells, and insect cells. The host cells may be any cells derived from eukaryotic cells and are not particularly limited. Fungi include ascomycetes such as yeast and mold, filamentous fungi, basidiomycetes, and zygomycetes; among others, yeast and filamentous fungi are preferable; and examples thereof include the genera *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium,* and *Trichoderma*.

More specific examples thereof can include *Saccharomyces cerevisiae, Schizosaccharomyces pombe, Candida utilis, Candida boidini, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toruloides, Aspergillus niger, Aspergillus nidulans, Aspergillus awamori, Aspergillus oryzae,* and *Trichoderma reesei*.

Animal cells include human-derived cultured cells and mouse-derived cultured cells; specific examples thereof include CHO cells and Hela cells. The plant cells may be any cells derived from plants; preferred are established cultured cells, including cells of the genus *Nicotiana*, cells of the genus *Arabidopsis*, cells of the genus *Ipomoea*, cells of the genus *Daucus*, and cells of the genus *Oryza*; and specific examples thereof include cultured *Nicotiana tabacum* BY-2 cells, cultured *Arabidopsis thaliana* cells, cultured *Ipomoea batatas* cells, cultured *Daucus carota* cells, and *Oryza sativa* cultured cells. The insect cells may be any cells derived from insects; preferred are established cultured cells, including the cell lines, sf9 and sf21, derived from ovarian cells of *Spodoptera litura* aff. var. *Spodoptera frugiperda* and the *Bombix mori* cell line, Bm-N. The host cells are preferably those derived from a rapidly proliferating microorganism or eukaryotic organism such as yeast; examples thereof include yeasts including the genus *Saccharomyces* such as *Saccharomyces cerevisae*, plant cells including a plant of the genus *Nicotiana* such as *Nicotiana tabacum*, and filamentous fungi including the genus *Aspergillus* such as *Aspergillus oryzae*.

For the production of a thermostable DNA polymerase using eukaryotic cells, there is, for example, a method comprising introducing a gene containing at least one gene encoding the thermostable DNA polymerase into eukaryotic cells for expression to produce the thermostable DNA polymerase.

The gene encoding a thermostable DNA polymerase herein may be any gene such as cDNA, genomic DNA or synthetic DNA encoding a thermostable DNA polymerase, may be a single strand, or a double strand having a complementary strand thereof, and may contain a naturally occurring or artificial nucleotide derivative. In addition, when the thermostable DNA polymerase is derived from an organism, the origin of the thermostable DNA polymerase is also not particularly limited.

DNA polymerase has various congeners depending on the types of organisms.

Specific examples of the thermostable DNA polymerase used for the present invention can include a thermostable DNA polymerase derived from *Thermus aquatics, Thermus thermophilus, Bacillus stearothermophilus, Thermococcus gorgonarius, Thermococcus kodakaraensis* KOD1, *Pyrococcus woesei, Pyrococcus furiosus, Aeropyrum pemix, Aquifex aeolicus, Sulfolobus tokodaii, Pyrolobus fumarii*, or *Methanopyrus kandleri*.

The thermostable DNA polymerase encompasses a thermostable DNA polymerase artificially synthesized by genetic engineering.

The thermostable DNA polymerase is also preferably derived from an organism having thermal resistance, and more preferably derived from a procaryotic organism such as a methane bacterium, a thermoacidophilic bacterium, a thermophilic bacterium, or a hyper-thermophilic bacterium.

The thermostable DNA polymerase gene of the present invention preferably has a base sequence using the codon usage frequently used in a host organism to be transformed.

For example, the codon usage in introducing a thermostable DNA polymerase gene into *Saccharomyces cerevisiae* is given in the following.

When the original thermostable DNA polymerase gene is modified based on the codon usage of a heterogeneous organism such as the genus *Saccharomyces*, the codon usage is preferably applied to 70% or more, more preferably 80% or more, still more preferably 90% or more of the base sequence of the thermostable DNA polymerase gene of natural origin; the codon usage is most preferably applied to all of the codons.

Preferred forms of the thermostable DNA polymerase gene of the present invention include a thermostable DNA polymerase gene designed by applying the codon usage of *Saccharomyces cerevisiae* to the base sequence of a *Thermus aquatics*-derived thermostable DNA polymerase gene. Among others, a thermostable DNA polymerase gene having the sequence of SEQ ID NO: 11 or consisting of any of these base sequences is a preferred aspect.

The thermostable DNA polymerase gene is preferably such that it does not contain a sequence destabilizing mRNA; examples of the sequence destabilizing mRNA include a markedly repeating sequence and a gene sequence with a high GC content, of a thermostable DNA polymerase gene. Specific measures of removing the sequence destabilizing mRNA include the suppression of the appearance of such gene sequence of about 10 bp to 2% or less of the gene encoding a thermostable DNA polymerase, and the design of the thermostable DNA polymerase gene such that the whole gene has a GC content of about 20% to about 45% (both inclusive), and the like.

The thermostable DNA polymerase gene of the present invention preferably has at least one of the following features:
the application of the codon usage of a host organism for introduction,
the design thereof such that no sequence destablizing mRNA is contained, and
the preferred GC content thereof.

The gene, more preferably, has 2 or more, most preferably 3 of the above features. The codon usage of a host is preferably applied to the thermostable DNA polymerase gene. Particularly, when yeast of the genus *Saccharomyces*, especially *Saccharomyces cerevisiae*, is used as a host for transformation, the codon usage of *Saccharomyces cerevisiae* is applied.

In addition, the thermostable DNA polymerase gene, particularly the coding region, is preferably designed so that it has no unsuitable restriction enzyme site for the purpose of performing a gene cloning step. Specifically, it is preferable that sites such as EcoRI, HindIII, NotI, and SnaBI are not contained in the gene. However, in view of gene cloning operation, it is operationally preferable that a useful restriction enzyme site is provided outside the coding region. For example, the restriction enzyme sites such as EcoRI, HindIII, NotI and SnaBI may be provided upstream or downstream of the coding region.

Thermostable DNA polymerase gene homologs include, for example, a DNA polymerase gene homolog capable of hybridizing with any of these DNA under stringent conditions. That is, it is a DNA polymerase gene homolog capable of hybridizing with the whole or part of any of these DNA or a complementary strand thereof under stringent conditions. Such homologs simultaneously encode proteins having a DNA polymerase activity.

The thermostable DNA polymerase gene homolog capable of hybridization under stringent conditions encompasses DNA capable of hybridization using, as a probe DNA(s), DNA(s) in which one or more of arbitrary 20-or-more-base, preferably 25-base, more preferably 30-or-more-base continuous sequences of the original base sequence are selected, by a hybridization technique (Current Protocols I Molecular Biology edit. Ausubel et al., (1987) Publish. John Wily & Sons Sectoin 6.3-6.4) or the like well known to those skilled in the art.

Here, the stringent conditions are a hybridization temperature of 37° C. and the presence of 50% formamide; the more stringent conditions include a temperature of about 42° C. The still more stringent conditions can be about 65° C. and the presence of 50% formamide.

The percentage of mutations in the amino acid sequence is not limited provided that the function of the original protein is maintained; however, it is preferably within 70%, more preferably within 30%, still more preferably within 20% based on the total of the amino acids.

The thermostable DNA polymerase gene homolog is preferably DNA containing or consisting of a base sequence having at least 80%, preferably 90% or more homology to the coding region of the base sequence of the original DNA. The homology of the base sequence of DNA can be determined using the gene analysis program BLAST or the like.

The thermostable DNA polymerase gene can be synthesized chemically or by adopting a method of Fujimoto et al. known as a method for synthesizing long-chain DNA (Hideya Fujimoto, Production method of synthetic gene; Plant Cell Biology series 7; PCR experimental protocol for plant; 1997; Shujunsha; p 95-100).

The amino acid sequence modification can be carried out by properly introducing substitution, deletion, insertion and/or addition mutations into an amino acid sequence to be modified using a site-directed mutation introduction method (Current Protocols I Molecular Biology edit. Ausubel et al., (1987) Publish. John Wily & Sons Sectoin 8.1-8.5) or the like. The modified amino acid sequence is not limited to that obtained by artificial introduction of mutation or synthesis, and also encompasses that generated not only based on artificial mutation treatment but also by amino acid mutation in the nature.

Examples of the thermostable DNA polymerase gene capable of being suitably used for the present invention can include genes consisting of the base sequences represented by SEQ ID NOS: 1, 81 and 82 (corresponding amino acid sequences are shown below).

```
                                                         SEQ ID NO: 1
aagcttacgt atacaacatg agaggtatgc ttccattgtt cgaacctaaa ggtagagtat      60
tgttggttga tggtcatcat ctagcttaca gaactttcca cgctctaaaa ggtttaacaa     120
catcaagagg tgaacctgtt caagctgtat acggttttgc taagtcttta ctaaaagcat     180
tgaaggaaga cggtgacgcc gttattgttg ttttcgatgc taaggcacca agttttagac     240
atgaagcata cggtggttat aaggctggaa gagcaccaac tcctgaagac ttccctagac     300
aattggcact aatcaaggaa ctagtcgact tactaggtct tgcaagatta gaagtcccag     360
gttatgaggc agatgatgta ctagcctctt tagcaaagaa ggcagaaaag gagggttatg     420
aagttagaat tttaaccgct gataaggact tatatcaatt gctatctgat aggattcatg     480
tgttacaccc tgaaggttat ttgataactc cagcttggtt atgggagaag tacggtttga     540
ggccagacca atgggccgat tatagagctt taaccggcga cgagtcagac aatcttccag     600
gtgttaaagg aattggcgaa aagactgcta ggaagttgtt ggaagagtgg ggctccttgg     660
aggccttact taaaaatttg gacaggctaa aaccagcaat cagggaaaag atactagctc     720
acatggatga tcttaaattg tcttgggact tagccaaggt cagaactgat ttgcctttag     780
aggtcgactt cgctaagaga agggaacctg atagggaaag gttaagagcc ttcttggaaa     840
gacttgagtt tggatcatta ttgcatgaat ttggtttatt agaatcccct aaggccttgg     900
aagaagcacc atggccacct ccagaaggtg cctttgtagg cttcgtctta agcaggaaag     960
aaccaatgtg ggcagactta ttggctctag ctgctgccag aggaggaaga gtgcatagag    1020
ccccagaacc atataaagcc ttgagagact tgaaggaagc aagaggtttg ttagctaaag    1080
atttgagcgt attagccttg agggaaggtt taggactacc accaggtgac gacccaatgt    1140
tgcttgctta tttgcttgat ccatcaaaca caacacctga aggagtagct agaaggtatg    1200
gtggagaatg gactgaagag gctggagaga gagccgctct atctgagaga ttgtttgcta    1260
atttgtgggg tagacttgaa ggtgaggaaa gattgttgtg gctatacagg gaagtagaaa    1320
ggccattatc tgcagtattg gctcatatgg aggccacagg cgttagatta gatgttgctt    1380
acttaagagc tttgtcattg gaagtcgccg aagaaattgc aagacttgaa gctgaggtgt    1440
tcagacttgc cggtcatcca ttcaatctta atagtagaga ccagctagaa agagtgttat    1500
tcgacgagct tggattacca gcaatcggaa agacagaaaa gactggtaaa aggtctacaa    1560
gtgccgccgt tttggaagca ttgagggagg cccatccaat tgttgaaaag atattgcagt    1620
atagagaatt gacaaaatta aaatcaactt atatcgatcc acttccagac ttaatccatc    1680
caaggacagg cagattacac accaggttta accagaccgc aactgctaca ggcagattat    1740
catcttcaga tcctaactta caaaacattc ctgtaaggac tccactaggt cagagaatta    1800
```

-continued

```
gaagagcttt tatcgctgag gaaggctggt tgcttgtggc tttagattat agtcaaattg    1860
agttaagggt cttggctcac ttgtctggtg acgaaaatct tatcagagtt tttcaggaag    1920
gtagggatat acatacagag accgcctcat ggatgtttgg tgttccaagg gaggccgtcg    1980
atccactaat gaggagagca gccaaaacta ttaactttgg agtattgtat ggtatgagtg    2040
ctcacagatt atcccaagag ttggccatcc cttacgagga agcacaggct tttatagaaa    2100
ggtatttcca gtcttttcct aaggttagag catggattga aaagacacta gaggaaggta    2160
ggaggagggg ttacgtggag accttattcg gaagaaggag atacgttcca gacttagagg    2220
ctagagtgaa atcagttaga gaagccgcag agagaatggc attcaatatg ccagtacaag    2280
gcactgccgc agatttgatg aaactagcca tggttaagct atttccaaga ttggaagaaa    2340
tgggagctag aatgctatta caagttcatg atgaacttgt tttagaggct cctaaagaaa    2400
gggctgaagc agtggccagg ttagctaaag aagtaatgga gggcgtttac ccattggcag    2460
ttcctttaga ggtcgaagtg ggtataggtg aagactggct atctgcaaag gaataagaat    2520
tc                                                                    2522
```

```
                                                        SEQ ID NO: 81
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa agtttctcgg caagcctatt     240
accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggatcctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaattttgg aaagccaaa ggagaaggta tacgccgacg agatagcaaa gcctgggaa     900 agtggagaga accttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggaaaac    1200
atagtatacc tagattttag agccctatat ccctcgatta taattaccca caatgtttct    1260
cccgatactc taaatcttga gggatgcaag aactatgata tcgctcctca gtaggccac    1320 aagttctgca aggacatccc tggttttata ccaagtctct tgggacattt gttagaggaa    1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg ggaagaaag    1560 tacatcgagt tagtatggaa ggagctcgaa gaaaagtttg gatttaaagt cctctacatt    1620
```

-continued

```
gacactgatg gtctctatgc aactatccca ggaggagaaa gtgaggaaat aaagaaaaag     1680
gctctagaat ttgtaaaata cataaattca aagctccctg gactgctaga gcttgaatat     1740
gaagggtttt ataagagggg attcttcgtt acgaagaaga ggtatgcagt aatagatgaa     1800
gaaggaaaag tcattactcg tggtttagag atagttagga gagattggag tgaaattgca     1860
aaagaaactc aagctagagt tttggagaca atactaaaac acggagatgt tgaagaagct     1920
gtgagaatag taaagaagt aatacaaaag cttgccaatt atgaaattcc accagagaag      1980
ctcgcaatat atgagcagat aacaagacca ttacatgagt ataaggcgat aggtcctcac     2040
gtagctgttg caaagaaact agctgctaaa ggagttaaaa taaagccagg aatggtaatt     2100
ggatacatag tacttagagg cgatggtcca attagcaata gggcaattct agctgaggaa     2160
tacgatccca aaaagcacaa gtatgacgca gaatattaca ttgagaacca ggttcttcca     2220
gcggtactta ggatattgga gggatttgga tacagaaagg aagacctcag ataccaaaag     2280
acaagacaag tcggcctaac ttcctggctt aacattaaaa aatcctag                  2328
                                                         SEQ ID NO: 82
atgatcctcg atacagacta cataactgag gatggaaagc ccgtcatcag gatcttcaag       60
aaggagaacg gcgagttcaa aatagactac gacagaaact ttgagccata catctacgcg      120
ctcttgaagg acgactctgc gattgaggac gtcaagaaga taactgccga gaggcacggc      180
actaccgtta gggttgtcag ggccgagaaa gtgaagaaga agttcctagg caggccgata      240
gaggtctgga agctctactt cactcacccc caggacnnnc ccgcaatcag ggacaagata      300
aaggagcatc ctgccgttgt ggacatctac gagtacgaca tcccttcgc gaagcgctac       360 ctcatagaca aaggcttaat cccgatggag ggcgacgagg aacttaagat gctcgccttc      420
gacatcgaga cgctctatca cgagggcgag gagttcgccg aagggcctat cctgatgata      480
agctacgccg acgaggaagg ggcgcgcgtt attacctgga gaatatcga ccttccctat       540 gtcgacgtcg tttccaccga gaaggagatg ataaagcgct tcctcaaggt cgtcaaggaa      600
aaggatcccg acgtcctcat aacctacaac ggcgacaact tcgacttcgc ctacctcaag      660
aagcgctccg agaagctcgg agtcaagttc atcctcggaa gggaaggag cgagccgaaa       720 atccagcgca tgggcgatcg cttttgcggtg gaggtcaagg gaaggattca cttcgacctc     780
taccccgtca ttaggagaac gattaacctc cccacttaca cccttgaggc agtatatgaa      840
gccatctttg gacagccgaa ggagaaggtc tacgctgagg atatagcgca ggcctgggaa      900
acgggcgagg gattagaaag ggtggcccgc tactcgatgg aggacgcaaa ggtaacctat      960
gaactcggaa aagagttctt ccctatggaa gcccagctct cgcgcctcgt aggccagagc     1020
ctctgggatg tatctcgctc gagtaccgga aacctcgtcg agtggttttt gctgaggaag     1080
gcctacgaga ggaatgaact tgcaccaaac aagccggacg agaggggagct ggcaagaaga    1140 agggagagct acgcgggtgg atacgtcaag gagcccgaaa ggggactgtg ggagaacatc     1200
gtgtatctgg acttccgctc cctgtatcct tcgataataa tcacccataa cgtctcccct     1260
gatacactca caggggaggg ttgtgaggag tacgacgtgg ctcctcaggt aggccataag     1320
ttctgcaagg acttcccggg cttcatccca agcctcctcg agacctctt ggaggagaga     1380 cagaaggtaa agaagaagat gaaggccact atagacccaa tcgagaagaa actcctcgat    1440
tacaggcaac gagcaatcaa aatccttgct aatagcttct acggttacta cggctatgca     1500
aaggcccgct ggtactgcaa ggagtgcgcc gagagcgtta ccgcttgggg caggcagtac    1560
atcgagacca cgataaggga aatagaggag aaatttggct ttaaagtcct ctacgcggac    1620
acagatggat ttttcgcaac aatacctgga gcggacgccg aaaccgtcaa aaagaaggca    1680
```

-continued

```
aaggagttcc tggactacat caacgccaaa ctgcccggcc tgctcgaact cgaatacgag    1740
ggcttctaca agcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaaggggg ataaaaatcc ggcccggaac ggtcataagc    2100
tacatcgtgc tcaaaggctc gggaaggatt ggggacaggg ctatacccct tgacgaattt    2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttggggc gtggctaaaa cctaagacat ga                       2322
```

Amino acid sequence corresponding to the gene consisting of a base sequence of

SEQ ID NO: 1

```
MRGMLPLFEP KGRVLLVDGH HLAYRTFHAL KGLTTSRGEP VQAVYGFAKS LLKALKEDGD     60

AVIVVFDAKA PSFRHEAYGG YKAGRAPTPE DFPRQLALIK ELVDLLGLAR LEVPGYEADD    120

VLASLAKKAE KEGYEVRILT ADKDLYQLLS DRIHVLHPEG YLITPAWLWE KYGLRPDQWA    180

DYRALTGDES DNLPGVKGIG EKTARKLLEE WGSLEALLKN LDRLKPAIRE KILAHMDDLK    240

LSWDLAKVRT DLPLEVDFAK RREPDRERLR AFLERLEFGS LLHEFGLLES PKALEEAPWP    300

PPEGAFVGFV LSRKEPMWAD LLALAAARGG RVHRAPEPYK ALRDLKEARG LLAKDLSVLA    360

LREGLGLPPG DDPMLLAYLL DPSNTTPEGV ARRYGGEWTE EAGERAALSE RLFANLWGRL    420

EGEERLLWLY REVERPLSAV LAHMEATGVR LDVAYLRALS LEVAEEIARL EAEVFRLAGH    480

PFNLNSRDQL ERVLFDELGL PAIGKTEKTG KRSTSAAVLE ALREAHPIVE KILQYRELTK    540

LKSTYIDPLP DLIHPRTGRL HTRFNQTATA TGRLSSSDPN LQNIPVRTPL GQRIRRAFIA    600

EEGWLLVALD YSQIELRVLA HLSGDENLIR VFQEGRDIHT ETASWMFGVP REAVDPLMRR    660

AAKTINFGVL YGMSAHRLSQ ELAIPYEEAQ AFIERYFQSF PKVRAWIEKT LEEGRRRGYV    720

ETLFGRRRYV PDLEARVKSV REAAERMAFN MPVQGTAADL MKLAMVKLFP RLEEMGARML    780

LQVHDELVLE APKERAEAVA RLAKEVMEGV YPLAVPLEVE VGIGEDWLSA KE            832
```

Amino acid sequence corresponding to the gene consisting of a base sequence of

SEQ ID NO: 81

```
MILDVDYITE EGKPVIRLFK KENGKFKIEH DRTFRPYIYA LLRDDSKIEE VKKITGERHG     60

KIVRIVDVEK VEKKFLGKPI TVWKLYLEHP QDVPTIREKV REHPAVVDIF EYDIPFAKRY    120

LIDKGLIPME GEEELKILAF DIETLYHEGE EFGKGPIIMI SYADENEAKV ITWKNIDLPY    180

VEVVSSEREM IKRFLRIIRE KDPDIIVTYN GDSFDFPYLA KRAEKLGIKL TIGRDGSEPK    240

MQRIGDMTAV EVKGRIHFDL YHVITRTINL PTYTLEAVYE AIFGKPKEKV YADEIAKAWE    300

SGENLERVAK YSMEDAKATY ELGKEFLPME IQLSRLVGQP LWDVSRSSTG NLVEWFLLRK    360

AYERNEVAPN KPSEEEYQRR LRESYTGGFV KEPEKGLWEN IVYLDFRALY PSIIITHNVS    420

PDTLNLEGCK NYDIAPQVGH KFCKDIPGFI PSLLGHLLEE RQKIKTKMKE TQDPIEKILL    480

DYRQKAIKLL ANSFYGYYGY AKARWYCKEC AESVTAWGRK YIELVWKELE EKFGFKVLYI    540

DTDGLYATIP GGESEEIKKK ALEFVKYINS KLPGLLELEY EGFYKRGFFV TKKRYAVIDE    600

EGKVITRGLE IVRRDWSEIA KETQARVLET ILKHGDVEEA VRIVKEVIQK LANYEIPPEK    660
```

```
                                -continued
LAIYEQITRP LHEYKAIGPH VAVAKKLAAK GVKIKPGMVI GYIVLRGDGP ISNRAILAEE     720

YDPKKHKYDA EYYIENQVLP AVLRILEGFG YRKEDLRYQK TRQVGLTSWL NIKKS          775

Amino acid sequence corresponding to the gene consisting of a base
sequence of
                                                        SEQ ID NO: 82
MILDTDYITE DGKPVIRIFK KENGEFKIDY DRNFEPYIYA LLKDDSAIED VKKITAERHG      60

TTVRVVRAEK VKKKFLGRPI EVWKLYFTHP QDVPAIRDKI KEHPAVVDIY EYDIPFAKRY     120

LIDKGLIPME GDEELKMLAF DIETLYHEGE EFAEGPILMI SYADEEGARV ITWKNIDLPY     180

VDVVSTEKEM IKRFLKVVKE KDPDVLITYN GDNFDFAYLK KRSEKLGVKF ILGREGSEPK     240

IQRMGDRFAV EVKGRIHFDL YPVIRRTINL PTYTLEAVYE AIFGQPKEKV YAEEIAQAWE     300

TGEGLERVAR YSMEDAKVTY ELGKEFFPME AQLSRLVGQS LWDVSRSSTG NLVEWFLLRK     360

AYERNELAPN KPDERELARR RESYAGGYVK EPERGLWENI VYLDFRSLYP SIIITHNVSP     420

DTLNREGCEE YDVAPQVGHK FCKDFPGFIP SLLGDLLEER QKVKKKMKAT IDPIEKKLLD     480

YRQRAIKILA NSFYGYYGYA KARWYCKECA ESVTAWGRQY IETTIREIEE KFGFKVLYAD     540

TDGFFATIPG ADAETVKKKA KEFLDYINAK LPGLLELEYE GFYKRGFFVT KKKYAVIDEE     600

DKITTRGLEI VRRDWSEIAK ETQARVLEAI LKHGDVEEAV RIVKEVTEKL SKYEVPPEKL     660

VIYEQITRDL KDYKATGPHV AVAKRLAARG IKIRPGTVIS YIVLKGSGRI GDRAIPFDEF     720

DPAKHKYDAE YYIENQVLPA VERILRAFGY RKEDLRYQKT RQVGLGAWLK PKT            773
```

A DNA construct for introducing the above thermostable DNA polymerase gene into a host will be described. Host cells can be transformed with the thermostable DNA polymerase gene of the present invention to express the protein encoded by this DNA to produce the DNA polymerase in the host cells by the DNA polymerase activity thereof.

In the transformation, a DNA construct enabling the expression of the DNA segment consisting of the thermostable DNA polymerase gene in host cells is used. The aspect of the DNA construct for transformation is not particularly limited; a plasmid (DNA), a bacteriophage (DNA), a retrotransposon (DNA), or an artificial chromosome (YAC, PAC, BAC, MAC, etc.) may be selected and adopted depending on the introduction form (extra-chromosomal or intra-chromosomal) of the foreign gene and the type of the host cells. Thus, the DNA construct can be provided with constituent segments of any one or more of these aspects of vectors in addition to the thermostable DNA polymerase gene.

Preferred prokaryotic vectors, eukaryotic vectors, animal cell vectors and plant cell vectors are well known in the art.

Examples of the plasmid DNA can include YCp-type *E. coli*-yeast shuttle vectors such as pRS413, pRS415, pRS416, YCp50, pAUR112 or pAUR123, YEp-type *E. coli*-yeast shuttle vectors such as pYES32 or YEp13, and YIp-type *E. coli*-yeast shuttle vectors such as pRS403, pRS404, pRS405, pRS406, pAUR101 or pAUR135. Examples of the phage DNA can include λ-phages (Charon 4A, Charon 21A, EMBL3, EMBL4, λgt100, gt11, zap), ΦX174, M13mp18, or M13mp19.

Examples of the retrotransposon can include a Ty factor. Examples of YAC can include pYACC2.

To prepare the DNA construct, a fragment or the like containing the thermostable DNA polymerase gene is cleaved with a suitable restriction enzyme and, for example, inserted into the restriction enzyme site or multi-cloning site of the vector DNA used.

A first aspect of the present DNA construct comprises a promoter segment operably linked to the DNA segment consisting of the above-described thermostable DNA polymerase gene. Thus, the thermostable DNA polymerase gene segment is controlled by a promoter and linked downstream of the promoter.

For the expression of the thermostable DNA polymerase gene, when a promoter enabling the expression thereof in yeast is used, it is preferable to use, for example, a gal1 promoter, a gal10 promoter, a pyruvate decarboxylase gene promoter, a heat shock protein promoter, an MFα1 promoter, a PH05 promoter, a PGK promoter, a GAP promoter, an ADH promoter, or an AOX1 promoter.

A second DNA construct as another aspect of the present DNA construct includes a DNA segment for homologous recombination in a host chromosome in addition to the present DNA. The DNA segment for homologous recombination is a DNA sequence homologous to a DNA sequence near a target site into which the thermostable DNA polymerase gene is to be introduced in the host chromosome. The construct includes at least one, preferably two DNA segments for homologous recombination. For example, two DNA segments for homologous recombination are preferably used as DNA sequences homologous to DNA upstream and downstream of the target site on the chromosome to link the thermostable DNA polymerase gene between these DNA segments.

When the thermostable DNA polymerase gene is introduced into a host chromosome by homologous recombination, the present DNA can be introduced into the host chromosome so that it can be controlled by a promoter on the host chromosome. In this case, the introduction of the intended gene simultaneously disrupts an endogenous gene to be controlled by the promoter in nature, and the foreign thermostable DNA polymerase gene can be expressed in place of the endogenous gene. The promoter is particularly useful when it is a high expression promoter in the host cells.

The transformation of a host with the above DNA construct will be described below. Once the DNA construct has been constructed, it can be introduced into suitable host cells by any of various appropriate means such as a transformation method, a transfection method, a conjugation method, protoplast fusion, an electroporation method, a lipofection method, a lithium acetate method, a particle gun method, a calcium phosphate precipitation method, an *Agrobacterium* method, a PEG method, and a direct microinjection method. After introducing the DNA construct, the cells having received the construct are cultured in a selection medium.

In a transformant obtained by transformation with the DNA construct, components of the DNA construct will be present on a chromosome or an extrachromosomal element (including an artificial chromosome). It can be confirmed by a PCR method or a southern hybridization method whether the thermostable DNA polymerase gene has been introduced under a desired promoter or not. For example, the confirmation can be achieved by preparing DNA from the transformant, performing PCR using an introduction site-specific primer, and detecting an expected band in the electrophoresis of the PCR products. Alternatively, the confirmation can also be carried out by performing PCR using a primer labeled with a fluorescent dye or the like. These methods are well known to those skilled in the art.

When yeast is a host cell, a strain in which a yeast gene is disrupted can be used. For example, in the introduction of the gene, the presence of a uracil synthase gene in a plasmid enables the selection of the yeast into which the plasmid is introduced using an uracil auxotroph. A protease-deficient yeast strain can be used to suppress the decomposition of a protein excessively expressed in the yeast cells. These methods are well known to those skilled in the art.

The production of a thermostable DNA polymerase preparation using the above transformant will be described below. A transformant obtained by the introduction of the DNA construct is cultured to produce the thermostable DNA polymerase as an expression product of a foreign gene in a culture. A step of separating the thermostable DNA polymerase from the culture can be performed to provide a thermostable DNA polymerase preparation. For the purpose of the present invention, the culture encompasses cultured cells or fungal cells and crushed cells or fungal cells.

In culturing the transformant of the present invention, culture conditions can be selected depending on the type of the transformant. Such culture conditions are well known to those skilled in the art.

The medium for culturing the transformant obtained using yeast as a host is not particularly limited provided that it is a medium which contains a carbon source, a nitrogen source and inorganic salts utilizable by microorganisms and enables the transformant to be efficiently cultured; both a natural medium and a synthetic medium can be used. However, to produce a thermostable DNA polymerase preparation applicable when a sample microorganism is in trace amounts, it is preferable to use a synthetic medium. For the carbon source, a carbohydrate such as glucose, fructose, sucrose, or starch, an organic acid such as acetic acid or propionic acid, or an alcohol such as ethanol or propanol may be used. For the nitrogen source, ammonia, an inorganic acid or organic acid ammonium salt such as ammonium chloride, ammonium sulfate, ammonium acetate, or ammonium phosphate or another nitrogen-containing compound, peptone, meat extract, corn steep liquor, or the like may be used.

For the inorganic matter, potassium primary phosphate, magnesium phosphate, magnesium sulfate, sodium chloride, ferrous sulfate, manganese sulfate, copper sulfate, calcium carbonate, or the like may be used. The culturing is typically carried out at 30° C. for 24 to 72 hours under aerobic conditions such as shake culture and aerated and agitated culture.

The pH is preferably kept at 5.0 to 7.0 during the period of culture. The pH is adjusted using an inorganic or organic acid, an alkali solution, or the like.

The medium for culturing the transformant obtained using plant cells as a host is not particularly limited provided that it is a medium capable of culturing plant cells, containing a carbon source, a nitrogen source, inorganic salts, organic salts, or the like; examples thereof include MS medium, LS medium, Gamborg B5 medium, WP medium and white medium which are commonly used. Examples of the carbon source include carbohydrates such as glucose, fructose, sucrose, and starch, organic acids such as acetic acid and propionic acid, and alcohols such as ethanol and propanol; among others, sucrose and glucose are preferable. Examples of the nitrogen source include nitrates such as potassium nitrate, sodium nitrate, and calcium nitrate, ammonium salts such as ammonium phosphate, ammonium nitrate, and ammonium sulfate or organic acid ammonium salts or other nitrogen-containing compounds as well as peptone, meat extract, corn steep liquor, and amino acids such as glycine, alanine, histidine, glutamine, glutamic acid, leucine, isoleucine, valine, proline, phenylalanine, tyrosine, tryptophan, lysine, asparagine, aspartic acid, threonine, cysteine, cystine, methionine, serine, and ornithine. Examples of the inorganic salts include potassium primary phosphate, magnesium phosphate, magnesium sulfate, sodium chloride, ferrous sulfate, manganese sulfate, copper sulfate, and calcium carbonate. Examples of the organic matter include vitamins such as thiamine hydrochloride, nicotinic acid, pyridoxine hydrochloride, biotin, folic acid, and para-aminobenzoic acid, as well as inositol, coconut milk, and casein hydrolysate. Plant hormones include auxins such as indoleacetic acid, indolebutyric acid, naphthaleneacetic acid, and 2,4-dichlorophenoxyacetic acid, cytokinins such as zeatin, 6-benzyladenine, and kinetin, abscisic acid, and gibberellic acid; however, when plant cells can be cultured, these plant hormones may be each contained or not contained. The culture is typically carried out at 25° C. for 5 days to 6 weeks under aerobic conditions such as shake culture and aerated and agitated culture.

For the medium for culturing the transformant obtained using animal cells as a host, a commonly used RPMI1640 or DMEM medium or a medium in which fetal bovine serum is added to each of these media can be used. The culture is typically performed 37° C. for 1 to 30 days in the presence of 5% CO2. During culture, an antibiotic such as kanamycin or penicillin may be added to the medium, if necessary.

After the end of culture, a thermostable DNA polymerase can be obtained in a desired form from a culture such as a culture solution or cultured fungal cells. For example, to obtain a preparation containing the thermostable DNA polymerase, methods mentioned herein above can be used. In addition, the thermostable DNA polymerase may be separated and purified from the extracts (e.g., crude extracted fractions) obtained by the extract preparation methods mentioned herein above to make a purified product.

These extracts can each be subjected to various chromatographies, electrophoresis, or the like to provide a purified enzyme preparation. For example, an intended purified gene product can be obtained by properly selecting gel filtration using Sephadex, Ultragel, Bio-Gel, or the like, an electrophoretic method using ion-exchange chromatography, polyacrylamide gel, or the like, or a fractionation method using affinity chromatography, reverse phase chromatography, or the like, or combining these methods. The amino acid sequence of the purified gene product can be analyzed by a known amino acid analysis method. The above-described culture method and purification method are only illustrative and not intended to be limiting.

Particularly, according to the present invention, the majority of the thermostable DNA polymerase is produced in an insoluble form in a culture, and the resultant can be heated to lead to the exhibition of activity and improve the solubility and purity thereof. Heating treatment can be performed at a suitable stage before obtaining the thermostable DNA polymerase in a desired form (e.g., a preparation or a purified product) to solubilize and activate the thermostable DNA polymerase produced by a host fungus. For example, cultured fungal cells are crushed and then centrifuged, and the resultant materials are separated into the supernatant and the precipitate; the precipitate fraction or fungal cells, in which the thermostable DNA polymerase is produced and accumulated, can be subjected to heating treatment to achieve both of the solubilization and activation of the thermostable DNA polymerase. The heating treatment is preferably carried out at 50° C. to 100° C., more preferably 70° C. to 80° C., still more preferably 73° C. to 75° C. for about 1 hour. The supernatant fraction of the culture product can also be heated to insolubilize the host-derived protein and improve the purity thereof. The supernatant fraction of the culture product is preferably heated at 50° C. to 100° C., more preferably 70° C. to 80° C., still more preferably 73° C. to 75° C. for about 1 hour.

In the production of the thermostable DNA polymerase preparation according to the present invention, a gene encoding the thermostable DNA polymerase is introduced and expressed using eukaryotic cells as a host. As a result, the thermostable DNA polymerase preparation to be obtained can have no or extremely reduced contamination with bacterial DNA-derived nucleic acid and the like. Thus, when a purified product thereof is obtained, the requirements for the purification process, various steps or purification degree concerning contamination by nucleic acids are deduced, and, thus, production cost can be reduced.

(2) PCR Method

The PCR method using the thermostable DNA polymerase preparation according to the present invention may be any one of various PCR methods provided that it is a PCR method for amplifying an intended gene for detecting a subject organism to be detected.

Preferred PCR methods can include the following methods:

(A) A typical PCR method or a modified PCR method in which the following a, b, and c are used alone or in a combination of A and B, or A and C.

a. A real-time PCR method using an intercalator, comprising the following procedures:

(a1) The primer is designed so that the Tm value of a PCR amplification product providing that the Tm value of the target is higher than that of the primer dimer itself; and (a2) The temperature in the detection of fluorescence during real-time PCR is set medially therebetween.

b. A PCR method for the semi-nested amplification of a sequence within a target nucleic acid in a specimen, comprising the following stages:

(b-1) The specimen is mixed in an amplification reaction mixture containing an outer PCR primer pair and a semi-nested primer;

(b-2) To provide an outer amplification sequence, the amplification reaction mixture of the stage b1 is placed on DNA serving as a template, and subjected to amplification reaction at a temperature at which the outer PCR primer pair is annealed and extended, but the semi-nested primer pair does not function; and (b-3) To provide a semi-nested amplification product, the mixture of stage b2 is subjected to amplification reaction, either at a temperature at which only one of the outer PCR primers and the semi-nested primer are annealed, or for an extension time during which the two primers are extended.

c. A PCR method for the semi-nested amplification of a sequence within a target nucleic acid in a specimen, comprising the following stages:

(c1) The specimen is mixed in an amplification reaction mixture containing an outer PCR primer pair and a nested primer pair;

(c2) To provide an outer amplification sequence, the amplification reaction mixture of the stage (c1) is placed on DNA serving as a template and subjected to amplification reaction at a temperature at which the outer PCR primer pair is annealed and extended, but the nested primer pair does not function; and (c3) To provide a nested amplification product, the mixture of stage (c2) is subjected to amplification reaction either at a temperature at which only the nested primer pair is annealed, or for an extension time during which the primer is extended.

(B) A PCR method which is a real-time PCR method using an intercalator as a modified PCR method involved in a quantification method and the following procedures:

(a1) The primer is designed so that the Tm value of a PCR amplification product providing a target is higher than the value of the primer dimer itself;

(a2) The temperature in the detection of fluorescence during real-time PCR is set medially therebetween; and (2-3) A modified PCR method involved in the detection method and quantification method of the present invention is a method for the semi-nested amplification of a sequence within a target nucleic acid in a specimen and includes the following stages:

(b1) The specimen is mixed in an amplification reaction mixture containing an outer PCR primer pair and a semi-nested primer;

(b2) To provide an outer amplification sequence, the amplification reaction mixture of the stage b1 is placed on DNA serving as a template and subjected to amplification reaction at a temperature at which the outer PCR primer pair is annealed and extended, but the semi-nested primer does not function; and (b3) To provide a semi-nested amplification product, the mixture of stage b2 is subjected to amplification reaction either at a temperature at which only one of the outer PCR primers and the semi-nested primer are annealed, or for an extension time during which the two primers are extended.

(C) A PCR method for the nested amplification of a sequence within a target nucleic acid in a specimen as a modified PCR involved in the detection method and the quantification method, comprising the following stages:

(c1) The specimen is mixed in an amplification reaction mixture containing an outer PCR primer pair and a nested primer pair;

(c2) To provide an outer amplification sequence, the amplification reaction mixture of the stage c1 is placed on DNA serving as a template and subjected to amplification reaction at a temperature at which the outer PCR primer pair is annealed and extended, but the nested primer pair does not function owing to the inhibitory effect of a intervening primer pair; and (c3) To provide a nested amplification product, the mixture of stage (c2) is subjected to amplification reaction either at a temperature at which only the nested primer pair is annealed, or for an extension time during which the primer is extended.

One of modified PCR methods useful when combined with the thermostable DNA polymerase preparation according to the present invention is a masked Primer Dimer method (method A). Unlike a conventional method for suppressing the formation of a primer dimer, the masked Primer Dimer method is a technique comprising making only a primer dimer non-displayed. The technique is a method for performing real-time PCR using an intercalator by the procedures:

(a1) The primer is designed so that the Tm value of a PCR amplification product providing a target is higher than the Tm value of the primer dimer; and (a2) The temperature in the detection of fluorescence during real-time PCR is set at the median value therebetween, considering that "the primer dimer is small as an amplification product and therefore tends to have a low Tm value".

By going through the above procedures, only the primer dimer is dissociated from a double strand into single strands; thus, the intercalator cannot bind thereto. As a result, the primer dimer does not emit fluorescence, which makes only the primer dimer non-displayed on a monitor, resulting in the intended amplification product normally drawing an amplification curve.

The design of the primers used for the method A is not particularly limited provided that it is such that the Tm value of a PCR amplification product providing a target becomes higher than the value of the primer dimer itself. However, as a specific example, the primers may be designed so that the Tm value of a PCR amplification product providing a target is 5° C. or more, preferably 10° C. or more, higher than the Tm value of the primer dimer itself. For the method A, the temperature in detecting fluorescence during real-time PCR may be set at the median value between the Tm value of a PCR amplification product providing a target and the Tm value of the primer dimmer. However, the median value may have a range in the neighborhood of the median value, e.g., in the neighborhood of 1 to 4° C., i.e., the median value ±1 to ±4, depending on the extent of the Tm value difference between the amplification product and the primer dimer. However, the fluorescence detection temperature is preferably a temperature as possible as low in the above range.

The real-time PCR using an intercalator may be one for which the device and method used are known; examples thereof include real-time PCR using a fluorescent dye such as SYBR Green I as an intercalator.

Another one of modified PCR methods useful when combined with the thermostable DNA polymerase preparation of the present invention is the application of a nested amplification method or the design of the PCR extension time. By applying the nested amplification method or designing the PCR extension time, a nested PCR can be performed using only one round of PCR without separately carrying out two rounds of PCR (one-step nested PCR) as in conventional nested PCR. This one-step nested PCR can be immediately performed after adding a simply designed "nested primer"; thus, it is an idiot-proof method.

The one-step nested PCR is a modification of the PCR of the method B or method C.

Method B: A modified PCR method for the semi-nested amplification of a sequence within a target nucleic acid in a specimen, comprising the following stages:

(b1) The specimen is mixed in an amplification reaction mixture containing an outer PCR primer pair and a semi-nested primer;

(b2) To provide an outer amplification sequence, the amplification reaction mixture of the stage b1 is placed on DNA serving as a template and subjected to amplification reaction at a temperature at which the outer PCR primer pair is annealed and extended, but the semi-nested primer pair is not annealed; and (b3) To provide a semi-nested amplification product, the mixture of stage b2 is subjected to amplification reaction at a temperature at which both of the outer PCR primers and the semi-nested primer are annealed, but only the nested inner PCR amplification product is denatured. Alternatively, it is subjected to amplification reaction for an extension time during which only the nested inner PCR amplification product can be extended.

For the method B, the amplification reaction mixture includes 3 types of primers. That is, a first primer is one of the paired outer PCR primers; a second primer is the semi-nested primer; and a third primer is the other of the paired PCR outer primers and also forms a pair with the semi-nested primer.

For the method B, it is necessary in the stage b2 to use a temperature at which only the outer PCR primer pair is annealed and extended, but the semi-nested primer is not annealed. It is also necessary in the stage b3 to provide a temperature at which outer PCR amplification products are not denatured, but only an inner nested PCR amplification product is denatured and extended. Alternatively, it is necessary in the stage b3 to provide an extension time for which the outer PCR amplification products cannot be extended, but only the inner nested PCR amplification product can be extended. For the method B, the temperature for annealing the semi-nested primer pair is preferably 5° C. to 20° C. lower than the suitable temperature for annealing the outer PCR primer pair.

For the stage a1 of the method B, the primers are preferably present at a constant temperature in the amplification reaction mixture.

For the method B, the Tm values of the first primer and the third primer are preferably the same. For the method B, the second primer is set in the inner side so that it is semi-nested with respect to the first or third primer, and the Tm value of the second primer is preferably 5 to 20° C. lower than the Tm value of each of the first and third primers. For the method B, the outer amplification products are preferably sufficiently larger (about 300 bp or more) than the nested inner amplification product.

Method C: A modified PCR method for the nested amplification of a sequence within a target nucleic acid in a specimen, comprising the following stages:

(c1) The specimen is mixed in an amplification reaction mixture containing an outer PCR primer pair and a nested primer pair;

(c2) To provide an outer amplification sequence, the amplification reaction mixture of the stage c1 is placed on DNA serving as a template and subjected to amplification reaction at a temperature at which the outer PCR primer pair is annealed and extended, but the nested primer pair is not annealed; and (c3) To provide a nested amplification product, the mixture of stage c2 is subjected to amplification reaction at a temperature at which only a nested inner PCR amplification product is denatured. Alternatively, it is subjected to amplification reaction for an extension time during which only the nested inner PCR amplification product can be extended.

For the method C, the amplification reaction mixture includes 4 types of primers. That is, a 4th primer and a 5th primer form an outer PCR primer pair, and a 6th primer and a 7th primer form a nested primer pair. For the method C, it is necessary in the stage c2 to use a temperature at which only the outer PCR primer pair is annealed and extended, but the nested primer pair does not function. It is also necessary in the stage c3 to provide a temperature at which outer PCR amplification products are not denatured, but only the inner nested PCR amplification products are denatured and extended. Alternatively, it is necessary in the stage c3 to provide an extension time for which the outer PCR amplification products cannot be extended, but only the inner nested PCR amplification products can be extended.

For the method C, the temperature for annealing the nested primer pair is preferably 5° C. to 20° C. lower than the suitable temperature for annealing the outer PCR primer pair.

For the stage c1 of the method C, the 4th to 7th primers are preferably present at a constant temperature in the amplification reaction mixture. For the method C, the Tm value of each of the 6th to 7th primers is preferably 5° C. to 20° C. lower than that of each of the 4th to 5th primers. For the method C, the Tm values of the 4th to 5th primers are preferably the same. For the method C, the Tm values of the 6th to 7th primers are preferably the same. For the method C, the outer amplification products are preferably sufficiently larger (about 300 bp or more) than the nested inner amplification products.

<Masked Primer Dimer Method>

In typical PCR condition setting given below, the fluorescence detection point is set at 72° C. after extension.

Target temperature: 94° C., 55° C., 72° C.
Incubation time: 10 seconds
Temperature Transition Rate: 20.00 [° C./s]
Cycle number: 60

Figure 13:
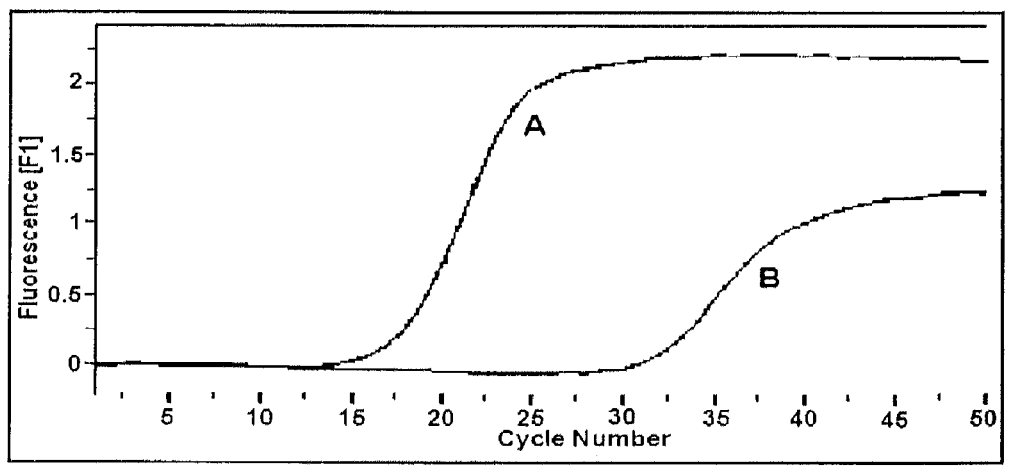
[FIG. 13]
Figure 14:
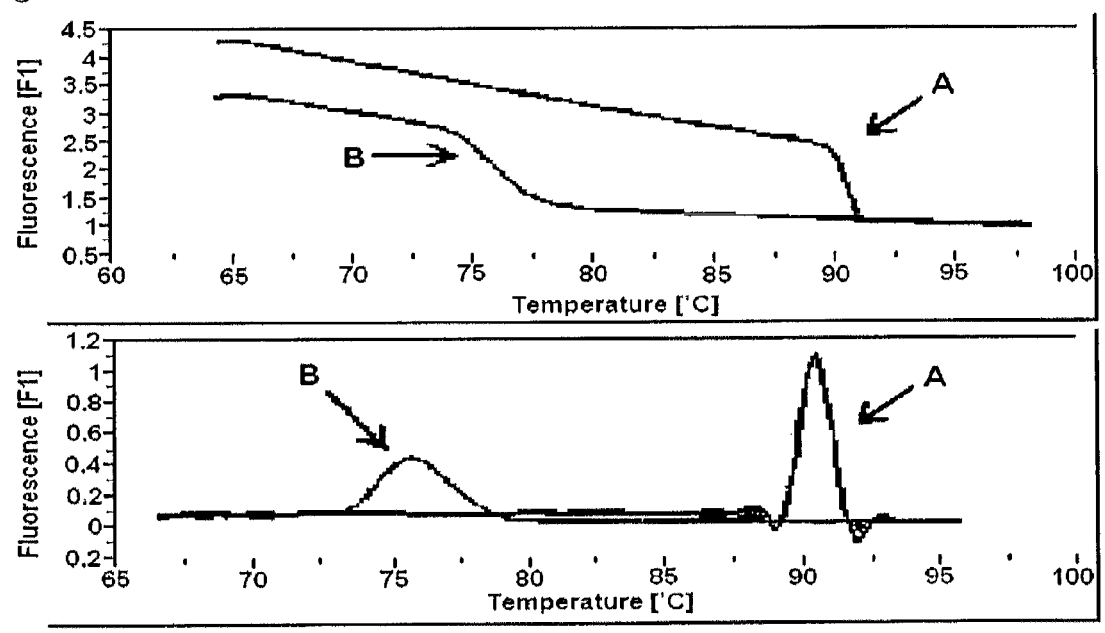
[FIG. 14]

Then a primer dimer (pd) is detected using distilled water (D.W.) as shown by an amplification curve in FIG. 13. At this time, for example, a melting curve in the detection of *E. coli* shows that the Tm value of the primer dimer is about 76° C. and the Tm value of an intended (*E. coli*) PCR amplification product is about 91° C. (FIG. 14).

Figure 10:
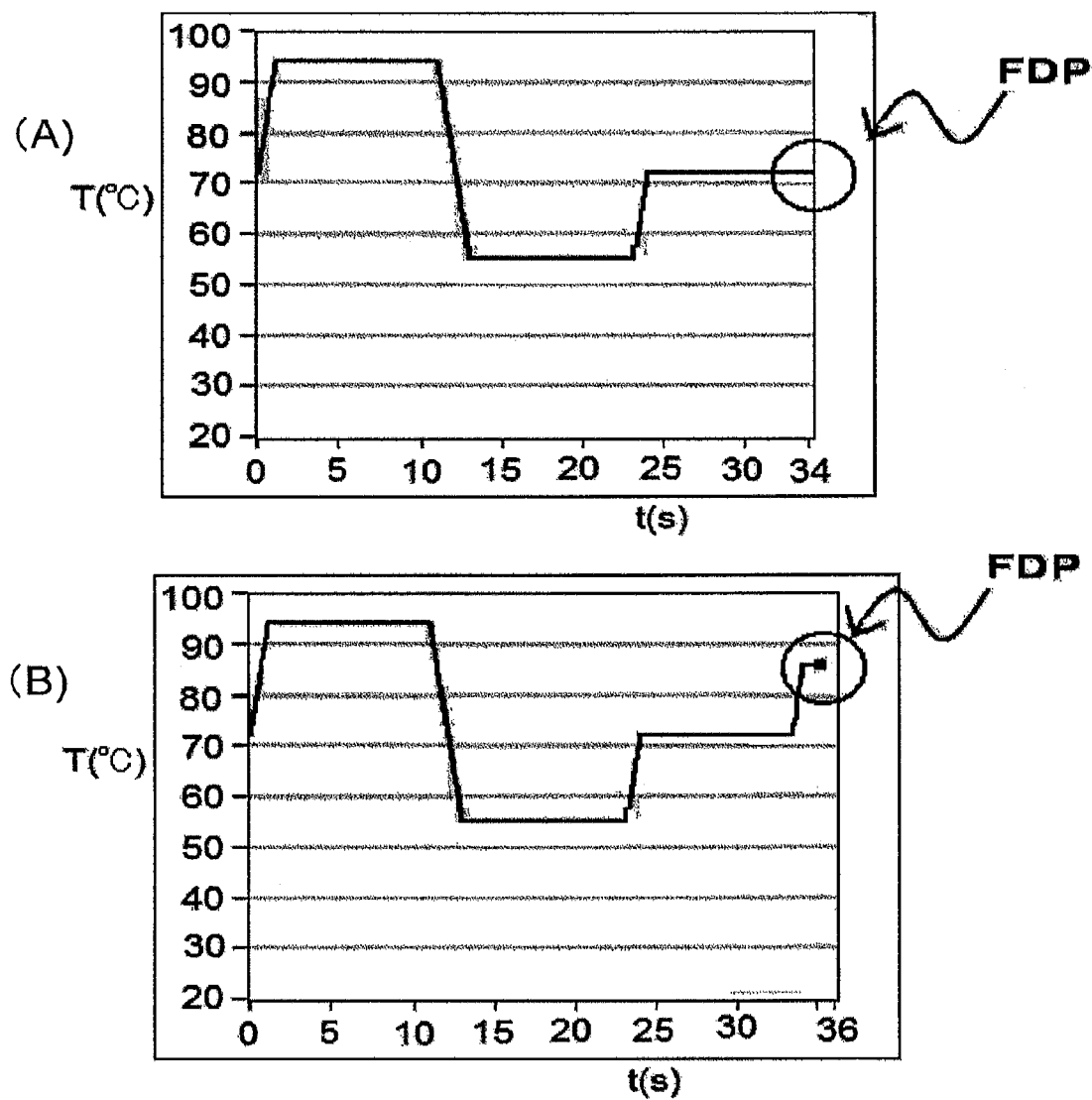
[FIG. 10]

Accordingly, a primer is designed such that the Tm value of the intended PCR product is 10° C. higher than the Tm value of the primer dimer, and the fluorescence detection point (FDP) is set at about the median value therebetween (for example, 86° C. as in the following conditions) (FIG. 10: the temperature may be that at any time instead of after extension).

Target temperature: 94° C., 55° C., 72° C., 86° C.
Incubation time: 10 seconds (94° C., 55° C., 72° C.); 1 second (86° C.)
Temperature transition rate: 20.00 [° C./s]
Cycle number: 60

Figure 15:
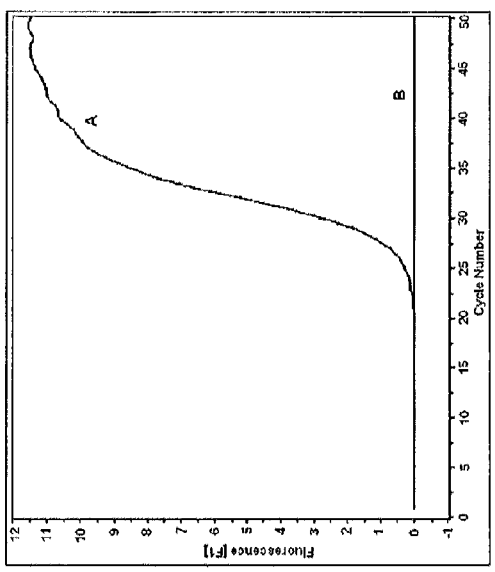
[FIG. 15]
Figure 15:
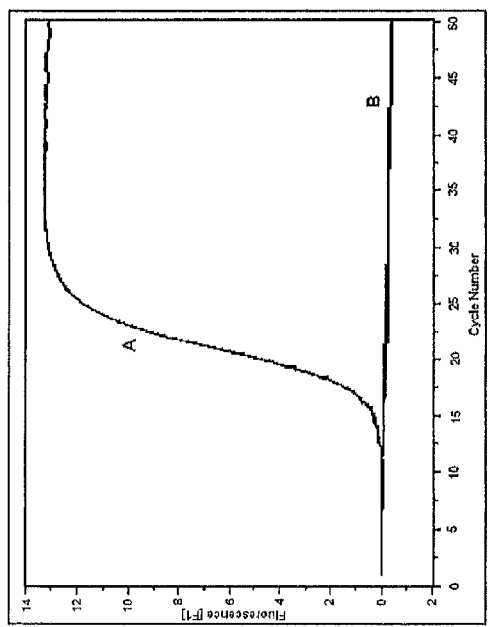
Figure 15:
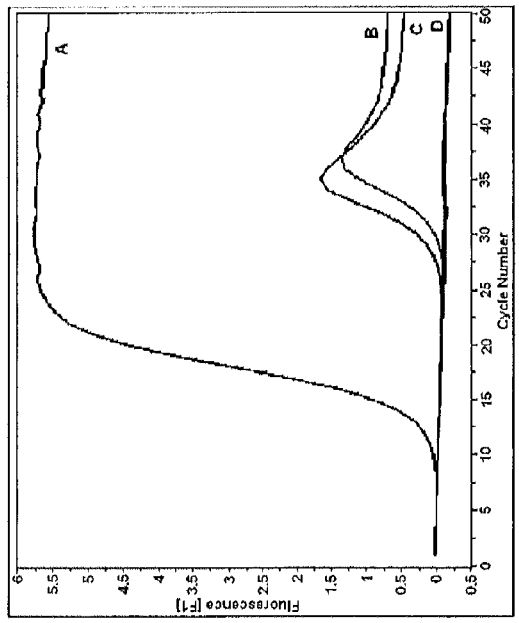

Then no primer dimer is detected. Namely, the primer dimer is non-displayed; thus, the combination thereof with the thermostable DNA polymerase preparation of the present invention can provide an amplification curve indicating no amplification using distilled water (D.W.) as shown in FIG. 15 (A).

The combination of "non-display method+thermostable DNA polymerase of the present invention+bacterial universal primers" enables the measurement of a bacterium to the detection limit (FIG. 14), and has been shown to be capable of quantification accurate to the detection limit since the standard curve shows linearity to the detection limit. Namely, it is made possible to quantitatively measure bacteria with high sensitivity and accurately by the real-time PCR method using an intercalator only after adding the masked Primer Dimer method to the present invention.

<One-Step Nested PCR Method>

The following primers are designed (see FIG. 11(A)).

(a) The Tm values of forward and reverse primers for an outer PCR product (amplification product I) shall be the same or close to each other.

(b) A primer (primer II) is set inside which is semi-nested with respect to one of the primers for the outer PCR product.

(c) The semi-nested primers are designed such that they have Tm values of 5 to 20° C. lower than those of the primers for the outer PCR product.

(d) The primers are designed so that the amplification product I has a length of about 400 bp or more to set the Tm value of the outer PCR product (amplification product I) at 89° C. or more.

(e) The primer is designed so that the amplification product II has a length of about 100 bp to set the Tm value of a semi-nested PCR product (amplification product II) at 86° C. to 87° C.

Figure 11:
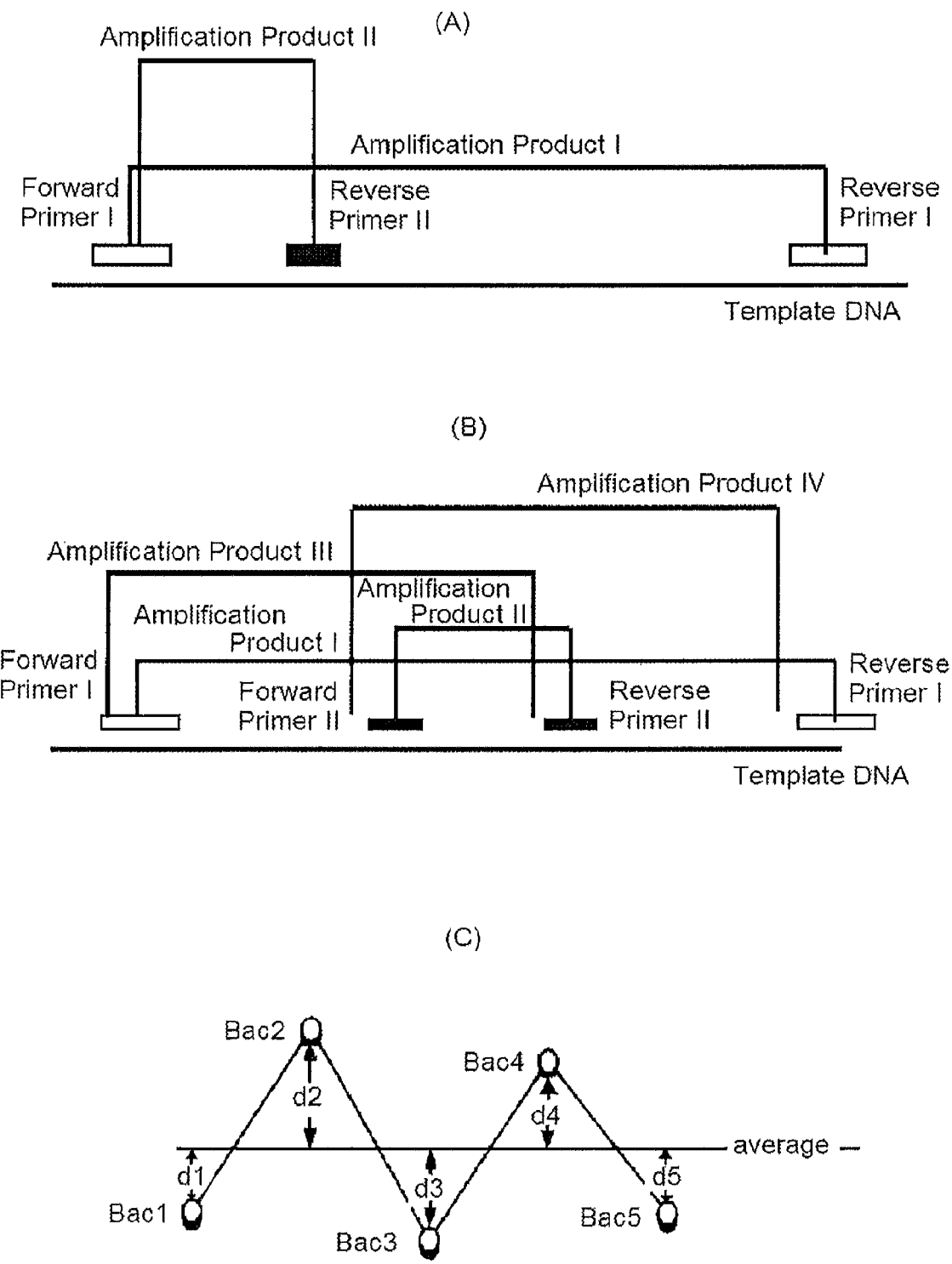
[FIG. 11]

When more specific nested PCR is performed, the following new primers are designed (see FIG. 11 (B)).

(a) The Tm values of forward and reverse primers for an outer PCR product (amplification product I) shall be the same or close to each other.

(b) The Tm values of two nested primers (primer II) are set at sufficiently low (by 5 to 20° C.) compared to the Tm values of the primers for the amplification product I.

(c) The primers are designed so that the amplification product I has a length of about 500 bp or more to set the Tm value of the amplification product I at 89° C. or more.

(d) The primers are designed so that the amplification product II has a length of about 100 bp to set the Tm value of the amplification product II at 86° C. to 87° C.

(e) The primers are designed so that the amplification products III and IV have lengths of about 300 bp or more to set the Tm values of the amplification products III and IV at 89° C. or more.

(3) Method for Detecting Subject Organism to be Detected (Detection Method)

The detection method for a subject organism to be detected in a sample according to the present invention comprising:

(1) an amplification step of performing a nucleic acid amplification reaction using nucleic acid prepared from the sample, primers for amplifying an intended gene specific for the subject organism to be detected, and the thermostable DNA polymerase preparation according to the present invention; and (2) a detection step of detecting an amplification product of the intended gene in amplification products in the amplification step.

For this detection method, the amplification step is preferably carried out under the suppression of amplification of an unintended gene other than the intended gene. A Hot Start method using an anti-DNA polymerase antibody can be preferably used for the suppression of amplification of an unintended gene. In this regard, the anti-DNA polymerase antibody is preferably used in excessive amounts based on 1 U of the thermostable DNA polymerase.

The detection step of the method can detect the amplification product of the intended gene without detecting an amplification product of a different unintended gene. For this step, a method is preferably used in which conditions of enabling the detection of the amplification product of the intended gene without detecting an amplification product of a different unintended gene are set by:

(1) designing the primers so that the melting temperature ($Tm^A$) of the intended gene amplification product is higher than the melting temperature ($Tm^B$) of the unintended gene amplification product; and (2) carrying out amplification product detection at a temperature between $Tm^A$ and $Tm^B$ to detect only the amplification product of the intended gene.

In addition, a method can be used in which the amplification step and the detection step are performed by real-time PCR using a display device for displaying the amount of an amplification product and the amplification product of an unintended gene is not to be displayed on the display device.

A labeled intercalator for detection can be used to detect the amplification product.

The detection step can be performed by developing the amplification product on a gel. The amplification product can be developed by gel electrophoresis for visualization.

Examples of the subject organism to be detected can include one or two or more selected from the group consisting of bacteria, fungi, and viruses.

The detection method of the present invention can achieve the detection of a causative microorganism of an infection in a sample with high sensitivity. In addition, the detection method of the present invention can be suitably applied to a sample which should be in a sterile environment, selected from the group consisting of blood, cerebrospinal fluid, amniotic fluid, urea, foods (including a food processing environment to be subjected to contamination analysis), beverages, cosmetics, and samples provided for water quality analysis and contamination analysis of biological experimental environments. Examples of the sample provided for water quality analysis can include tap water, water from water storage or water supply tank, air-conditioning circulating water, humidifier water, hot spring water, or swimming pool water.

In the detection step, the amplification product of the intended gene is quantified, and the quantification results can be used to perform the quantification of a subject organism to be detected in a sample; the measurement of the number of individuals thereof; the monitoring of the amount present thereof; and the quantification/identification thereof. The quantification method for a subject organism to be detected in a sample will be described below.

(Quantification Method)

The method for quantifying a subject organism to be detected in a sample according to the present invention comprises:

(1) an amplification step of performing a nucleic acid amplification reaction using DNA prepared from the sample, primers for amplifying an intended gene specific for the subject organism to be detected, and the thermostable DNA polymerase preparation according to the present invention; and (2) a quantification step of quantifying the amplification product in the amplification step and quantifying the subject organism to be detected in the sample from the quantification results obtained.

The subject organism to be detected may be any organism having a nucleic acid for transferring information; examples thereof can include bacteria (eubacteria or ancient bacteria), fungi, and viruses. The quantification method of the present invention using the thermostable DNA polymerase preparation according to the present invention is suitable particularly for the quantification of bacteria. The quantification can be carried out by comparing the results of detecting the amplification product with the results obtained using a reference organism. The quantification method of the present invention can quantify the number of individuals of a subject organism to be detected in the sample and the total mass thereof. In addition, a gene for identification of a subject organism to be detected can be used as an intended gene to quantify and identify the subject organism to be detected contained in a sample from the results of quantifying an amplification product of the intended gene.

For the nucleic acid from a sample, cDNA prepared based on the DNA obtained from the sample or further the RNA obtained from the sample can be used. RNA may also be used directly as a subject to be amplified, according to the particular object.

Examples of the sample include a sample which should be in a sterile environment. Examples of the sample which should be in a sterile environment can include a specimen sampled from humans or domestic animals, such as blood, cerebrospinal fluid, amniotic fluid or urea. In addition, for the sample, a sample provided for water quality analysis can be used. Examples of the sample provided for water quality analysis can include tap water, water from water storage or water supply tank, air-conditioning circulating water, humidifier water, hot spring water, or swimming pool water. In addition, for the sample, a sample such as a food, a beverage, a cosmetic, or a cell culture in a biological experimental environment can be used in which organic matters are contained and the presence or proliferation of bacteria or fungi results in the deterioration of the quality thereof.

DNA can be prepared from a sample by a conventional method. When a DNA preparation is provided for the amplification step, a DNA preparation can be subjected to the removal of components other than DNA and the adjustment of concentration, as needed.

PCR, especially real-time PCR, can be suitably applied to the amplification step. For the detection of an amplification product, various known methods can be used. Examples thereof include a method using an intercalator having a labeling function and a method using a probe in which a fluorescent substance is bonded to a nucleotide capable of specifically hybridizing to a DNA sequence to be amplified. Examples of the intercalator include ethidium bromide and SYBR Green I. The intercalator is preferably SYBR Green I. When universal primers, reacting with all bacteria DNA, are used, the SYBR Green I to be used is preferably high purity SYBR Green I in which contamination with recombinant host-derived bacterial DNA is minimized.

For this method, the amplification step is preferably performed under conditions in which the amplification of an unintended gene other than an intended gene is suppressed. Methods for the suppression of amplification of an unintended gene include, for example, a Hot Start method, a method using modified primers, a method involving adding a substance binding to a primer dimer to a sample, and a method involving adding a chemical substance into a gene amplification solution containing a thermostable DNA polymerase. The Hot Start method is preferable. Examples of the Hot Start method include a method using an anti-DNA polymerase antibody and a wax method involving separating the enzyme and primers until wax reaches the melting temperature. When the method using an anti-DNA polymerase antibody is performed, the anti-DNA polymerase antibody is preferably used in an excessive amount exceeding the amount in which the enzymatic activity of the thermostable DNA polymerase is inhibited by 100%.

(Non-Display Method)

In addition, the amplification product is quantified by a non-display method to enable simple quantification with high sensitivity. The non-display method is a method which involves detecting the amplification product under conditions in which the amplification product of an intended gene is put in a detectable state and the amplification product of a different unintended gene is put in a non-detectable state.

Specifically, the conditions of enabling the detection of the amplification product of the intended gene without detecting an amplification product of a different unintended gene are set by:

(1) designing the primers so that the melting temperature ($Tm^A$) of the intended gene amplification product is higher than the melting temperature ($Tm^B$) of the unintended gene amplification product; and (2) carrying out the quantification of the amplification product at a temperature between $Tm^A$ and $Tm^B$.

The non-display method is suitably applied to a real-time PCR method using a display device for displaying the amount of an amplification product for the amplification of an intended gene and the quantification of an amplification product. The use of this method makes the amplification product of the unintended gene non-displayed on the display device in quantitatively analyzing the amplification product, which enables the elimination of the influence of the amplification product of the unintended gene on sensitivity.

For the unintended gene, the particular problem is a primer dimer. When the amount of DNA prepared from a sample is very small, a primer is present in an excessive amount based on the DNA prepared from the sample in the initial stage of amplification. When a primer dimer is formed, an amplification product based on the dimer is formed, making impossible the monitoring or quantification of an amplification product of DNA to be essentially detected. For the occurrence of a primer dimer, the Hot Start method and/or the non-display method is preferably used.

It is extremely difficult to completely inhibit the formation of a primer dimmer. Even if various methods for suppressing the formation of a primer dimer are used, there are cases that a primer dimer is detected in response to an increase in the number of PCR cycles. This is a contribution to a reduction in the sensitivity of quantitative measurement using real-time PCR. Even for qualitative analysis, it may be necessary to adopt a technique which involves checking a Tm value (melting temperature) in each measurement to exclude "false-positivity" due to the primer dimer.

Unlike a conventional method for suppressing the formation of a primer dimer, the non-display method is a method involving making only a primer dimer non-displayed (a masked Primer Dimer method), and has been completed, considering that "the primer dimer is small as an amplification product and therefore tends to have a low Tm value".

To perform the masked Primer Dimer method using real-time PCR, the following conditions are set:

(1) The primer is designed so that the Tm value of a PCR amplification product providing a target is higher than the Tm value of the primer dimer; and (2) The temperature in the detection of the amplification product during real-time PCR is set at the median value therebetween.

The setting of the above conditions dissociates only a double-stranded primer dimer into single strands in the detection of the amplification product. In detecting the amplification product (double-stranded DNA), the use of a marker for not detecting single-stranded DNA but detecting only double-stranded DNA, e.g., an intercalator, makes the bonding of the intercalator impossible, because only the double-stranded primer dimer is dissociated into single strands. As a result, a detection signal based on the primer dimer is not provided. Only the primer dimer is non-displayed on a display device (such as a monitor) and the intended amplification product results in the normal drawing of an amplification curve.

When the non-display method is used, the design of primers is not particularly limited provided that it is such that the Tm value of a PCR amplification product providing a target is higher than the value of the primer dimer itself. However, the design of primers may be performed so that the Tm value of the PCR amplification product providing a target 5° C. higher, preferably 10° C. higher than the Tm value of the primer dimer itself. The Tm value of the amplification product is set depending on the measurement system used.

Specifically, (1) Primers from, from which a primer dimer is difficult to be produced, are designed by a conventional designing method;

(2) The design is performed so that the Tm values of primers themselves are 60° C. or lower; and (3) By calculation using a nearest neighbor method, the design is performed so that the Tm value of a PCR amplification product providing a target is about 87° C. or higher.

The size of the amplification product obtained by amplification using these primers is not particularly limited provided that it is a size designed so that the Tm value of the product is higher than that of the primer dimer itself. However, the primers are preferably designed so that the size thereof is on the order of 50 bp to 1,000 bp, preferably 50 bp to 500 bp, which are suitable for amplification using real-time PCR.

The fluorescence detection temperature during the real-time PCR may be set at the median value between the Tm value of the PCR amplification product providing a target and the Tm value of the primer dimer; the median value may have a range in the neighborhood of the median value, e.g., in the range of ±1 to ±4° C. of the median value, depending on the extent of the Tm value difference between the amplification product and the primer dimer. However, the fluorescence detection temperature is preferably set at a temperature as low as possible in the above range, considering the stability of the double stranded DNA.

The real-time PCR using an intercalator may use a device, a technique, and the like which are generally known; for example, real-time PCR using SYBR Green I as an intercalator is mentioned.

The use of a masked Primer Dimer method can perform quantitative analysis without reducing sensitivity and eliminates the risk of false positivity due to a primer dimer in qualitative examination, because the formation of the primer dimer becomes no longer a hindrance for the real-time PCR method using an intercalator. In addition, the method of the present invention is simple and economical compared to conventional methods such as a Hot Start method using an anti-DNA polymerase antibody.

The non-display method enables measurement to the detection limit; in addition, since the standard curve shows linearity to the detection limit, it is made possible to perform accurate quantitative measurement with high sensitivity by the real-time PCR method.

(Quantification of Subject Organism to be Detected from Amplification Product Using PCR Method)

For the determination of the amount of a subject organism to be detected (including the absence thereof) from the amplification product, there can be preferably used a method for determination based on a standard curve obtained from the known amounts of the subject organism to be detected under conditions (protocol) in which the amplification is carried out. For example, if the detection limit (sensitivity) at 35 cycles is 0.1 CFU/ml in the standard curve drawn using a particular protocol, 35 cycles of PCR reaction can be performed to calculate the amount of a subject organism to be detected in reference to the standard curve. Addition of a sample concentration step or an ethanol treatment step to the protocol can further increase the detection limit (sensitivity)

(e.g., to about 60 cycles). Then, the sensitivity can be set, for example, at an extremely high level of 0.000001 CFU/ml. The detection sensitivity capable of being set can be calculated in advance. For example, for the quantification for daily life water by a "high sensitivity method for quantifying a subject to be detected", because the PCR detection sensitivity of universal primers for bacteria is 10 fg/μl and the PCR detection sensitivity of universal primers for fungi is 10 pg/μl, the following values will be obtained, using a conversion formula for conversion to the unit of CFU/ml and further considering that 50 ml of a sample is first pelletized and then subjected to DNA extraction:

bacterium: $3.0 \times 10^{-1}$ CFU/ml
fungus: 2.8 CFU/ml.

The detection sensitivity can be varied by modifying the protocol.

(Quantification of Subject Organism to be Detected from Amplification Product Using Gel Development Method)

An amplification product (including that obtained using a Hot Start method) can be developed on an agarose gel or the like to simply quantify a subject organism to be detected by fluorescent intensity in the detection of fluorescence, or the like.

(Method for Determining Presence of Bacterium)

The thermostable DNA polymerase according to the present invention can also be suitably used for the following methods.

(I) A method for determining the presence of a bacterium in a sample, comprising:

(1) a first amplification step of performing a nucleic acid amplification reaction using primers for amplifying an intended gene specific for the bacterium (B) and a preparation containing a thermostable DNA polymerase produced using eukaryotic cells as a host; and (2) a step of visualizing the amplification product in the first amplification step, wherein the primers (B) is:

(B) a primer set capable of amplifying a plurality of regions of the 16S rRNA genes of all bacteria and primers containing all or ⅓ or more of each of the base sequences of the above primers.

Gel electrophoresis may be used as a method for visualizing the amplification product.

(II) A method for monitoring the amount present of a bacterium in a sample, comprising:

(1) a first amplification step of performing a nucleic acid amplification reaction using primers for amplifying an intended gene specific for the bacterium (B) and a preparation containing a thermostable DNA polymerase produced using eukaryotic cells as a host; and (2) a step of digitalizing the amplification product in the first amplification step, wherein the primers (B) is:

(B) a primer set capable of amplifying a plurality of regions of the 16S rRNA genes of all bacteria and primers containing all or ⅓ or more of each of the base sequences of the above primers.

An absorbance-measuring method or a densitometric method may be used as a method for digitalizing the amplification product.

(Quantification/Identification Method)

The quantification methods for a subject organism to be detected in a sample can be applied to the following methods for quantifying and identifying a subject organism to be detected.

(A) A quantification/identification method for a subject organism to be detected in a sample, comprising:

(1) a first amplification step of performing a nucleic acid amplification reaction using DNA prepared from the sample, primers (B) and (M), for amplifying an intended gene specific for the subject organism to be detected, and the thermostable DNA polymerase preparation according to the present invention, (2) a first quantification/identification step of analyzing a combination of melting temperatures (Tm values) of a plurality of amplification products (3 to 10 products) in the first amplification step based on a combination of melting temperatures (Tm values) specific for an amplification product of the intended gene to perform the quantification/identification of the subject organism to be detected in the sample, (3) a second amplification step of performing a nucleic acid amplification reaction using DNA prepared from the sample, primers (F), for amplifying an intended gene specific for the subject organism to be detected, and a thermostable DNA polymerase preparation produced using a bacterium as a host, and (4) a second quantification/identification step of analyzing a combination of melting temperatures (Tm values) of a plurality of amplification products (3 to 10 products) in the second amplification step based on a combination of melting temperatures (Tm values) specific for an amplification product of the intended gene to quantify the amplification products in the first quantification/identification step of quantifying and identifying the subject organism to be detected and the second amplification step to perform the quantification/identification of the subject organism to be detected in the sample from the quantification results obtained, wherein the primers (B), (F) and (M) are:

(B) a primer set capable of amplifying a plurality of regions of the 16S rRNA genes of all bacteria and primers containing all or ⅓ or more of each of the base sequences of the above primers, (F) a primer set capable of amplifying a plurality of regions of the 18S rRNA gene of all fungi and primers containing all or ⅓ or more of each of the base sequences of the above primers, and (M) a primer set specifically amplifying an antibiotic resistance gene according to an epidemic of the time such as a mec A gene exhibiting methicillin resistance.

(B) A quantification/identification method for a subject organism to be detected in a sample, comprising:

(1) a first amplification step of performing a nucleic acid amplification reaction using DNA prepared from the sample, primers (B), for amplifying an intended gene specific for the subject organism to be detected, and a thermostable DNA polymerase preparation according to the present invention, (2) a first quantification/identification step of analyzing a combination of melting temperatures (Tm values) of a plurality of amplification products (3 to 10 products) in the first amplification step based on a combination of melting temperatures (Tm values) specific for an amplification product of the intended gene to perform the quantification/identification of the subject organism to be detected in the sample, (3) a second amplification step of performing a nucleic acid amplification reaction using DNA prepared from the sample, primers (F), for amplifying an intended gene specific for the subject organism to be detected, and a thermostable DNA polymerase preparation produced using a bacterium as a host, (4) a second quantification/identification step of analyzing a combination of melting temperatures (Tm values) of a plurality of amplification products (3 to 10 products) in the second amplification step based on a combination of melting temperatures (Tm values) specific for an amplification product of the intended gene to quantify the amplification products in the first quantification/identification step of quantifying/identifying the subject organism to be detected and the second amplification step to perform the quantification/identification of the subject organism to be detected in the sample from the quantification results obtained, (5) a third amplification step of performing a nucleic acid amplification reaction using DNA prepared from the sample, primers (M), for amplifying an intended gene specific for the subject organism to be detected, and a thermostable DNA polymerase preparation according to the present invention, and (6) a third quantification/identification step of analyzing melting temperatures (Tm values) of amplification products in the third amplification step based on a combination of melting temperatures (Tm values) specific for an amplification product of the intended gene to perform the quantification/identification of the subject organism to be detected in the sample, wherein the primers (B), (F) and (M) are:

(B) primers which can be selected from the group consisting of a primer set capable of amplifying a plurality of regions of the 16S rRNA genes of all bacteria and primers containing all or ⅓ or more of each of the base sequences of the above primers, (F) primers which can be selected from the group consisting of a primer set capable of amplifying a plurality of regions of the 18S rRNA gene of all fungi and primers containing all or ⅓ or more of each of the base sequences of the above primers, and (M) a primer set specifically amplifying an antibiotic resistance gene reflecting an epidemic of the time such as a mec A gene exhibiting methicillin resistance.

According to the invention of the present application, the primers containing a portion of each of the primers constituting each primer set need only to have no loss of function as a universal primer (the function of recognizing a particular common region); examples thereof can include primers each obtained by deleting or adding 1 to 3 bases in each of the base sequences designed as universal primers.

It is preferable to set 3 to 10 amplification regions as amplification regions of the bacterial 16S rRNA genes. It is also preferable to set 3 to 10 amplification regions as amplification regions of the 18S rRNA gene of fungi.

In addition, a reference Tm value can be measured in each cycle using any one of "a primer set capable of amplifying a plurality of regions of the 16S rRNA genes of all bacteria and a set of primers containing all or ⅓ or more of each of the base sequences of the above primers" to add a step of correcting the measurement error of the Tm value of the amplification product for measurement with higher precision.

For an algorithm for identifying the subject organism to be detected, not only a combination of the Tm values themselves but also a combination of differences between the Tm values can be used for identification to add a step of minimizing the influence of measurement errors.

"Calculating the average of the combination of Tm values to combine the relative values of the Tm values to the average value" can be used as a method for correcting a measurement error in each measurement cycle of a device without requiring the "measuring a standard Tm value in each cycle". Namely, it is a method in which the arrangement of the combinations of Tm values is used as a "shape" for identification. The "shape" two-dimensionally showing the arrangement of the combinations of the Tm values is not affected by measurement errors. For example, the combination of Tm values (n values) specific for the subject organism to be detected consists of T 1db to T ndb (db=database) and the relative values to the average value thereof be d 1db to d ndb, respectively (FIG. 11(C); the case of n=1 to 5). Similarly, the combination of Tm values (n values) for an unknown organism to be detected obtained from a sample consists of T 1ref to T nref (ref=reference) and the relative values to the average value thereof be d 1ref to d nref, respectively (FIG. 11(C)). Then, comparison with the database is performed to use "the approximation of the combination of the relative values thereto=the similarity of the "shape" of the arrangement of the combination of the Tm values thereto" as an identification algorithm. Thus, the organism for which the result of the calculation formula:

$$\text{Dist.}=\sqrt{(D1_{db}-D1_{ref})^2+(D2_{db}-D2_{ref})^2+\ldots+(D7_{db}-D7_{ref})^2}$$ [Formula 1]

is closest to zero can be identified as a wanted subject organism to be detected. The above algorithm can be used as a database-type identification software on a computer.

The methods (A) and (B) have been first accomplished by applying the results (WO2007/097323) to the quantification technique achieved using the thermostable DNA polymerase preparation of the present invention. The results (WO2007/097323) was obtained by intensive studies of the application of the difference of Tm values among strains to the identification of a subject organism to be detected, based on the theoretical rationale that "the melting temperature (Tm value) depends on the base sequence" for the nearest neighbor method.

These methods will be specifically described below.

(1) Bacterial 16S rRNA are known to have 7 to 10 base sequence regions (20 to 40 bases) common to almost all bacteria.

Forward and reverse primers are set on portions of all or part thereof to prepare 3 to 10 gene amplification regions.

(2) The gene amplification regions each consist of about 150 to 200 bases, and each of the regions excluding the common conserved regions, on which primers are set, have a base sequence specific to each bacterium.

Thus, the Tm value reflects differences in the base sequence to show a characteristic value, and each bacterium is estimated to have 1 to 10 characteristic Tm values. Therefore, the Tm values ranging from 1 to 10 depending on the types of bacteria are examined for compilation of a database. The database can be used to identify an unknown bacterium.

(3) In addition, 3 to 10 primers specific for fungi are used in combination with primers for an antibiotic resistance gene reflecting an spread epidemic of the current time such as a mec A gene exhibiting methicillin resistance to identify bacterial infection or its type (including the presence of an antibiotic resistance gene) or fungal infection or its type with respect to an unknown causative agent.

(4) When a non-specific gene product is produced and has a value close to a desired Tm value, the risk of false positivity occurs.

In such a case, amplification products after gene amplification can be run through an agarose gel to confirm the size of bands to double-check the results.

Thus, a conventional system for double-checking by a detection method using gene amplification can be adopted to improve the precision of examination.

Alternatively, the risk of false positivity due to a non-specific amplification product can be almost completely eliminated by the combination of "the method of solution of a primer dimer problem such as a masked Primer Dimer method+the thermostable DNA polymerase preparation of the present invention+universal primers for bacteria".

(5) When real-time PCR is adopted as a gene amplification method, the quantitatively thereof can be used to perform the relative quantification of the bacterial amount before and after treatment to improve the monitoring of a therapeutic effect.

(6) There are two types of real-time PCR devices: a heating block-type one in which the temperature is controlled with a heating block and an airbus-type one in which the temperature is controlled via air. A Tm value measurement error of ±0.1° C. to ±0.3° C. (which varies depending on the manufacturer) occurs when the heating block-type is used (the error between samples is about ±0.2° C. in the same measurement cycle). It is preferable to adopt a method using a difference pattern between the Tm values in the same measurement cycle for determination so that the measurement error does not disturb the strain identification. On the other hand, the airbus-type Rotor gene 6000 (Qiagen Inc.) has a temperature uniformity between tubes of ±0.01° C., which is preferable since a Tm value measurement error less easily occurs.

(7) In the case of infection with a plurality of bacteria, if after the ascending of the amplification curve by real-time PCR, the amplification cycle is stopped once a plateau is reached and the Tm values are subsequently analyzed, only "a microorganism with a highest infective dose (probably the major infecting microorganism)" can be identified.

The primers are as follows.

<Combination Group 1>

(1-1) Five regions are selected from sequence regions common to the 16S rRNA genes of all bacteria to set forward primers and reverse primers (4 amplification products).

Specifically, the primers are primers each containing all or ⅓ or more of each of the base sequences of the following primers.

(B1) A primer set for amplifying 97-base DNA corresponding to nucleotides 809 to 905 of the 16S rRNA gene of E. coli (bacteria primer 1: Bac. 1).

```
                                     SEQ ID NO: 80
GATTAGATACCCTGGTAGTCCACG. (24mer) forward SEQ ID NO: 2
CCCGTCAATTCCTTTGAGTTT. (21mer) reverse
```

(B2) A primer set for amplifying 166-base DNA corresponding to nucleotides 927 to 1092 of the 16S rRNA gene of E. coli (bacteria primer 2: Bac. 2).

```
                                     SEQ ID NO: 3
AAACTCAAAGGAATTGACGGG. (21mer) forward SEQ ID NO: 4
CGCTCGTTGCGGGAC. (15mer) reverse
```

(B3) A primer set for amplifying 111-base DNA corresponding to nucleotides 1108 to 1218 of the 16S rRNA gene of E. coli (bacteria primer 3: Bac. 3).

```
                                     SEQ ID NO: 5
GTCCCGCAACGAGCG. (15mer) forward SEQ ID NO: 6
ATTGTAGCACGTGTGTAGCCC. (21mer) reverse
```

(B4) A primer set for amplifying 130-base DNA corresponding to nucleotides 1240 to 1369 of the 16S rRNA gene of E. coli (bacteria primer 4: Bac. 4).

```
                                     SEQ ID NO: 7
GGGCTACACACGTGCTACAAT. (21 mer) forward SEQ ID NO: 8
CCGGGAACGTATTCACC. (17mer) reverse
```

(1-2) Sequence regions common to the 18S rRNA genes of all fungi are selected and a pair of a forward primer and a reverse primer derived therefrom is set.

Specifically, the primers are primers each containing all or ⅓ or more of each of the base sequences of the following primers.

(F-1) A primer set for the 18S rRNA gene of fungi (fungi primer: Fungi).

```
                                       SEQ ID NO: 9
GAATGAGTACAATGTAAATACCTTAACG. (28mer) forward SEQ ID NO: 10
TAACTGCAACAACTTTAATATACGC. (25mer) reverse
```

(1-3) Primers for a mec A gene exhibiting methicillin resistance are set by selecting a most highly scored primer design using Light Cycler Probe Design 2 Software.

Specifically, the primers are as follows.

(M1) A primer set for the mec A gene exhibiting methicillin resistance (mec A primer: mecA)

```
                                       SEQ ID NO: 13
ATTATAAAGCAATCGCTAAAGAACTAAGTA. (30mer) forward SEQ ID NO: 14
CCAATAACTGCATCATCTTTATAGCC. (26mer) reverse
```

<Combination Group 2>

(2-1) Ten regions are selected from sequence regions common to the 16S rRNA genes of all bacteria to set forward primers and reverse primers.

Specifically, the primers are primers each containing all or ⅓ or more of each of the base sequences of the following primers.

(B5) A primer set for amplifying 338-base DNA corresponding to nucleotides 8 to 345 of the 16S rRNA gene of E. coli (bacteria primer 5: Bac. 5).

```
                                     SEQ ID NO: 15
AGAGTTTGATCATGGCTCAG. (20mer) forward SEQ ID NO: 16
CGTAGGAGTCTGGACCGT. (18mer) reverse
```

(B6) A primer set for amplifying 199-base DNA corresponding to nucleotides 336 to 534 of the 16S rRNA gene of E. coli (bacteria primer 6: Bac. 6).

```
                                     SEQ ID NO: 17
GACTCCTACGGGAGGCA. (17 mer) forward SEQ ID NO: 18
TATTACCGCGGCTGCTG. (17 mer) reverse
```

(B7) A primer set for amplifying 287-base DNA corresponding to nucleotides 519 to 805 of the 16S rRNA gene of E. coli (bacteria primer 7: Bac. 7).

```
                                           SEQ ID NO: 19
AGCAGCCGCGGTAATA. (16 mer) forward SEQ ID NO: 20
GGACTACCAGGGTATCTAATCCT. (23 mer) reverse
```

(B8) A primer set for amplifying 181-base DNA corresponding to nucleotides 780 to 960 of the 16S rRNA gene of E. coli (bacteria primer 8: Bac. 8).

```
                                           SEQ ID NO: 21
AACAGGATTAGATACCCTGGTAG. (23 mer) forward SEQ ID NO: 22
AATTAAACCACATGCTCCACC. (21 mer) reverse
```

(B9) A primer set for amplifying 120-base DNA corresponding to nucleotides 951 to 1,070 of the 16S rRNA gene of E. coli (bacteria primer 9: Bac. 9).

```
                                           SEQ ID NO: 23
TGGTTTAATTCGATGCAACGC. (21 mer) forward SEQ ID NO: 24
GAGCTGACGACAGCCAT. (17 mer) reverse
```

(B10) A primer set for amplifying 109-base DNA corresponding to nucleotides 1,084 to 1,192 of the 16S rRNA gene of E. coli (bacteria primer 10: Bac. 10).

```
                                           SEQ ID NO: 25
TTGGGTTAAGTCCCGC. (16 mer) forward SEQ ID NO: 26
CGTCATCCCCACCTTC. (16 mer) reverse
```

(B11) A primer set for amplifying 166-base DNA corresponding to nucleotides 1,220 to 1,385 of the 16S rRNA gene of E. coli (bacteria primer 11: Bac. 11).

```
                                           SEQ ID NO: 27
GGCTACACACGTGCTACAAT. (20 mer) forward SEQ ID NO: 28
CCGGGAACGTATTCACC. (17 mer) reverse
```

(2-2) Seven regions are selected from sequence regions common to the 18S rRNA gene of fungi to set forward primers and reverse primers.

Specifically, the primers are primers each containing all or ⅓ or more of each of the base sequences of the following primers.

(F2) A primer set for amplifying 259-base DNA corresponding to nucleotides 149 to 407 of the 18S rRNA gene (SEQ ID NO: 16) of C. Albicans (fungi primer 2: Fungi 2).

```
                                           SEQ ID NO: 29
GTGGTAATTCTAGAGCTAATACATGC. (26 mer) forward SEQ ID NO: 30
GGTAGCCGTTTCTCAGG. (17 mer) reverse
```

(F3) A primer set for amplifying 162-base DNA corresponding to nucleotides 390 to 551 of the 18S rRNA gene of C. Albicans (fungi primer 3: Fungi 3).

```
                                           SEQ ID NO: 31
GCCTGAGAAACGGCTACCA. (19 mer) forward SEQ ID NO: 32
CCTCCAATTGTTCCTCGTTAAG. (22 mer) reverse
```

(F4) A primer set for amplifying 232-base DNA corresponding to nucleotides 531 to 762 of the 18S rRNA gene of C. Albicans (fungi primer 4: Fungi 4).

```
                                           SEQ ID NO: 33
TTAACGAGGAACAATTGGAGGG. (22 mer) forward SEQ ID NO: 34
GCCTGCTTTGAACACTCTAATTT. (23 mer) reverse
```

(F5) A primer set for amplifying 146-base DNA corresponding to nucleotides 989 to 1,134 of the 18S rRNA gene of C. Albicans (fungi primer 5: Fungi 5).

```
                                           SEQ ID NO: 35
ATACCGTCGTAGTCTTAACCA. (21 mer) forward SEQ ID NO: 36
GTCAATTCCTTTAAGTTTCAGCCT. (24 mer) reverse
```

(F6) A primer set for amplifying 169-base DNA corresponding to nucleotides 1,260 to 1,428 of the 18S rRNA gene of C. Albicans (fungi primer 6: Fungi 6).

```
                                           SEQ ID NO: 37
CATGGCCGTTCTTAGTTGG. (19 mer) forward SEQ ID NO: 38
GGGCATCACAGACCTGTT. (18 mer) reverse
```

(F7) A primer set for amplifying 217-base DNA corresponding to nucleotides 1,414 to 1,630 of the 18S rRNA gene of C. Albicans (fungi primer 7: Fungi 7).

```
                                           SEQ ID NO: 39
AGGTCTGTGATGCCCTTAG. (19 mer) forward SEQ ID NO: 40
CGGGCGGTGTGTACAAA. (17 mer) reverse
```

(2-3) Primers for a mec A gene exhibiting methicillin resistance are set by selecting a most highly scored primer design using Light Cycler Probe Design 2 Software.

Specifically, the primers are as follows.

(M2) A primer set for the mec A gene exhibiting methicillin resistance (mec A primer 2: mecA2)

```
                                           SEQ ID NO: 43
CAAACTACGGTAACATTGATCGC. (23 mer) forward SEQ ID NO: 44
ATGTATGCTTTGGTCTTTCTGC. (22 mer) reverse
```

For the purpose of the present invention, the Tm value is a temperature at which the complementary strands of 50% of a PCR product dissociate. Based on the theoretical rationale that "the Tm value depends on the base sequence" for the calculation formula using a nearest neighbor method, the difference in the base sequence among strains can be applied as a difference in the combination of Tm values to the identification of a causative agent. Thus, it is most important for accurate identification to "eliminate the influence of measurement error from the Tm value". Therefore, the influence of measurement error is eliminated by the following method.

Because the Tm value varies under experimental conditions in which the composition of a buffer solution or the like is different, SYBR Green I, in which the magnesium chloride concentration is fixed, is first used as a buffer solution for reaction so that the measurement error due to the composition of a reaction solution does not occur. Then, because a real-time PCR device itself causes measurement error in each measurement cycle, a reference Tm value is set as control, and the differential pattern between the Tm values obtained in the same measurement cycle is utilized for the determination. Alternatively, the identification algorithm in which "the organism having the approximation of the combination of "the values relative to the average value" is a subject organism to be detected" is used.

According to the present invention, a standard Tm value as the reference can be used to correct the error between measurement cycles of a measurement device. Specifically, using a constant concentration of DNA of a standard strain of E. coli as a template, one primer set for amplifying one region of the 16S rRNA gene of a bacterium is used to measure the Tm value in each cycle to correct the deviation of a Tm value in each measurement cycle. Thus, if the same primer is combined with the same template, the Tm value will be theoretically the same in every cycle.

However, when the Tm value actually obtained deviates, the deviation provides an error between the measurements, and, thus, the error may be corrected by a deviation in such case.

The specific procedures of the methods (A) and (B) of the present invention are as follows:

(i) DNA is prepared from a sample;

(ii) the resultant DNA is subjected gene amplification using the aforementioned primer sets for bacteria, an antibiotic resistance gene, and fungi to measure the respective Tm values at a time to provide a combination of the Tm values for the bacteria, the antibiotic resistance gene, and the fungi.

(iii) it is determined whether the DNA is derived from a fungus [in the combination of the Tm values in (ii), the Tm value specific for fungi thus obtained, using a primer set capable of amplifying one or more regions of the 18S rRNA gene of all fungi is first analyzed to determine whether the DNA is derived from a fungus or what is the type of the fungus.];

(iv) the presence of the antibiotic resistance gene is determined [in the combination of the Tm values in (ii), the gene amplification specific to an antibiotic resistant bacterium thus obtained, using a primer set specifically amplifying an antibiotic resistance gene reflecting an spreaded epidemic of the current time such as a mec A gene exhibiting methicillin resistance is analyzed to determine the presence of the antibiotic resistance gene]; and (v) the range of the bacterial species as the candidates is narrowed. [in the combination of the Tm values in (ii), the combination of the Tm values specific for fungi thus obtained, using a primer set capable of amplifying a plurality of regions of the 16S rRNA genes of all bacteria is analyzed to identify the species of the bacterium].

Specifically, one of the Tm values specific to bacteria is selected (the Tm value may be corrected using the reference Tm value). The range of the bacterial species as the candidates is narrowed to bacterial species having a value close to the Tm value. The difference in the Tm values is sequentially calculated to narrow the range, or the difference in the Tm values including the reference Tm value is directly calculated, and the bacterial species is identified using the combination of the differences as a fingerprint. Alternatively, the identification algorithm in which "the organism having the approximation of the combination of "the values relative to the average value" is a subject organism to be detected" is used.

As a method for rapidly and simply identifying whether the subject organism to be detected is a bacterium, a fungus, or antibiotic resistant, there is a method which comprises extracting DNA of an unknown bacterium without using the Tm value and, using the DNA as a template, performing PCR using the following [1] to [3], and the resultant amplification products are subjected to electrophoresis in agarose gel to determine the band with a desired size:

[1] one primer common to the 18S rRNA genes of all fungi and specifically detecting fungi and a thermostable DNA polymerase preparation produced using a bacterium as a host;

[2] each one primer specifically detecting an antibiotic resistance gene reflecting a spread epidemic of the current time such as a mec A gene exhibiting methicillin resistance and the thermostable DNA polymerase preparation according to the present invention or a thermostable DNA polymerase preparation produced using a bacterium as a host;

[3] one primer common to the 16S rRNA genes of all bacteria and specifically detecting bacteria and the thermostable DNA polymerase preparation according to the present invention.

According to the above method, the following effect can be obtained.

(1) Gene amplification such as real-time PCR based on 4 to 18, and preferably 4 to 16 primer sets can be performed, followed by compare the resulting Tm values with the database to identify the strain of a causative microorganism necessary for antimicrobial drug selection and determine the presence of the antibiotic resistance gene.

(2) In the case of a blood sample, since the time required for DNA extraction, Tm value analysis, and identification is about two hours, rapid diagnosis becomes possible.

(3) When the amount of blood sample, from which DNA is extracted, is constant, the relative bacterial amount can be quantified, which enables the monitoring of a therapeutic effect after administration of the antimicrobial drug.

(4) the thermostable DNA polymerase preparation produced using a bacterium as a host and the thermostable DNA polymerase preparation according to the present invention can be used properly to almost completely eliminate the risk of false positivity such as non-specific amplification.

In addition, the identification of a fungus is preferably performed based on the combination of the Tm values obtained using the combination of universal primers for topoisomerase II, mitochondrial DNA or 26S ribosomal RNA.

(Set for Quantification or Identification)

A set for quantifying and/or identifying a subject organism to be detected contained in a sample can be provided at least by the thermostable DNA polymerase preparation according to the present invention for amplifying the DNA prepared from a sample; and primers for amplifying an intended gene specific for a subject organism to be detected.

In addition, the set may comprise at least the thermostable DNA polymerase preparation of the present invention for amplifying DNA prepared from a sample a thermostable DNA polymerase preparation for amplifying DNA prepared from a sample, produced using bacterial cells as a host, and primers for amplifying an intended gene specific for a subject organism to be detected.

For these primers for the set, the aforementioned primers (B), (F) and (M) can be used.

(Quantification/Identification System)

The following devices may comprise a system for quantifying or identifying a subject organism to be detected contained in a sample by the above-described methods.

(1) An amplifier device for performing a nucleic acid amplification reaction using DNA prepared from a sample, primers for amplifying an intended gene specific for a subject organism to be detected, and a thermostable DNA polymerase preparation.

(2) A quantification device for quantifying an amplification product in an amplification step.

(3) A computer for calculating the amount of the subject organism to be detected in the sample from the quantification results of the amplification product.

(4) A database for calculating the amount of the subject organism to be detected in the sample from the quantification results of the amplification product of the intended gene.

For the amplifier and the quantification device, a PCR device, especially a real-time PCR device, can be suitably used. For the computer, a computer system can also be used which operates based on a preselected program for quantifying and/or identifying the subject organism to be detected using the database, for example.

An example of the system for quantifying and/or identifying a subject organism to be detected according to the present invention is described below. This system can include the following elements (units):

(1) a PCR reaction device;
(2) a computer system for processing data and outputting the results of the data processing;
(3) a data processing software in which a program necessary for the data processing is written;
(4) a database necessary for data processing;
(5) a control system having a program for controlling the PCR reaction device; and
(6) a display device for displaying the results of the data processing.

Figure 12:
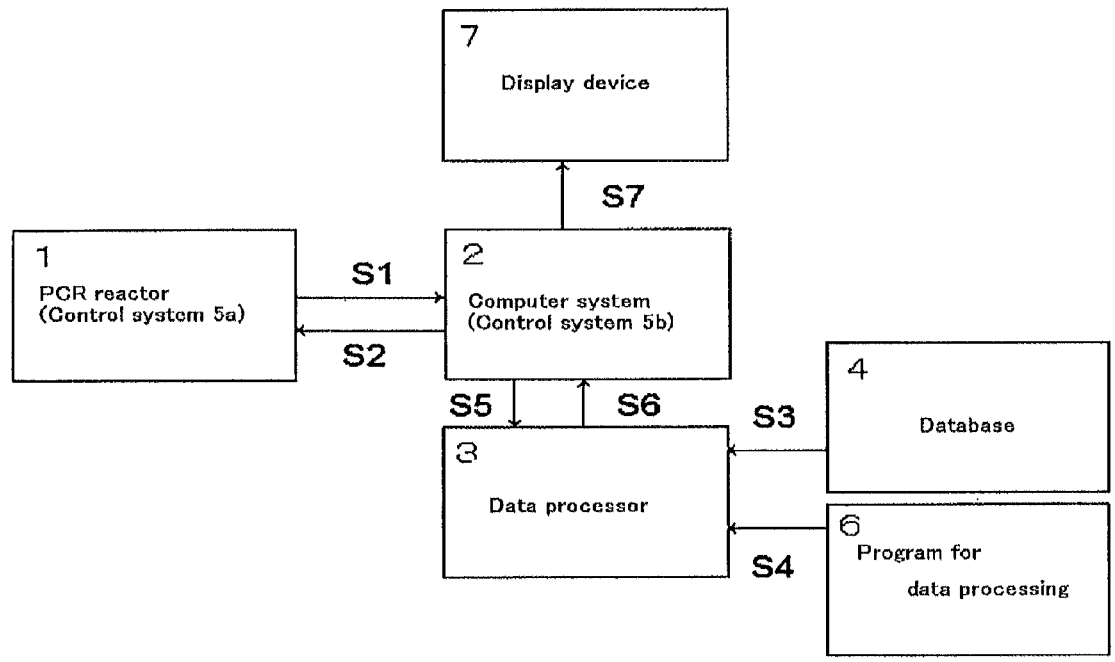
[FIG. 12]

An example of the relationship between these devices is shown in FIG. 12. This system includes a PCR reaction device 1, a computer system 2, a data processing section 3, a data processing program (software) 6, a database necessary for data processing 4, control systems for controlling the PCR reaction device 5a and 5b, and a display device 7. These may be provided by integrating two or more thereof. The sending and receiving of information between the units are performed by using signals S1 to S7. The quantification device can be constituted at least by the computer system 2.

In the PCR reaction device, the PCR reaction for quantifying and/or identifying a subject organism to be detected takes place. The control thereof can be performed using the control system 5. The following items can be listed as an example of the items of control in the control system 5:

A) condition setting at the start of an amplification reaction;
B) condition setting for the number of cycles for amplification and for temperature control;
C) condition setting for the measurement of the Tm value;
D) condition setting for the termination of reaction; and
E) condition setting for non-displaying the amplification of an unintended gene on the display device.

From these condition setting items, control items can be selected and set according to the particular object. The condition setting and the working of the conditions can be performed using a preselected program. This program can be recorded on a medium in the control system 5a or 5b. Alternatively, the program may be stored in a movable (portable) medium separately provided or accommodated in a medium so that it can be distributed using the Internet for enabling the use thereof by connection to the control system 5a or 5b at the time of use. When the PCR reaction device is controlled using the results of data processing in the data processing section 3 located in the computer system 2 or separately provided, the results of data processing from the data processing section 3 are sent to the computer system 2, and, based on the results, a signal for controlling the PCR reaction device is transmitted from the control system 5b to the control mechanism 5a in the PCR reaction device for the working of the control. When only the PCR reaction device-side control is enough according to the object of the PCR reaction, the PCR reaction is controlled using only the control system 5a.

The computer system 2 is programmed so that a signal from each unit can be processed according to the particular object. In the data processing section 2, the following processes are performed, for example:

i) the processing of the results of PCR amplification reaction (for example, a signal with fluorescent intensity) obtained in the PCR reaction device;

ii) arithmetic processing for quantifying and/or identifying a subject organism to be detected using the results of the PCR amplification reaction;

iii) the processing of a signal output for controlling PCR reaction conditions in the PCR reaction device; and iv) processing for commanding the display of the results of the PCR amplification reaction (including monitoring for a time course) and the results of the quantification and/or identification of the subject organism to be detected on a display device.

These processes are performed in accordance with the program 6 for data processing, which is set according to the desired data processing. In addition, when a database is necessary for data processing, the information stored in the database 4 is used. For example, the following data can be stored as a database:

Data obtained from the known organisms as the reference, when the signal obtained by the amplification reaction using PCR is processed to quantify and/or identify a subject organism to be detected.

Various Tm values (including various combinations of Tm values for quantification and/or identification from Tm values) obtained from known organisms, when the quantification and/or identification of subject organism to be measured is carried out using the previously described Tm value.

The data processing program 6 and the database 4 can be stored in a medium in the computer system 2. Alternatively, at least one of these may be stored in a movable (portable) medium separately provided or accommodated in a medium so that it can be distributed using the Internet for enabling the use thereof by connection to the data processing section 3 at the time of use.

EXAMPLES

Hereinafter, the present invention is described in detail with reference to Reference Example and Examples. However, the present invention is not limited to these Examples.

Furthermore unless otherwise specifically noted, the operation procedures were carried out based on the instructions attached to the product kits.

Example 1-1

(1) Synthesis of DNA

Complete DNA sequence of *T. aquatics*-derived thermostable DNA polymerase was synthesized at GenScript. At this time, the codon sequences were optimized for a yeast host, *S. cerevisiae*. The synthesized DNA was incorporated into a plasmid pUC57 provided from GenScript, and thus a vector pUC-TA01 was obtained. The gene encoding thermostable DNA polymerase was designed such that a HindIII restriction enzyme site was introduced into the 5' terminal sequence and an EcoRI restriction enzyme site was introduced into the 3' terminal sequence.

(2) Construction of Vector for Expressing *T. aquatics*-derived Thermostable DNA Polymerase The synthesized gene encoding *T. aquatics*-derived thermostable DNA polymerase was inserted into plasmid pYES2 (Invitrogen) so as to construct a vector pYES-TA01. For the gene encoding the thermostable DNA polymerase, the pUC-TA01 was digested with the restriction enzymes HindIII and EcoRI (TaKaRa Bio), which was subjected to electrophoresis with 1% agarose gel (Wako) and the gene encoding the thermostable DNA polymerase was recovered by using a QIAquick gel extraction kit (Qiagen). The plasmid pYES2 was digested with EcoRI and Hind III (TaKaRa Bio), and ligated to the gene encoding the thermostable DNA polymerase by using DNA Ligation Kit Ver.2.1 (TaKaRa Bio).

(3) Transformation of *S. cerevisiae*

The thus obtained vector pYES-TA01 was introduced into yeast (*Saccharomyces cerevisiae* X2180 strain). As a host, other yeast may be used as long as it is a uracil-requiring strain. Transformation was carried out by using FastTrack™-Yeast Transformation Kit (Geno Technology).

(4) Production of *T. aquatics*-derived Thermostable DNA Polymerase by *S. cerevisiae*

The obtained transformant was cultured with shaking in 100 ml of SD medium (0.67% Bacto yeast nitrogen base and 2% Galactose) at 28° C. for 72 hours. The culture was centrifuged at 5000 rpm for 10 min to collect cells which were suspended in a disruption buffer solution (50 mM Tris-HCl, pH7.5, 50 mM KCl), and the cells were disrupted by using 0.5 mm glass beads and then subjected to centrifugation at 12000 rpm for 30 min so as to obtain yeast homogenate supernatant and precipitate for cell extracts.

Figure 2:
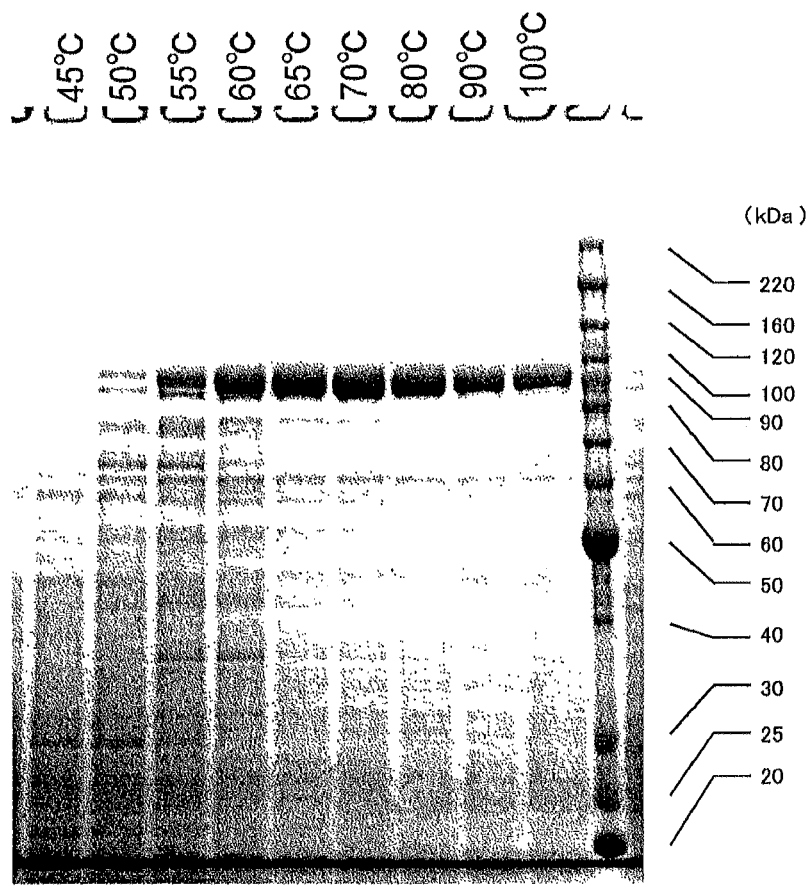
[FIG. 2]

(5) Study of Solubilization Conditions for Thermostable DNA Polymerase by Heat Treatment As to cell extracts, solubilization conditions of thermostable DNA polymerase by heat treatment were studied. FIG. 2 shows SDS-PAGE of a supernatant obtained after yeast homogenate precipitates were suspended in an equal amount of the disruption buffer solution, heat-treated at 45° C., 50° C., 55° C., 60° C., 65° C., 70° C., 75° C., 80° C., 85° C., 90° C., 95° C., and 100° C., and then centrifuged at 12000 rpm for 30 min at 4° C. When heat-treated at 50° C. or higher, a band of the thermostable DNA polymerase as a target protein was detected; when heat-treated at a temperature from 65° C. to 70° C., the amount of impurity protein derived from the host was reduced. After carrying out heat-treatment at 50° C. or higher, the thermostable DNA polymerase was found to be solubilized with a thermostable DNA polymerase activity.

(6) DNA Polymerase Activity (6-1) Amplification of Region in Lambda DNA Detection of activity was carried out by using lambda DNA (NIPPON GENE) as a template. The reaction solution was prepared so as to have a composition including 10 mM Tris-HCl (pH8.3), 1.5 mM of $MgCl_2$, 50 mM of KCl, and 200 μM of dNTPs. As the primers, SEQ ID NOs: 83 and 84 were added so that each was 0.4μM.

```
                                             SEQ ID NO: 83
          gatgagttcg tgtccgtaca act SEQ ID NO: 84
          ggttatcgaa atcagccaca gcgcc
```

The lambda DNA in the amount of 0.2 μg was added, and the thermostable DNA polymerase preparation in the amount of 1 μl was added after a dilution series was prepared so that the above-mentioned centrifuged supernatant became 1/4, 1/8, 1/16, 1/32, and 1/64, and they were prepared with ultrapure water so that the total amount became 50 μl. A PCR program was carried out by the following program: 94° C. for 1 min, 50° C. for 30 sec, and 72° C. for 1 min in one cycle, which was repeated 30 times. Each PCR reaction solution was subjected to electrophoresis with 1% agarose gel to visualize the amplification product.

(6-2) Definition of Thermostable DNA Polymerase Activity

The unit of the obtained thermostable DNA polymerase was determined according to the method described in Procedures in nucleic acid research (Richardson, C. C. (1966) DNA polymerase from *Escherichia coli*, pp. 263-276 In G. L. Cantoni and D. R. Davies (ed.)). Activated salmon sperm DNA was used as template/primer, an activity for taking 10 nmol of complete nucleotide into acid insoluble precipitates at 74° C. for 30 min in an activity measurement reaction solution (total amount of 50 μl containing 25 mM TAPS (pH9.3), 50 mM KCl, 2 mM $MgCl_2$, 1 mM β-mercaptoethanol, 200 μM each of dATP, dGTP, and dTTP, 100 μM [α-$^{32}$P]-dCTP (0.05-0.1 Ci/mmol), and 0.25 mg/ml activated salmon sperm DNA) was defined as 1 U.

(6-3) Detection Limit of PCR

Figure 3:
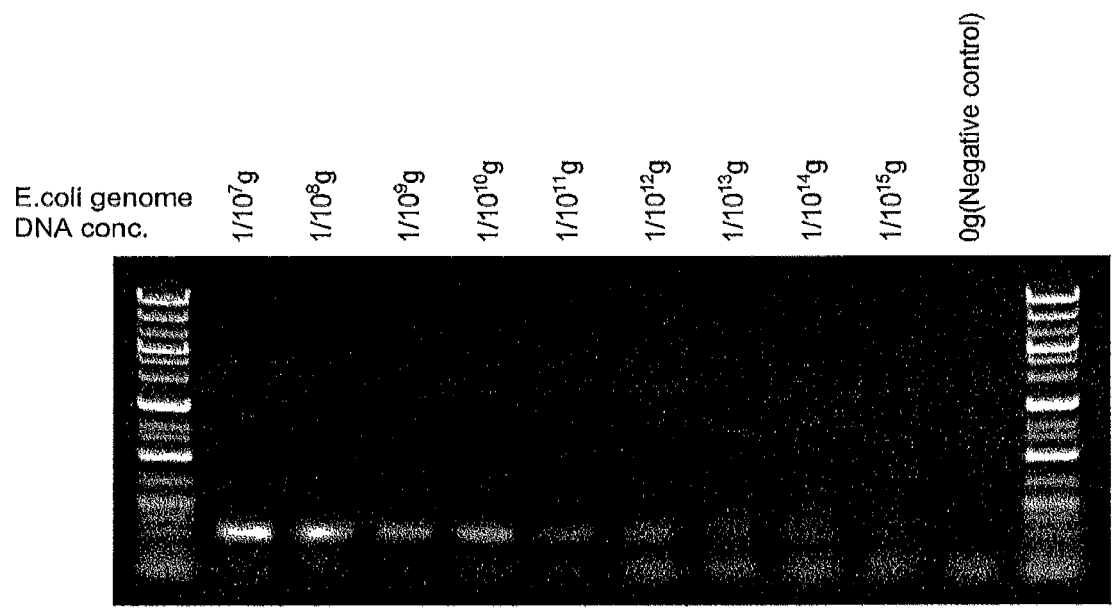
[FIG. 3]

FIG. 3 shows the detection limit of PCR using *Escherichia coli* DNA as a template. From 100 ng to 10 fg, a PCR amplification band was detected; from 10 fg to 1 fg, no amplification band was detected. *Escherichia coli* DNA was extracted and purified from *Escherichia coli* JM109 (manufactured by ToYoBo) by using DNA extraction kit FastPure DNA Kit (manufactured by TaKaRa). The reaction solution was prepared so as to have a composition including 10 mM Tris-HCl (pH8.3), 1.5 mM $MgCl_2$, 50 mM KCl, and 200 μM dNTPs. As primers, SEQ ID NOs: 85 and 86 were added so that each was 0.4μM.

```
                                             SEQ ID NO: 85
          agcagccgcg gtaat SEQ ID NO: 86
          ggactaccag ggtatctaat cct
```

As a template, *Escherichia coli* DNA dilution series including each $10^{-1}$ from 100 ng to 1 fg was formed and added. The 1 U of thermostable DNA polymerase preparation was added and prepared with ultrapure water so that the total amount was 20 μl. A PCR program was carried out by the following program: 94° C. for 1 min, 50° C. for 30 sec, and 72° C. for 30 sec as one cycle, which was repeated 60 times. Each PCR reaction solution was subjected to electrophoresis with 1% agarose gel to visualize the amplification product.

(7) Construction of Vector for Expressing *T. aquatics*-derived Thermostable DNA Polymerase A gene encoding *T. aquatics*-derived thermostable DNA polymerase was inserted into a plasmid pPIC ZA (Invitrogen) to construct a vector pPIC TA01. The gene encoding thermostable DNA polymerase was amplified by PCR using pYES-TA01 as a template and using KOD Plus (ToYoBo). Primers to be used for PCR (SEQ ID NOs: 87 and 88) were designed such that an EcoRI restriction enzyme site was introduced into the 5' terminal sequence and a NotI restriction enzyme site was introduced into the 3' terminal sequence.

```
          cccgaattca tgaggggat gttgccattg   SEQ ID NO: 87 aaagcggccg ctcattcctt tgcggataac   SEQ ID NO: 88
```

PCR program was carried out by the following program: heating at 94° C. for 2 min, then 94° C. for 15 sec, 56° C. for 30 sec, and 68° C. for 2 min and 30 sec as one cycle, which was repeated 30 times. The PCR product was then subjected to electrophoresis with 1% agarose gel, and PCR fragments were collected by using QIAquick gel extraction kit (Qiagen). The PCR amplification product and pPICZA were both digested with EcoRI and NotI (TaKaRa Bio), and the PCR amplification fragment was ligated to provide the plasmid pPICZ A by using DNA Ligation Kit Ver. 2.1 (TaKaRa Bio).

(8) Transformation of *E. coli* and Extraction of Vector

The ligated vector was introduced into *E. coli* competent cell DH5α (ToYoBo). Since the *Escherichia coli* transformant requires Zeocin as a selection marker, it was seeded onto a Lenox (Difco) agar medium containing 25 μl/ml Zeocin (Invitrogen) after recovering in an SOC (ToYoBo) medium for one hour and stationary-cultured at 37° C. for 16 hours. An *Escherichia coli* colony from the agar plate was inoculated and used for direct colony PCR, and the base sequence was read so as to confirm that the thermostable DNA polymerase gene was incorporated correctly. Thus the vector pPIC-TA01 was obtained.

(9) Transformation of *P. pastoris*

The vector pYES-TA01 was introduced into yeast (*Pichia pastoris* GS115 strain). Transformation was carried out by using FastTrack™-Yeast Transformation Kit (Geno Technology). Since the yeast transformant requires Zeocin as a selection marker, it was seeded onto a YPDS (Difco) agar plate containing 100 μl/ml Zeocin after recovering in YPD medium (Difco) for three hours. Then, the agar plate was stationary-cultured at 28° C. for three days.

(10) Selection of Transformant

In order to obtain a thermostable DNA polymerase high production strain, a transformed colony from the agar plate was inoculated and cultured on a YPDS (Difco) agar plate whose concentration of the Zeocin contained was sequentially raised from 500 μg/ml to 2000 μg/ml, followed by selecting transformants with multi-copy of the inserted gene. They were cultured on agar plates at three-staged Zeocin concentrations: 500 μg/ml, 1000 μg/ml, and 2000 μg/ml, and each of them was stationary-cultured at 28° C. for three days. The transformant that had been grown in the YPDS (Difco) agar plate whose Zeocin concentration was 2000 μg/ml was used for the following thermostable DNA polymerase production experiment.

(11) Production of *T. aquatics*-derived Thermostable DNA Polymerase

The transformant was inoculated in 100 ml of BMGY medium, and was cultured with shaking at 28° C. for one day so as to increase the amount of cells. Then, in order to induce production of protein, 0.5% methanol was added and cultured at 28° C. for three days. They were centrifuged at 5000 rpm for 10 min to collect cells, which were suspended in a disruption buffer solution (50 mM Tris-HCl, pH7.5, 50 mM KCl) and the cells were disrupted by using 0.5 mm glass beads. Next, they were subjected to heat-treatment at 70° C. for 60 min, and subjected to centrifugation at 12000 rpm for 30 min, and a supernatant containing *T. aquatics*-derived thermostable DNA polymerase was obtained.

(12) Construction of Vector for Expressing *P. furiosus*-derived Thermostable DNA Polymerase A gene encoding the *P. furiosus*-derived thermostable DNA polymerase was inserted into the plasmid pYES2 to construct a vector pYES-PF01. The gene encoding thermostable DNA polymerase was synthesized by PCR using *P. furiosus* genome DNA (ATCC 43587D-5) as a template. Primers to be used for PCR (SEQ ID NOs: 89 and 90) were designed such that a KpnI restriction enzyme site was introduced into the 5' terminal sequence and a NotI restriction enzyme site was introduced into the 3' terminal sequence. The PCR was carried out by using KOD Plus.

```
ggggggtacca tgatttaga tgtggattac    SEQ ID NO: 89 cccgcggccg cctaggattt tttaatg       SEQ ID NO: 90
```

A PCR program was carried out by the following program: heating at 94° C. for 2 min, then 94° C. for 15 sec, 56° C. for 30 sec, and 68° C. for 2 min and 30 sec as one cycle, which was repeated 30 times. The PCR product was subjected to electrophoresis with 1% agarose gel, and PCR fragments were recovered by using QIAquick gel extraction kit. The PCR amplification product and pYES2 were both digested with KpnI and NotI, and the PCR amplified fragment was ligated to provide pYES2 by using DNA Ligation Kit Ver. 2.1.

The ligated vector was introduced into *E. coli* competent cell JM109 (ToYoBo). The *Escherichia coli* transformant was seeded onto an LB agar medium containing 50 μl/ml ampicillin, and stationary-cultured at 37° C. for 16 hours. The *Escherichia coli* colony from the agar plate was inoculated and used for direct colony PCR and the base sequence was read so as to confirm that the thermostable DNA polymerase gene was incorporated correctly. Thus, a vector pYES-PF01 was obtained.

(13) Construction of Vector for Expressing *T. gorgonarius*-derived Thermostable DNA Polymerase A gene encoding the *T. gorgonarius*-derived thermostable DNA polymerase was inserted into the plasmid pYES2 to construct a vector pYES-TG01. The gene encoding thermostable DNA polymerase was synthesized by PCR using *T. gorgonarius* genome DNA (ATCC 700654D) as a template. Primers used for PCR (SEQ ID NOs: 91 and 92) were designed such that a KpnI restriction enzyme site was introduced into the 5' terminal sequence and a NotI restriction enzyme site was introduced into the 3' terminal sequence. The PCR was carried out by using KOD Plus.

```
gggggtacca tgatcctcga tacagac       SEQ ID NO: 91 cccgcggccg ctcatgtctt aggttttag     SEQ ID NO: 92
```

A PCR program was carried out by the following program: heating at 94° C. for 2 min, then 94° C. for 15 sec, 60° C. for 30 sec, and 68° C. for 2 min and 30 sec as one cycle, which was repeated 30 times. The PCR product was subjected to electrophoresis with 1% agarose gel, and PCR fragments were collected by using QIAquick gel extraction kit. The PCR amplification product and pYES2 were both digested with KpnI and NotI, and the PCR amplification fragment was ligated to provide pYES2 by using DNA Ligation Kit Ver. 2.1.

The ligated vector was transformed into *E. coli* competent cell JM109. The *Escherichia coli* transformant was seeded onto an LB agar medium containing 50 μl/ml ampicillin. Then, the agar plate was stationary-cultured at 37° C. for 16 hours. The *Escherichia coli* colony from the agar plate was inoculated and used for direct colony PCR and the base sequence was read so as to confirm that the thermostable DNA polymerase gene was incorporated correctly. Thus, a vector pYES-TG01 was obtained.

(14) Transformation of Yeast

The thus obtained vector pYES-P F01 and pYES-TG01 were introduced into yeast (*Saccharomyces cerevisiae* X2180 strain). The transformation was carried out by using Fast-Track™-Yeast Transformation Kit.

(15) Production of *P. furiosus*-, *T. gorgonarius*-derived Thermostable DNA Polymerases The obtained transformant was cultured with shaking in 100 ml of SD medium (0.67% Bacto yeast nitrogen base and 2% Galactose) at 28° C. for 72 hours. They were centrifuged at 5000 rpm for 10 min to collect cells which were suspended in a disruption buffer solution (50 mM Tris-HCl, pH7.5, 50 mM KCl) and the cells were disrupted by using 0.5 mm glass beads, and then subjected to centrifugation to obtain yeast homogenate precipitates. To the precipitates, the disruption buffer solution in the amount two times as the wet weight of the precipitates was added and suspended. The suspension was heat-treated at 70° C. for 60 min and centrifuged at 12000 rpm for 30 min to obtain a supernatant containing the thermostable DNA polymerase.

(16) Examination of Contamination of Non-Specific Nucleic Acid by PCR

Figure 4:
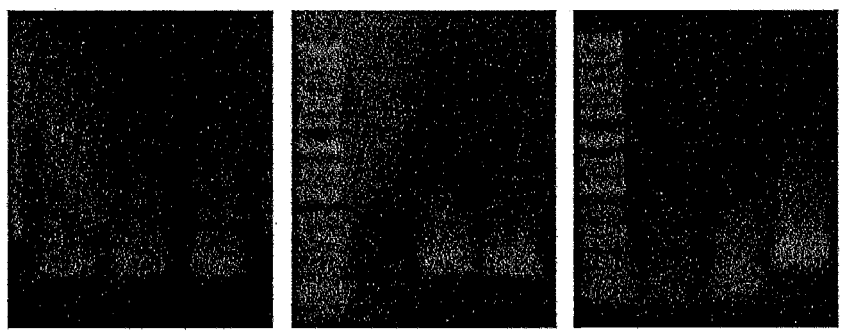
[FIG. 4]
Figure 4:
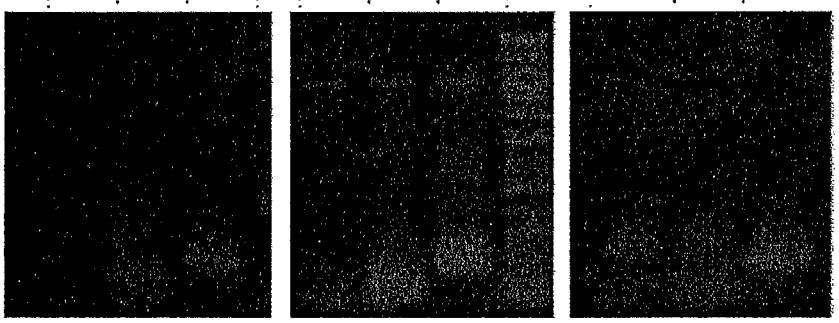

FIG. 4 is a photograph of 1% agarose electrophoresis showing examples of investigating whether contamination of non-specific nucleic acid is observed by using each of the above-obtained thermostable DNA polymerase preparations, TaKaRa Taq (TaKaRa) and AmpliTaq Gold LD (ABI). The lanes 1, 4, 7, 10, 13, and 16 show the results of 40 cycles of PCR without adding a template, as well as the lanes 2, 5, 8, 11, 14, and 17 show the results of 60 cycles of PCR without adding a template. Furthermore, the lanes 3, 6, 9, 12, 15, and 18 show the results of 30 cycles of PCR using 1 µg of *Escherichia coli* as a template. The procedure was carried out by using SEQ ID NOs: 85 and 86 capable of amplifying 259 bp *Escherichia coli* 16S rRNA gene as primers in the same temperature conditions and PCR solution compositions as those in (6-3). As a result, although a template was not added, an amplification product of bacterial 16S rRNA-derived gene was detected in 40 cycles with TaKaRa Taq and in 60 cycles with AmpliTaq Gold LD. Furthermore, in the thermostable DNA polymerase produced by the production method of the present invention, no amplification product was detected even in 40 cycles and 60 cycles of PCR, and the contamination of non-specific nucleic acid was not observed and PCR was able to be carried out without carrying out complicated purification process.

(17) Analyses of Amplification Curve and Melting Curve by Real-time PCR (Investigation of Contamination of Non-specific Nucleic Acid)

Figure 5:
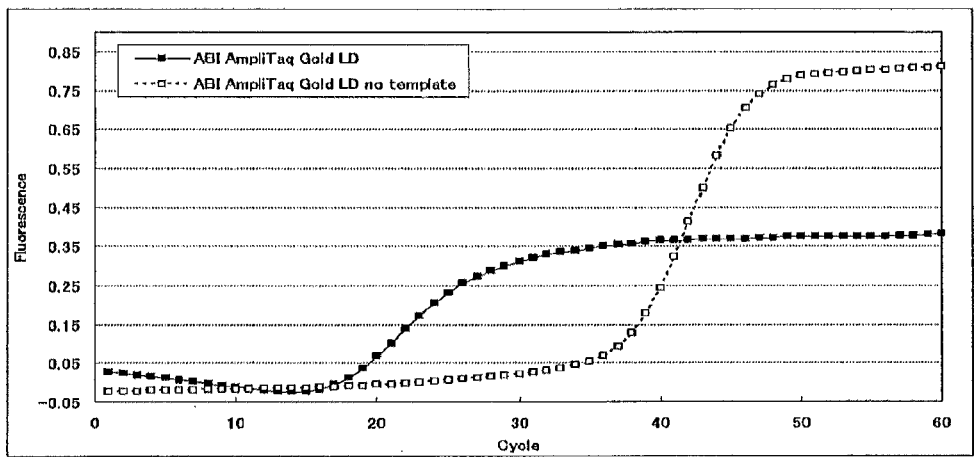
[FIG. 5]
Figure 5:
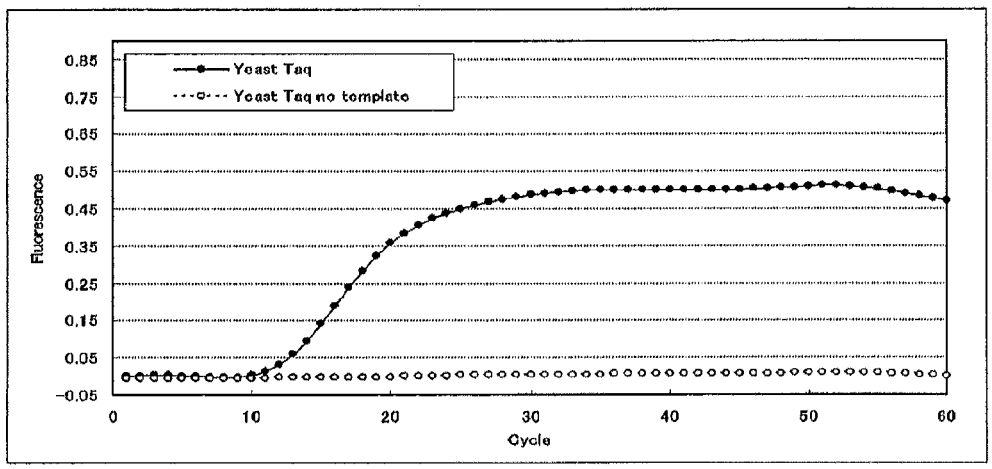
Figure 6:
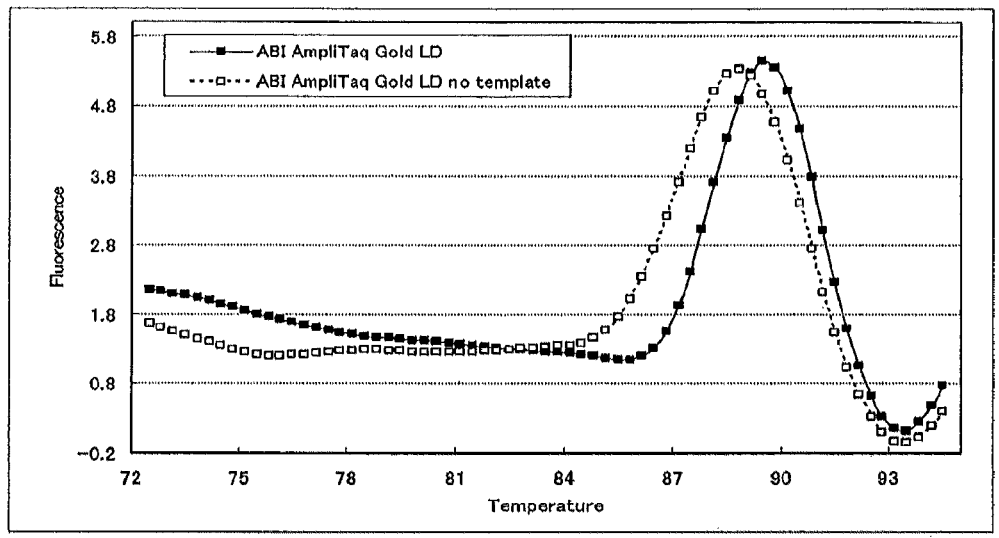
[FIG. 6]
Figure 6:
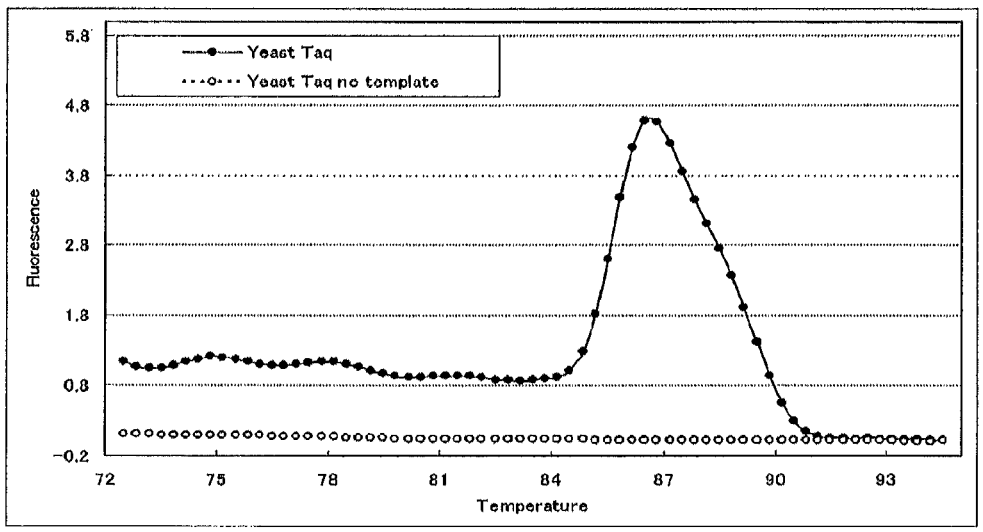

In order to investigate contamination of non-specific nucleic acid in the above-mentioned thermostable DNA polymerase preparations, analyses of an amplification curve and a melting curve were carried out by using real-time PCR. FIGS. 5(A) and FIG. 5(B) show analysis of amplification curves. FIGS. 6(A) and FIG. 6(B) show analysis of melting curves. Furthermore, FIG. 5(A) and FIG. 6(A) are graphs showing analysis carried out by using thermostable DNA polymerase preparation produced by using AmpliTaq Gold LD as a host. FIG. 5(B) and FIG. 6(B) are graphs showing analysis carried out by using thermostable DNA polymerase preparation produced by using *S. cerevisiae* as a host. Solid lines show a case in which *Escherichia coli* was added as a template, and broken lines show a case in which a template was not added. As the real-time PCR reagent, ×10 Buffer was obtained by adding 10 µl of ultrapure water into a 1b tube of LightCycler FastStart DNA Master SYBR GreenI (Roche). In this tube, dNTPs and SYBR GreenI in addition to a buffer reagent optimized for the Taq DNA polymerase are contained. Besides, 1.5 mM MgCl$_2$, 0.4 µM each of the primers (SEQ ID NOs: 85 and 86), 1 µg of *Escherichia coli* as a template, and 1 unit of thermostable DNA polymerase preparation were added, and ultrapure water were added so that the total amount was 20 µl, and thus real-time PCR (60 cycles) was carried out by a hot-start method. In the case of using AmpliTaq Gold LD, an amplification curve started to rise about 32 cycles, a melting curve had peaks in the substantially same positions in the case where the template was added and in the case where the template was not added, and contamination of non-specific nucleic acid was observed. On the contrary, in the thermostable DNA polymerase produced by the production method by the present invention, when the template was not added, the contamination was not observed both in the amplification curve and the melting curve. Regarding the thermostable DNA polymerase preparation produced by using an eukaryotic cell as a host, the amplification product derived from the contamination of non-specific nucleic acid was not observed. Regarding the thermostable DNA polymerase preparation produced by using bacteria as a host and purified so that the contamination of bacterial DNA was minimized, the amplification product derived from the contamination of non-specific nucleic acid was observed. From the results, in the probability of contamination of various non-specific nucleic acids such as contamination of bacteria present in the air or water environment, the main factor thereof was thought to be contamination into thermostable DNA polymerase preparations of host-derived DNA during the production process of thermostable DNA polymerase.

(18) Introduction of Mutation of Vector pYES-PF01

Mutation was introduced into a gene encoding the 3'-5' exonuclease of *P. furiosus*-derived thermostable DNA polymerase. Thus, the activity was adjusted by modifying the 3'-5' exonuclease of the DNA polymerase (Kong et al. (1993), journal of biological chemistry, vol. 268, 1965-1975). Specifically, PCR was carried out by using the primers (SEQ ID NOs: 61 and 62) to be used for introduction of mutation, and vectors pYES2-PF01 as a template and using KOD Plus.

SEQ ID NO: 61
GATTCTTGCCTTCGCGATCGCAACCCTCTATCACGAAGG

SEQ ID NO: 62
CCTTCGTGATAGAGGGTTGCGATCGCGAAGGCAAGAATC

A PCR program was carried out by the following program: heating at 94° C. for 2 min, then 94° C. for 15 sec, 56° C. for 30 sec, and 68° C. for 7 min as one cycle, which was repeated 15 times. After reaction, the template in the PCR solution was digested with a restriction enzyme DpnI, and introduced into *E. coli* competent cell JM109. The *Escherichia coli* transformant was seeded onto an LB agar medium containing 50 µl/ml of ampicillin, and stationary-cultured at 37° C. for 16 hours. The *Escherichia coli* colony from the agar plate was inoculated, followed by decoding the base sequence to confirm that the mutation was introduced in the target position. Thus, a vector pYES-PF-M01 was obtained. Furthermore, transformation and production were carried out similar to Examples (14) and (15), and *P. furiosus*-derived mutated thermostable DNA polymerase preparation was obtained.

(19) Introduction of Mutation of Vector pYES-TG01

Mutation was introduced into a gene encoding the 3'-5' exonuclease of *T. gorgonarius*-derived thermostable DNA polymerase. The mutation was introduced by the same method as in the (18) by using the primers (SEQ ID NOs 63 and 64) to be used for introducing mutation, and vector pYES2-TG01 as a template.

SEQ ID NO: 63
GATGCTCGCCTTCGCGATCGCAACGCTCTATCACGAGGGCG

SEQ ID NO: 64
CGCCCTCGTGATAGAGCGTTGCGATCGCGAAGGCGAGCATC

The base sequence was read to confirm that the mutation was introduced in the target position, and thus a vector pYES-TG-M01 was obtained. Furthermore, transformation and production were carried out similar to Examples (14) and (15), and *T. gorgonarius*-derived mutated thermostable DNA polymerase preparation was obtained.

(20) Production of *T. aquaticus*-derived Thermostable DNA Polymerase by Using Host Tobacco-BY2

(20-1) Construction of Vector for Introducing Transcription Factor Expression DNA Fragment As a vector for introducing a transcription factor expression DNA fragment into a host cell (tobacco BY2 cell) (hereinafter, referred to as a "transcription factor expression DNA fragment introducing vector"), a Ti plasmid pER8 (-Stu) (Dohi, K., Nishikiori, M., Tamai, A., Ishikawa, M., Meshi, T., and Mori, T. (2006), Inducible virus-mediated expression of a foreign protein in suspension-cultured cells. Archives of Virology 151, 1075-1084) was used. The pER8 (-Stu) was constructed by linking a gene encoding a fusion transcription factor LexA-VP16-hER containing an estrogen receptor and a terminator TE9 to the downstream of a constitutive promoter PG10-90 and incorporating a hygromycin-resistant gene (Hygr) as a drug-resistant marker.

(20-2) Construction of Protein Expression DNA Fragment Introducing Vector

A ToMV variant in which a gene encoding the envelope of ToMV was substituted with a gene encoding *T. aquaticus*-derived DNA polymerase (SEQ ID NO: 65) was used.

```
                                          SEQ ID NO: 65
ATGAGGGGGATGTTGCCATTGTTTGAACCTAAAGGGAGGGTTTTACTCG

TGGATGGCCATCACCTTGCTTATCGTACTTTCCACGCTCTCAAAGGTTTA

ACAACCTCTAGGGGAGAGCCAGTTCAAGCTGTGTACGGGTTTGCAAAG

TCACTCCTTAAAGCCTTGAAGGAGGACGGTGATGCCGTTATCGTGGTAT

TCGATGCTAAAGCACCAAGTTTTAGACACGAGGCTTACGGAGGCTATAA

GGCTGGACGTGCACCAACTCCCGAGGATTTCCCAAGACAACTCGCCCT

GATAAAGGAGTTGGTTGACCTACTTGGATTGGCTAGGTTAGAAGTTCCC

GGTTACGAAGCTGACGACGTTTTGGCCTCACTTGCTAAGAAAGCAGAAA

AGGAGGGCTACGAAGTTCGTATACTCACAGCCGATAAAGACTTGTATCA

ACTGTTATCTGATAGGATTCATGTGCTTCACCCCGAAGGGTACCTTATCA

CCCCTGCCTGGCTGTGGGAAAAGTACGGGCTCAGACCTGACCAGTGGG

CTGATTACCGTGCACTCACCGGTGACGAGAGTGACAATCTTCCTGGCGT

GAAAGGAATAGGTGAAAAGACAGCTAGAAAATTGCTAGAAGAGTGGGG

GTCCCTCGAGGCACTTTTGAAGAACCTTGATAGGTTAAAACCAGCTATT

AGAGAAAAGATACTGGCCCATATGGATGACTTGAAACTATCATGGGACT

TAGCTAAAGTCAGAACCGATTTACCTTTGGAAGTGGATTTTGCTAAGAGA

AGGGAACCAGATAGAGAGAGGCTTAGAGCATTCTTGGAGCGTCTGGAA

TTTGGATCTTTACTCCACGAGTTCGGTTTGCTTGAGTCTCCCAAGGCAC

TGGAAGAGGCACCATGGCCTCCACCTGAAGGCGCTTTTGTTGGGTTCG

TTCTCAGTAGGAAGGAACCTATGTGGGCAGACTTGCTCGCCCTAGCAG

CTGCAAGAGGGGAAGAGTGCATAGGGCTCCCGAACCTTATAAGGCAC

TCAGAGATCTTAAGGAGGCTAGGGGCCTCTTGGCAAAGGACCTATCCG

TGCTTGCACTCAGGGAAGGATTGGGACTCCCACCCGGTGATGACCCTA

TGTTATTGGCTTACTTGCTTGACCCATCCAATACCACACCCGAGGGAGT
```

```
                    -continued
TGCCCGTAGGTATGGGGGCGAGTGGACTGAGGAAGCTGGTGAGAGGG

CCGCATTGAGTGAGAGGCTATTTGCCAACTTATGGGGGAGGTTGGAGG

GGGAGGAACGTCTGCTATGGCTTTACAGAGAGGTGGAGCGTCCCTTGA

GTGCTGTATTAGCTCACATGGAAGCTACAGGCGTCCGTCTAGATGTTGC

TTACTTAAGGGCTCTAAGTTTGGAAGTTGCAGAAGAGATCGCCAGATTA

GAAGCTGAAGTTTTCAGGTTAGCAGGACACCCTTTTAATCTCAATAGTAG

GGACCAACTCGAACGTGTGTTATTTGATGAACTGGGCCTCCCCGCTATA

GGGAAAACCGAGAAAACAGGGAAAAGGTCCACATCTGCAGCTGTATTG

GAAGCCCTTAGAGAAGCACATCCTATTGTGGAGAAAATACTACAGTACA

GGGAGCTAACCAAATTAAAGAGTACCTACATAGATCCATTGCCTGATCTT

ATTCACCCAAGGACCGGAAGGCTTCACACCCGTTTCAATCAAACCGCAA

CAGCTACTGGGAGGTTATCATCTTCCGACCCTAACTTGCAAAATATACCT

GTTCGTACCCCACTCGGACAGAGAATACGTAGAGCTTTCATTGCCGAAG

AGGGATGGCTCTTGGTTGCTTTGGATTATAGTCAGATTGAACTTAGAGTT

CTAGCACACCTTAGTGGCGACGAAAACCTCATCAGGGTGTTTCAGGAG

GGGAGAGATATACACACCGAAACTGCTTCATGGATGTTTGGGGTGCCC

AGGGAAGCCGTAGACCCCCTCATGAGAAGGGCTGCTAAAACAATTAATT

TCGGCGTGTTGTACGGAATGTCCGCTCACAGGCTATCACAAGAGTTGG

CAATCCCCTATGAAGAGGCTCAAGCCTTCATTGAGAGGTATTTTCAGTC

CTTTCCAAAGGTGCGTGCTTGGATAGAGAAAACTTTAGAGGAAGGTAGA

AGGAGAGGGTATGTGGAAACTCTATTTGGCAGACGTAGGTACGTTCCTG

ACCTCGAAGCTAGAGTTAAGTCCGTCAGAGAGGCAGCTGAACGTATGG

CATTCAATATGCCTGTTCAAGGAACAGCTGCAGACTTAATGAAATTAGCT

ATGGTGAAGTTGTTCCCAAGGTTAGAGGAAATGGGTGCAAGAATGCTCC

TACAGGTCCATGATGAGCTAGTGTTGGAAGCACCTAAAGAGAGGGCAG

AGGCAGTAGCCAGGTTGGCAAAGGAGGTTATGGAAGGGGTGTATCCAC

TTGCTGTCCCCTTGGAGGTGGAAGTCGGGATCGGTGAGGACTGGTTAT

CCGCAAAGGAATGAGCTCACTAGT
```

The complete gene sequence of *T. aquatics*-derived thermostable DNA polymerase was synthesized at GenScript. At this time, the codon sequences were optimized for a tobacco BY2 cell. As a vector for transformation, the vector pBICER8-ToMV/Taq-SRz for introducing a protein expression DNA fragment into a host cell (tobacco BY2 cell) was constructed by using a Ti plasmid having an estrogen-inducible promoter $O_{LexA}$-46, linking cDNA of a ToMV variant to the downstream of the $O_{LexA}$-46, and incorporating the ribozyme sequence S-Rz of satellite tobacco ring spot virus and 35S terminator (35ST) at its 3' terminus.

(20-3) First Transformation Step: Introduction of Transcription Factor Expression DNA Fragment into Host Cell A vector pER8(-Stu) for introducing a transcription factor expression DNA fragment was introduced into tobacco BY2 cell by an *Agrobacterium* method. Firstly, pER8(-Stu) was introduced into *Agrobacterium tumefacince* LBA4404 cell line by electroporation. This was pre-cultured in an AB sucrose medium containing spectinomycin (50 mg/l). Next, this was mixed with tobacco BY2 cells and transferred to a petri dish, and stood still in dark at 26° C. for 42 to 48 hours so as to transform tobacco BY2 cells. The transformant was washed in a medium for the tobacco BY2 cells, and then developed on a solid medium for tobacco BY2 cell containing carbenicillin (100 mg/l) and hygromycin (20 mg/l) so as to proliferate transformed tobacco BY2 cells.

(20-4) Selection Step: Selection of Transcription Factor High Expression Transformant Among the transformation tobacco BY2 cells, a cell line having a high expression amount of the transcription factor was selected according to the results of northern blotting. The "cell line" herein denotes an individual colony formed by proliferating transformed cells.

(20-5) Second Transformation Step: Introduction of Protein Expression DNA Fragment To the above-obtained transcription factor high expression tobacco BY2 cell line, a virus vector (pBICER8-ToMV/Taq-SRz) was introduced by the *Agrobacterium* method to obtain transformation cells.

(20-6) Culture of Tobacco BY2 Cell, and Protein Expression and Extraction

The transformed cells obtained above were kept in 15 ml of liquid culture, and 1/200 amount of the culture was subcultured every seven days. In addition, 1/50 amount of the culture was subcultured, and to the 2 days-precultured cells estrogen was added at the final concentration of 0.01 mM, which was then cultured for further two days. This culture was centrifuged at 5000 rpm for 10 min, and transformed cells were collected, and frozen in liquid nitrogen. The cells were disrupted by using a mortar. To the disrupted cells, an equal amount of buffer solution (50 mM Tris-HCl, pH7.5, 50 mM KCl) was added and suspended, and the suspension was heat-treated at 70° C. for 60 min, centrifuged at 12000 rpm for 30 min to obtain a supernatant containing *T. aquatics*-derived thermostable DNA polymerase.

(21) Expression of *T. Aqaticus* Derived Thermostable DNA Polymerase Using Host *A. oryzae*

(21-1) Synthesis of DNA

The whole DNA sequence of *T. aquatics*-derived thermostable DNA polymerase was synthesized at GenScript (SEQ ID NO: 41). At this time, the codon sequences were optimized for *A. oryzae*. A gene encoding the thermostable DNA polymerase was designed such that a PmeI restriction enzyme site was introduced into the 5' terminal sequence and an XmaI restriction enzyme site was introduced into the 3' terminal sequence.

SEQ ID NO: 41
ATGAGAGGCATGCTGCCACTGTTCGAGCCAAAGGGAAGGGTGCTGCTG

GTGGACGGACACCATCTGGCCTACAGAACTTTTCACGCTCTGAAGGGA

CTGACCACATCACGGGGGGAGCCAGTGCAGGCTGTGTATGGATTCGCT

AAAAGCCTGCTGAAGGCCCTGAAAGAGGACGGAGATGCTGTGATCGTG

GTGTTCGATGCTAAGGCCCCTAGCTTTAGACATGAGGCCTACGGCGGA

TATAAAGCCGGACGCGCTCCAACCCCCGAGGACTTTTCCAAGGCAGCTG

GCCCTGATTAAGGAACTGGTGGATCTGCTGGGACTGGCTAGGCTGGAG

GTGCCCGGCTACGAAGCTGACGATGTGCTGGCCTCCCTGGCTAAGAAA

GCCGAGAAGGAAGGCTACGAGGTGCGCATCCTGACAGCCGACAAAGAT

CTGTATCAGCTGCTGTCTGACAGGATCCACGTGCTGCATCCCGAGGGG

TATCTGATTACTCCTGCCTGGCTGTGGGAAAAGTACGGCCTGAGACCA

-continued

GACCAGTGGGCTGATTATCGGGCCCTGACTGGCGACGAGTCAGATAAC

CTGCCCGGAGTGAAAGGCATCGGAGAAAAAACCGCCAGGAAGCTGCTG

GAGGAATGGGGCAGCCTGGAGGCTCTGCTGAAAAATCTGGATAGACTG

AAGCCCGCCATCCGGGAGAAAATTCTGGCTCACATGGACGATCTGAAG

CTGTCTTGGGACCTGGCCAAAGTGAGAACCGACCTGCCTCTGGAGGTG

GATTTCGCCAAGAGGAGAGAGCCAGATCGGGAACGCCTGAGGGCTTTC

CTGGAGCGGCTGGAATTTGGGTCACTGCTGCATGAGTTTGGCCTGCTG

GAAAGCCCAAAGGCTCTGGAGGAAGCTCCATGGCCACCTCCAGAGGGA

GCCTTCGTGGGATTTGTGCTGTCCAGGAAAGAACCAATGTGGGCTGAC

CTGCTGGCTCTGGCTGCTGCCAGAGGGGGACGGGTGCACCGCGCCCCT

GAGCCATACAAGGCTCTGCGCGACCTGAAAGAAGCCAGGGGGCTGCTG

GCTAAGGATCTGTCAGTGCTGGCTCTGAGGGAGGGACTGGGACTGCCC

CCTGGCGACGATCCAATGCTGCTGGCCTACCTGCTGGATCCAAGCAAC

ACTACCCCAGAGGGAGTGGCTAGGAGATATGGAGGGGAATGGACCGAG

GAAGCTGGGGAGAGAGCTGCCCTGTCCGAACGGCTGTTCGCTAATCTG

TGGGGAAGGCTGGAGGGAGAGGAAAGGCTGCTGTGGCTGTACCGGGAG

GTGGAACGCCCTCTGTCCGCTGTGCTGGCTCACATGGAGGCTACAGGC

GTGCGCCTGGACGTGGCTTATCTGAGGGCCCTGTCTCTGGAGGTGGCT

GAGGAAATCGCCAGACTGGAGGCTGAAGTGTTCCGGCTGGCCGGACAT

CCCTTTAACCTGAATAGCAGGGACCAGCTGGAGAGAGTGCTGTTCGAT

GAACTGGGGCTGCCTGCCATTGGCAAGACCGAGAAAACAGGGAAGCGC

TCAACAAGCGCTGCTGTGCTGGAGGCTCTGAGGGAAGCTCACCCCATC

GTGGAGAAGATTCTGCAGTACAGAGAACTGACTAAGCTGAAATCCACC

TATATCGACCCCCTGCCTGATCTGATTCACCCTAGGACAGGCAGACTG

CATACTCGCTTCAACCAGACAGCTACTGCCACCGGAAGGCTGAGCTCC

TCTGACCCAAACCTGCAGAATATCCCTGTGAGAACCCCACTGGGACAG

CGGATCAGGAGAGCTTTTATTGCTGAGGAAGGATGGCTGCTGGTGGCT

CTGGATTACTCCCAGATTGAGCTGAGGGTGCTGGCTCACCTGTCTGGG

GACGAAAACCTGATCCGCGTGTTCCAGGAGGGCAGGGATATTCATACA

GAAACTGCCAGCTGGATGTTTGGAGTGCCTCGCGAGGCTGTGGACCCA

CTGATGAGGAGGGCTGCCAAGACAATCAATTTCGGAGTGCTGTATGGG

ATGTCCGCCCACAGGCTGTCTCAGGAGCTGGCTATCCCCTACGAGGAA

GCTCAGGCCTTCATCGAAAGATACTTCCAGTCTTTCCCTAAGGTGCGG

GCCTGGATTGAGAAAACCCTGGAGGAAGGCAGGAGACGGGGATACGTG

GAAACACTGTTCGGCCGCAGGAGATATGTGCCTGACCTGGAGGCCAGG

GTGAAGTCAGTGCGCGAGGCTGCCGAAAGGATGGCTTTCAATATGCCT

GTGCAGGGAACCGCTGCCGACCTGATGAAACTGGCCATGGTGAAGCTG

TTTCCACGCCTGGAGGAAATGGGGGCTAGGATGCTGCTGCAGGTGCAT

GATGAGCTGGTGCTGGAAGCCCCAAAGGAGAGAGCTGAAGCCGTGGCT

CGGCTGGCCAAAGAAGTGATGGAAGGCGTGTACCCCCTGGCTGTGCCT

-continued
CTGGAGGTGGAAGTGGGAATCGGGGAGGACTGGCTGTCCGCCAAGGAA

TGA (21-2) Construction of *T. aquatics*-derived Thermostable DNA Polymerase Expression Vector A TEF promoter (SEQ ID NO: 66) and a SD terminator (SEQ ID NO: 67) were inserted into the HindIII and KpnI restriction enzyme sites of an autonomous replicating shuttle vector (pPTRII: TaKaRa Bio) to obtain the vector pPTR-TEF-SDt.

SEQ ID NO: 66
GCGGCCGCGGGTGCAAACGGTGGTCAAAGGATGGTTCAGATACAAATT

AGCAACAGGCCAGGCTAGACGCGCGACTATCCACTGCGGCAAATGGTG

AGCTGCAAGCAACGGTAAGATGTGACAGGACGAGCGGTGTGCCGGGAA

AAAAATTGGAGGAGCGCAAAGCGGCGGCTGTCCCTCAGTGGTGCCCAA

ACGTTATCGATAGTACACCAAGCATGGGCAGTGAGCGGCTATACAGAG

GGAATAATAGGCATATCGGCACGACTAGATTCGGTAGAAAGCATCGAA

GAGCAATTCATTGAGCATATTATCACGTGGAATGCGATAGCTGTGGCC

AGGTTGAGACACCGCAAGTGAAAGATACACACATAGATTCTCGATTCG

AGCGGTTTGCCTCCGCCACCGCAGTGCATAGCAAGCAAAGAAACGACA

GTTGGCTCATCATCCGTTACATCATTTTTTCTACTGGCTCCGCTCGGT

GGGCTCCCAACGAAGCAGCAAAAAAGTGAGAGAAAAAAACTAGCTTGG

CGGGGCAACAGAAGCTAGACCCTTTGGCTCGCTTAGTCAGTGCGCCCA

CTCACTCACACTCAAAAAGGCCACCCCTCCCGCACCCTCTTCTCATCA

CCGTCTTCATACCACGGTTCGTCAAGCAATCGTATCTGGTAAGCTTTG

ACCTCCTCGAGCGGGCTCCACTTTGCTATTTCTTGGATCTGCTCTTTC

TTTTCTCTCTACCTCTTTTTCTAACCTCTCTTCAGAAAGTTCAACCGT

ACTTCACTCCATCTTCCTACGTCACTCTAGA

SEQ ID NO: 67
TAAAGCGGCGTGCTCTGCACATAACACGTGTCGTGTTTGGGTTCGGTA

TGGGTAATGGCGAATGGGGACATGCATTTATGGGATAGGGGCTGGGT

TGGTGTAATCAAATGTGCATACAGACCAGCTGATACGAATACTACAAC

TTACCCCGACACACGCATTCATGTGACGCCCAACACCTCGTCTAACTC

ATCGGGCAACTCACCTCAATCCGATTCAGCCTCCCGG

The TEF promoter was derived from *Aureobasidium pulluans*, and the SD terminator was derived from *Colletotrichum orbiculare*, and both of them were amplified by PCR using the extracted genome DNA as a template (SEQ ID NOs: 68, 69, 70, and 71). They were designed such that PmeI and XmaI restriction enzyme sites were introduced between the TEF promoter and the SD terminator.

SEQ ID NO: 68
GCGGCCGCGGGTGCAAACGGTGGTCAAA

SEQ ID NO: 69
ATATCTAGAGTGACGTAGGAAGATGGAG

SEQ ID NO: 70
GTTTAAACAGATCTCCCGGGTAAAGCGGCGTGCTCTGCAC

SEQ ID NO: 71
TATGGTACCGGGAGGCTGAATCGGAT

Next, a gene encoding *T. aquatics*-derived thermostable DNA polymerase was inserted into the PmeI and XmaI restriction enzyme sites of pPTR-TEF-SDt to obtain a vector pPTR-TEF-Taq. Furthermore, in order to add a FLAG tag, amplification was carried out by using the vector pPTR-TEF-Taq as a template and by using the primers designed such that a PmeI restriction enzyme site was introduced into the 5' terminal sequence and an XmaI restriction enzyme site was introduced into the into the 3' terminal sequence (SEQ ID NOs: 72 and 73), followed by being inserted into the PmeI and XmaI restriction enzyme sites of the pPTR-TEF-SDt so as to obtain the vector pPTR-TEF-FLTaq.

SEQ ID NO: 72
ATAGTTTAAACATGGATTATAAGGATGACGATGACAAGATGAGAGGCAT

GCTGCCAC

SEQ ID NO: 73
ATGGTACCGGGAGGCTGAATCGGAT (21-3) Transformation of *A. oryzae*

The vector pPTR-TEF-FLTaq was introduced into filamentous fungi (*Aspergillus oryzae*). Transformation was carried out by a protoplast PEG method. *A. oryzae* was cultured on a CD solid medium (containing 6.0 g of $NaNO_3$, 0.52 g of KCl, 1.52 g of $KH_2PO_4$, 2 ml of 1M $MgSO_4$-$7H_2O$, 10.0 g of Glucose, 1.0 mg of $FeSO_4$-$7H_2O$, 8.8 mg of $ZnSO_4$-$7H_2O$, 0.4 mg of $CuSO_4$-$5H_2O$, 0.1 mg of $Na_2B_4O_7$-$10H_2O$, 0.05 mg of $(NH_4)_6Mo_7O_{24}$-$4H_2O$, and 20.0 g of Agar per 1 L; and adjusted to pH6.5 with 1N KOH) at 30° C., and this culture was suspended in 10 ml of 0.1% Tween 80 and 0.8% NaCl, the suspension was filtered through a glass filter (3G2), and the filtrate was collected. The filtrate was centrifuged at 3,000 rpm for 5 min to deposit conidia, and the supernatant was removed. The conidia was washed with 10 ml of 0.1% Tween80 twice, and then suspended in an appropriate amount of sterile water to obtain a spore suspension.

The spore suspension of *A. oryzae* was inoculated into 100 ml of CD liquid medium, and cultured with shaking at 30° C. for 20 hours.

The culture was filtered through a glass filter (3G1) to collect hyphae and washed with sterile water, the hyphae were held by a spatula, and then water was sufficiently removed from the hyphae. An appropriate amount of hyphae was added and suspended in a solution for making protoplasts in a 50 ml-centrifuge tube made of polypropylene, and gently shaken at 30° C. for two hours to make the solution into protoplasts. They were filtered through the glass filter (3G2), and the filtrate was centrifuged at 2000 rpm for 5 min to collect protoplasts which were washed with 0.8M NaCl twice. The protoplasts were suspended in a Solution 1 (0.8 M NaCl, 10 mM $CaCl_2$, and 10 mM Tris-HCl (pH8.0)) at $2 \times 10^8$/ ml, and 0.2 volume of a Solution 2 (40% (w/v) PEG4000, 50 mM $CaCl_2$, and 50 mM Tris-HCl (pH8.0)) was added and gently suspended. To 0.2 ml of the protoplast suspension, 20 µg of pPTR-TEF-FLTaq was added, and the mixture was put on ice for 30 min. To this, 1 ml of the Solution 2 was added and gently suspended, and was left at room temperature for 15 min. Then, 8.5 ml of the Solution 1 was added and gently suspended. Next, the suspension was centrifuged so as to collect protoplasts and to remove the supernatant, and the protoplasts were suspended in 0.2 ml of the Solution 1. The protoplast suspension was added and suspended in 5 ml of CD soft agar selection medium (a medium in which agar in the CD medium was made to be 0.5%, 0.8M NaCl and 0.1 µg/ml Pyrithiamine (TaKaRa Bio) were added thereto and the temperature was kept at 50° C.). The suspension was seeded on CD selection medium so that the protoplasts were dispersed uniformly and cultured at 30° C. for seven days.

(21-4) Culture of *A. oryzae* and Production of *T. aquatics*-derived Thermostable DNA Polymerase The transformant was inoculated in 600 ml of CD medium and cultured at 30° C. for four days. They were centrifuged at 5000 rpm for 10 min to collect cells, the collected cells were suspended in a disruption buffer solution (50 mM Tris-HCl, pH7.5, 50 mM KCl), and cells were disrupted by using 0.5 mm of glass beads, and then subjected to heat-treatment at 70° C. for 60 min and centrifugation at 12000 rpm for 30 min to obtain a supernatant containing thermostable DNA polymerase. This was purified by using FLAG Tagged protein Immunoprecipitation Kit (Sigma), and *T. aquatics*-derived thermostable DNA polymerase preparation was obtained.

(21-5) Examination of Contamination of Non-specific Nucleic Acid by PCR

Figure 7:
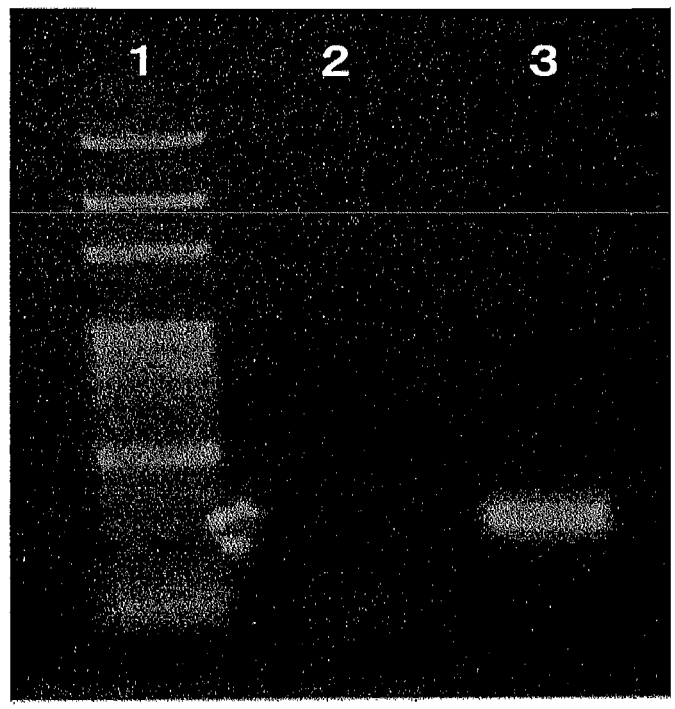
[FIG. 7]

FIG. 7 is a photograph of agarose electrophoresis showing whether or not non-specific nucleic acid is contaminated by using the above-mentioned thermostable DNA polymerases. The lane 1 shows a marker, the lane 2 shows PCR without adding a template, and the lane 3 shows PCR using *Escherichia coli* DNA as a template. The PCR was carried out by using SEQ ID NOs: 85 and 86 as a primer, and the PCR temperature conditions and the PCR solution composition were made to be the same as in (6-3), and 45 cycles were carried out. This shows that an amplification product of bacterial 16S rRNA-derived gene was detected when *Escherichia coli* was used as a template, and the amplification product of bacterial 16S rRNA-derived gene was not detected when a template was not added.

(22) Real-time PCR of Various Thermostable DNA Polymerases Using Non-display Method (Masked Primer Dimer Method)

Figure 8:
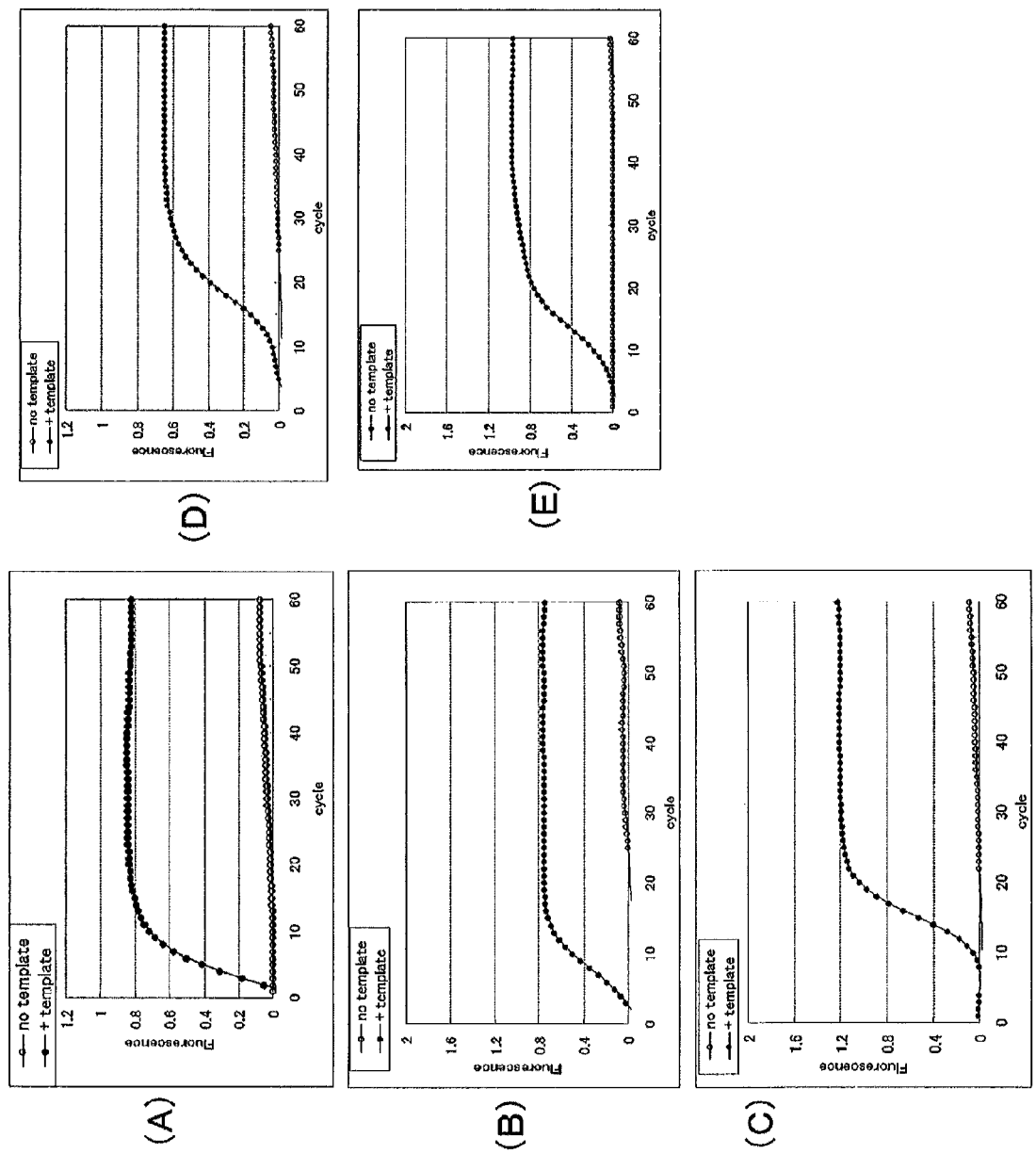
[FIG. 8]
Figure 9:
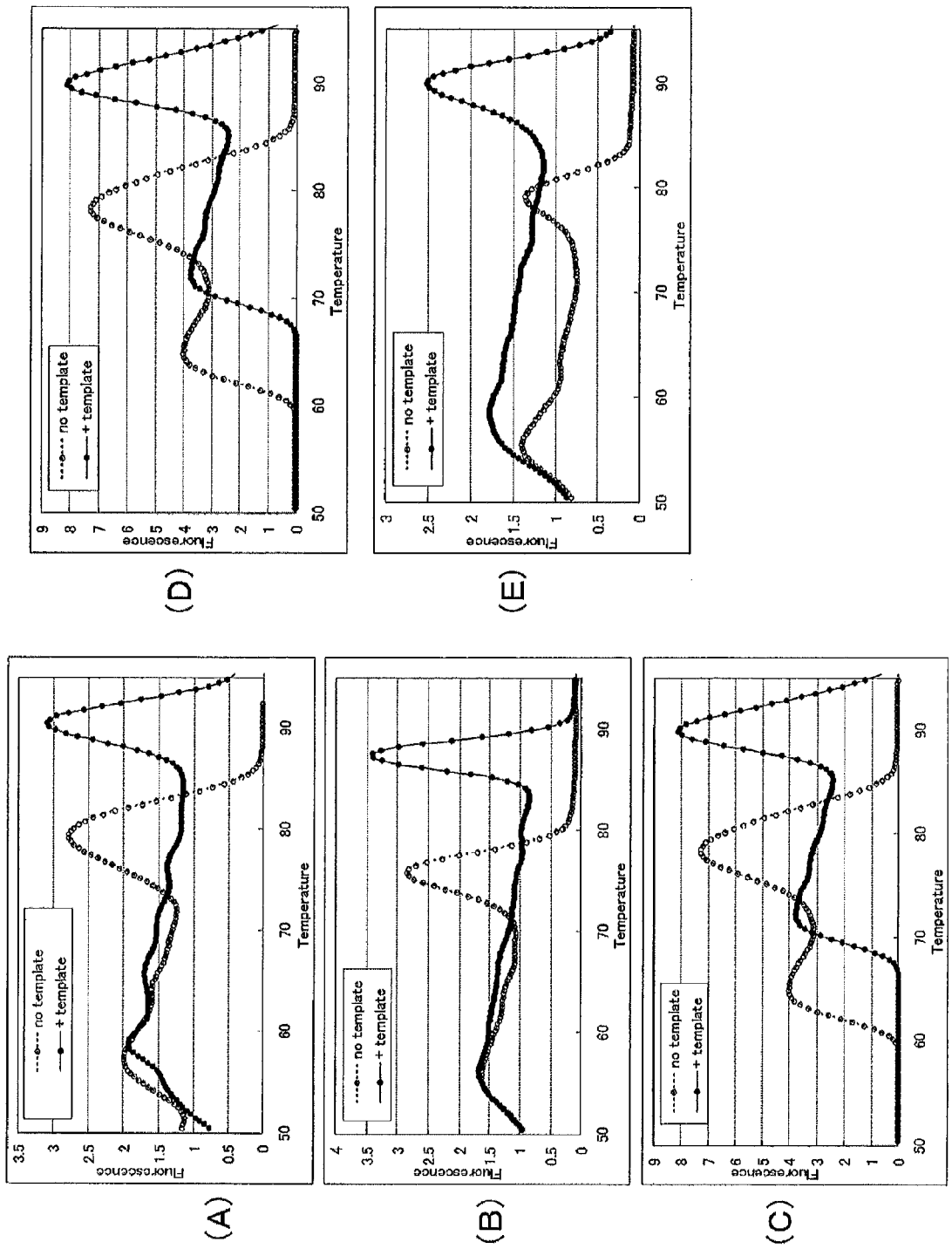
[FIG. 9]

Real-time PCR was carried out by the non-display method by using the above-obtained thermostable DNA polymerase preparation. The real-time PCR was carried out by using *T. aquaticus*-derived thermostable DNA polymerase preparation (FIG. 8A and FIG. 9A), mutated *P. furiosus*-derived thermostable DNA polymerase preparation (FIG. 8B and FIG. 9 B), and mutated *T. gorgonarius*-derived thermostable DNA polymerase preparation (FIG. 8 C and FIG. 9 C), which were produced by using *S. cerevisiae* as a host, *T. aquaticus*-derived thermostable DNA polymerase preparation (FIG. 8D, FIG. 9D) produced by using *P. pastoris* as a host, and *T. aquaticus*-derived thermostable DNA polymerase preparation (FIG. 8E, FIG. 9E) produced by using Tobacco BY-2 as a host. Furthermore, FIGS. 8A, B, C, D and E show an amplification curve, and FIGS. 9 A, B, C, D and E show a melting curve, respectively. The solid lines show a case in which a template was added, and the broken lines show a case in which a template was not added. The real-time PCR reagent was the same as that in (17). The real-time PCR program was carried out at 94° C. for 1 min, 50° C. for 30 sec, 72° C. for 1 min, and 84° C. for 2 sec as one cycle, followed by detecting a fluorescence value, which was repeated 60 times. The results of the real-time PCR show that the use of the non-display method enabled an analysis without detecting a non-specific amplification product or a signal of the amplification curve of bacterial DNA which damages the quantification in the real-time PCR.

Example 2

Quantification Identification A by Non-display Method

Hereinafter, *T. aquaticus*-derived thermostable DNA polymerase produced by using host *S. cerevisiae* is referred to as "e-DNAP".

By using the above-obtained e-DNAP, quantification identification of a sample by the non-display method was tried. The real-time PCR was carried out in a system whose total amount was 20 µL by using real-time PCR machines Light-Cycler 1.5 (Roche Diagnostics K.K.) and RotorGene 6000 (QIAGEN) and a reagent for real-time PCR by the following constitution by using the below-mentioned universal primers for detecting bacteria.

```
Forward Primer:
CTCCTACGGGAGGCAG          (SEQ ID NO: 43)

Reverse Primer:
ACTACCAGGGTATCTAATCCTG    (SEQ ID NO: 44)
``` e-DNAP (5 units/µL): 1 µL,
*E. coli* genomic DNA template or Water PCR grade: 2 µL,
SYBR Green I (TAKARA) 300-folded diluent: 2 µL,
PCR primers (10 µM): 0.8 µL each,
10× Buffer (500 mM KCl, 100 mM Tris-HCl): 2 µL,
25 mM MgCl$_2$: 1 µL,
2 mM dNTP mix: 2 µL,
Water PCR grade: 8.4 µL Furthermore, the program of the real-time PCR was carried out according to the conditions described in Table 1.

TABLE 1

| Program | Analysis Mode | Cycles | Segment | Target Temperature | Time | Fluorescence Acquisition Mode |
|---|---|---|---|---|---|---|
| Pre-incubation | None | 1 | 1 | 95° C. | 2 min | None |
| Amplification | Quantification | 50 | Denaturation | 95° C. | 15 sec | — |
|  |  |  | Annealing | 55° C. | 15 sec | — |
|  |  |  | Extension | 72° C. | 15 sec | — |
| Melting Curve Analysis | Melting Curves | 1 | Denaturation | 95° C. | 0 sec | — |
|  |  |  | Annealing | 70° C. | 15 sec | — |
|  |  |  | Melting | 95° C. 0.1° C./sec. | 0 sec | Continue |
| Cooling | None | 1 | 1 | 40° C. | 30 sec | — |

FIG. 13 and FIG. 14 are an amplification curve and a melting curve showing analysis according to the program conditions described in Table 1.

FIG. 13 shows that an amplification curve appears even if a template is not included; and FIG. 14 shows that a melting curve of the primer dimer was observed around about 76° C.

TABLE 2

| Program | Analysis Mode | Cycles | Segment | Target Temperature | Time | Fluorescence Acquisition Mode |
|---|---|---|---|---|---|---|
| Pre-incubation | None | 1 | 1 | 95° C. | 2 min | None |
| Amplification | Quantification | 50 | Denaturation | 95° C. | 15 sec | — |
| | | | Annealing | 55° C. | 15 sec | — |
| | | | Extension | 72° C. | 15 sec | — |
| | | | 1 | 84° C.* | 2 sec | single |
| Melting Curve Analysis | Melting Curves | 1 | Denaturation | 95° C. | 0 sec | — |
| | | | Annealing | 70° C. | 15 sec | — |
| | | | Melting | 95° C. 0.1° C./sec. | 0 sec | Continue |
| Cooling | None | 1 | 1 | 40° C. | 30 sec | — |

With reference to the results of the melting curve shown in FIG. 14, the temperature at the time when fluorescence was detected was set to 84° C., the middle temperature between that of the primer dimer and that of *E. coli*. The real-time PCR was carried out according to the conditions described in Table 2.

FIG. 15(A) is a graph showing an amplification curve of the results of real-time PCR according to the program conditions described in Table 2. According to this method, when water was used as a template, a primer dimer was not displayed; and when *E. coli* was added as a template, a normal amplification curve of a target amplification product was observed.

Example 3

Quantification Identification B by Non-display Method

By using the e-DNAP and the non-display method in accordance with the present invention, infectious bacteria and fungi which were present in various samples were tried to be quantified and identified. A real-time PCR reagent for detecting bacteria and the primer constitution were the same as in Example 2. This Example was carried out in the same manner as in Example 2 except that a real-time PCR reagent for detecting fungus and the primer constitution were as follows: an rTaq DNA polymerase (ToYoBo) was used as a thermostable DNA polymerase produced by using bacteria as a host, and the below-mentioned universal primer for detecting fungi was used.

```
Forward Primer:
GAATGAGTACAATGTAAATACCTTAACG      (SEQ ID NO: 9)

Reverse Primer:
GCTTTCGCAGTAGTTAGTCTTCA           (SEQ ID NO: 45)
```

Since CFU/ml is usually used as the unit of the concentration of the infectious bacteria/fungi, in order to allow the unit to match to that for the PCR quantification assay calculated in DNA concentration, calculation was tried via McFarland turbidimetric method. Specifically, after *E. coli* and *C. albicans* were suspended in physiological saline, respectively, a bacterial suspension that was allowed to match to a median value of 0.5 McFarland was formed and each suspension was developed onto a medium, and the CFU/ml was calculated. At the same time, DNA was extracted and DNA/ml was calculated, and a calibration curve of the real-time PCR of the DNA solution was drawn.

Converted values of the CFU/ml and the DNA/ml are shown below.

*E. coli:* 0.5 McFarland=$1.3 \times 10^8$ CFU/ml=8.6 µg/ml (8.6 ng/µl)

*C. albicans:* 0.5 McFarland=$2.5 \times 10^6$ CFU/ml=18.0 µg/ml (18.0 ng/µl)

Furthermore, as a result of the calibration curve, the following results are obtained.

*E. coli*: correlation coefficient is −1.00, and calculation formula: number of cycles=−4.1×concentration+14.6

*C. albicans*: correlation coefficient is −1.00, and calculation formula: number of cycles=−4.4×concentration+14.5

As the positive and quantitative controls, the following two bacteria were quantified for every measurement.

*E. coli:* $1.3 \times 10^5$ CFU/µl=8.6 ng/µl, 2 µl (20 µl of measurement system)

*C. albicans:* $2.5 \times 10^3$ CFU/µl=18.0 ng/µl, 2 µl (20 µl of measurement system)

As mentioned above, in this system, when bacteria and fungi are positive, the quantification was carried out by using the following estimation formula.

Bacteria (converted value of *E. coli*), effective number: 2 digits $1.3 \times 10^8 \times [10^{\{1-(number\ of\ cycles-number\ of\ control\ cycles+4.1)/4.1\}}]$ CFU/ml Fungus (converted value of *Candida Albicans*), effective number: 2 digits $2.5 \times 10^6 / 18 \times [10^{\{3-(number\ of\ cycles-number\ of\ control\ cycles+7.7)/4.4\}}]$ CFU/ml (1) Examination of Daily Life Water by Using Highly Sensitive Quantification Method of Subject to be Detected Next, for the purpose of evaluating the practicality of the constructed "highly sensitive quantification method of a subject to be detected," the following four types of daily life water were examined.

(A) Tap water: water from water supply in Toyama University Hospital.

(B) Spring water: famous water of Toyama Prefecture selected for one of "the 100 best waters in Japan" in 1985 by Environment Agency.

(C) Hot spring water: heated and circulated hot spring water. No additives are contained.

(D) Air-conditioning water: air-conditioning water in Toyama University Hospital.

Twenty-five-ml each of tap water, spring water and hot spring water and 1 ml of air-conditioning water were centrifuged at 8000 rpm for 20 min, and DNAs were extracted from pellets by using InstaGene Matrix (Bio-Rad).

Examination of infectious bacteria/fungi was carried out by using the DNA extraction solution as a template. As a result of the examination, no fungi were detected from any of the four types of daily life waters (B in FIG. 15(B)). As to bacteria, however, no bacteria were present in the tap water and the spring water (famous), but the hot spring water and the air-conditioning water proved positive (B and C in FIG. 15(C)). As a result of quantification thereof, the following measurement values were obtained.

Hot spring water: 1.2 CFU/ml (converted value of *E. coli*)
Air-conditioning water: 78 CFU/ml (converted value of *E. coli*)

As a result, it was revealed that the hot spring water included bacteria although the amount was small and the air-conditioning water included bacteria at a high concentration.

(2) Examination of Foods Using Highly Sensitive Quantification Method of Subject to be Detected Since bacterial contamination or fungal contamination in foods may directly cause symptoms of food poisoning, examination thereof is socially important. At this time, cream puffs having high risk of food poisoning by *Staphylococcus aureus* were used as a sample. Note here that as an "old cream puff," a cream puff that had been left at room temperature for several days was used, and as a control (a new cream puff), a cream puff in best-before date, which had been preserved in a refrigerator (not higher than 5° C.), was used. For extraction of DNA, firstly, 27.4 g of only cream part of each cream puff was collected and added to 20 ml of sterilized physiological saline, which was then centrifuged to remove supernatant. This operation was repeated three times so as to remove the oil component. Thereafter, DNA was extracted from the centrifuged pellet by using InstaGene Matrix, the examination of infectious bacteria/fungi was carried out by using the extracted DNAs as a template.

Figure 16:
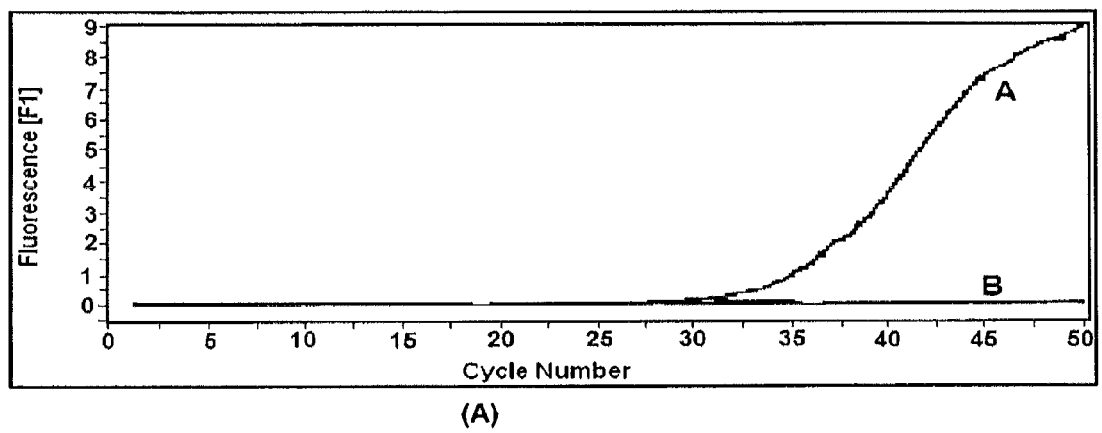
[FIG. 16]
Figure 16:
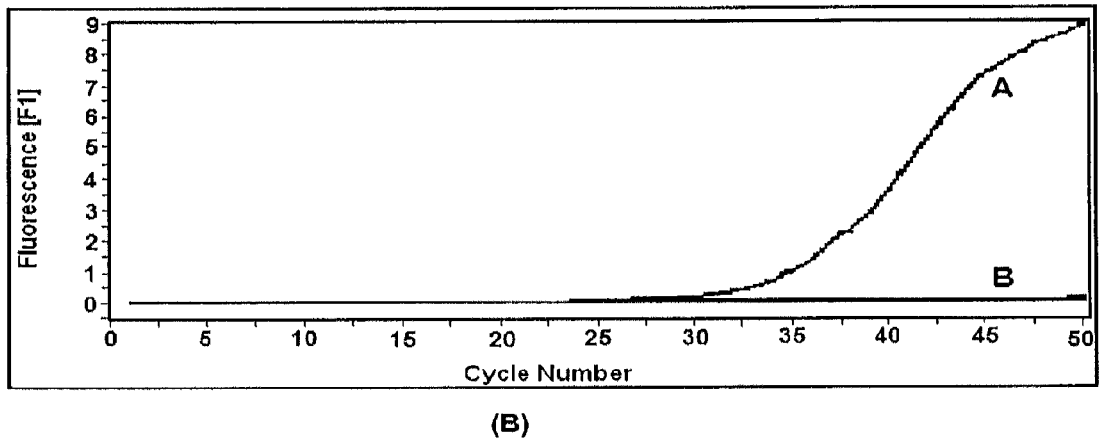

As a result, extremely small amount of fungi was detected from both the old cream puff and the control at substantially the same level (FIG. 16). In view of the fact that cream puff shell is leavened with yeast, it is not thought that new fungal contamination occurs.

Figure 17:
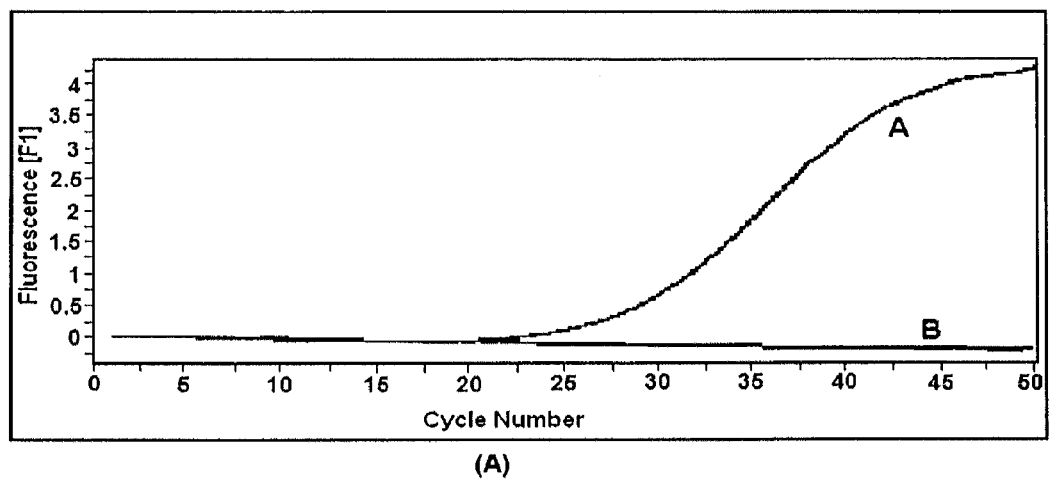
[FIG. 17]
Figure 17:
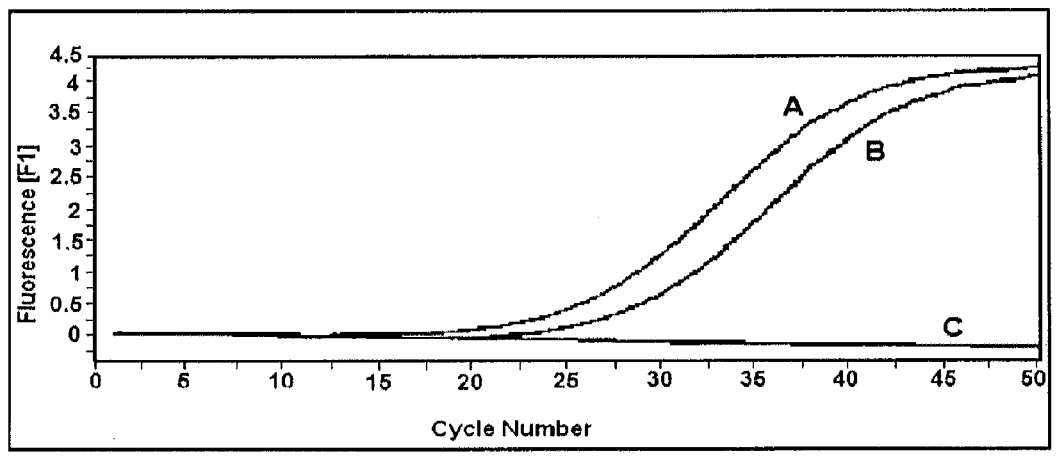

As to the infectious bacteria, no bacteria were detected in the fresh cream puff, while proliferation of considerable number of bacteria was observed in the old cream puff (FIG. 17). The amount of proliferation was quantified, and as a result, the following measurement value was obtained.

Old cream puff: $1.5 \times 10^7$ CFU/(cream)g (converted value of *E. coli*)

(3) Examination of Septicemia Using Highly Sensitive Quantification Method of Subject to be Detected Next, an examination of septicemia using highly sensitive quantification method of a subject to be detected was tried. At this time, as septicemia patient samples, blood samples from each of the patient A with fungemia (septicemia caused by *Candida Albicans*) and the patient B with bacteriemia (septicemia caused by *Bacillus* species) were used. For extraction of DNA, 2 µl each of the blood samples from the patients A and B was collected, and 2 µl from a blood culture bottle of the patient B was further collected, DNAs were extracted by using InstaGene Matrix, respectively, and they were used as a template to carry out the examination of infectious bacterium/fungus.

Figure 18:
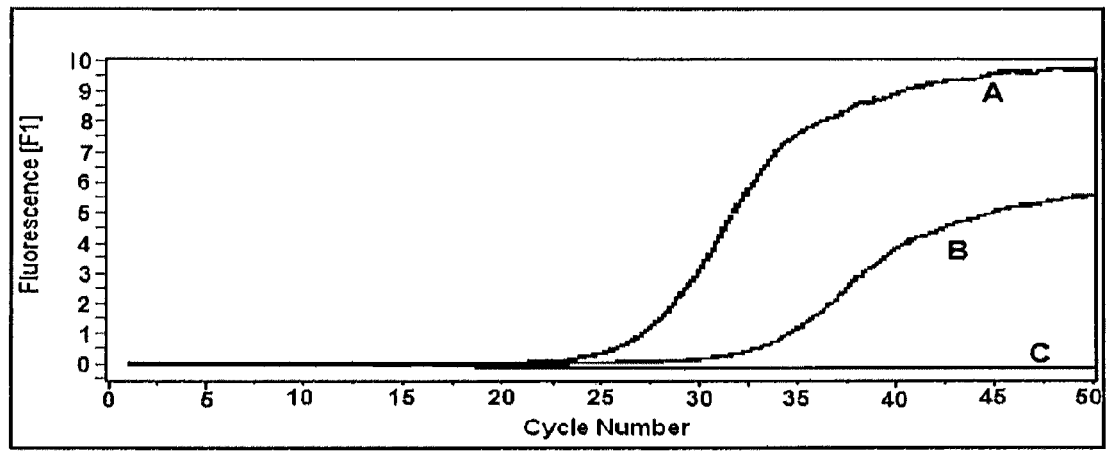
[FIG. 18]
Figure 18:
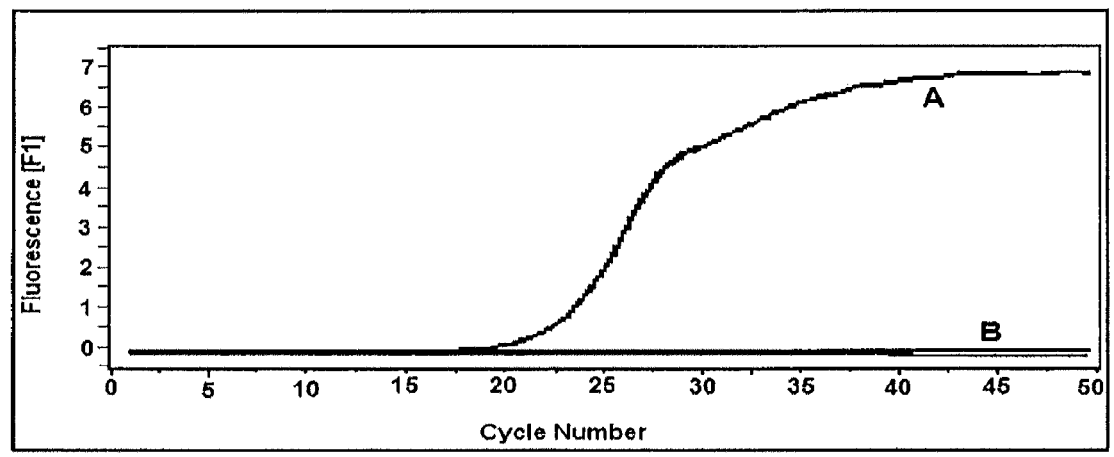

As a result, in the patient A, bacterial infection was not observed, only fungal infection was observed (FIG. 18). As a result of the quantification of the fungal infection, the following measurement values were obtained.

Patient A: $9.7 \times 10^4$ CFU/(blood)ml (converted value of *Candida Albicans*)

Figure 19:
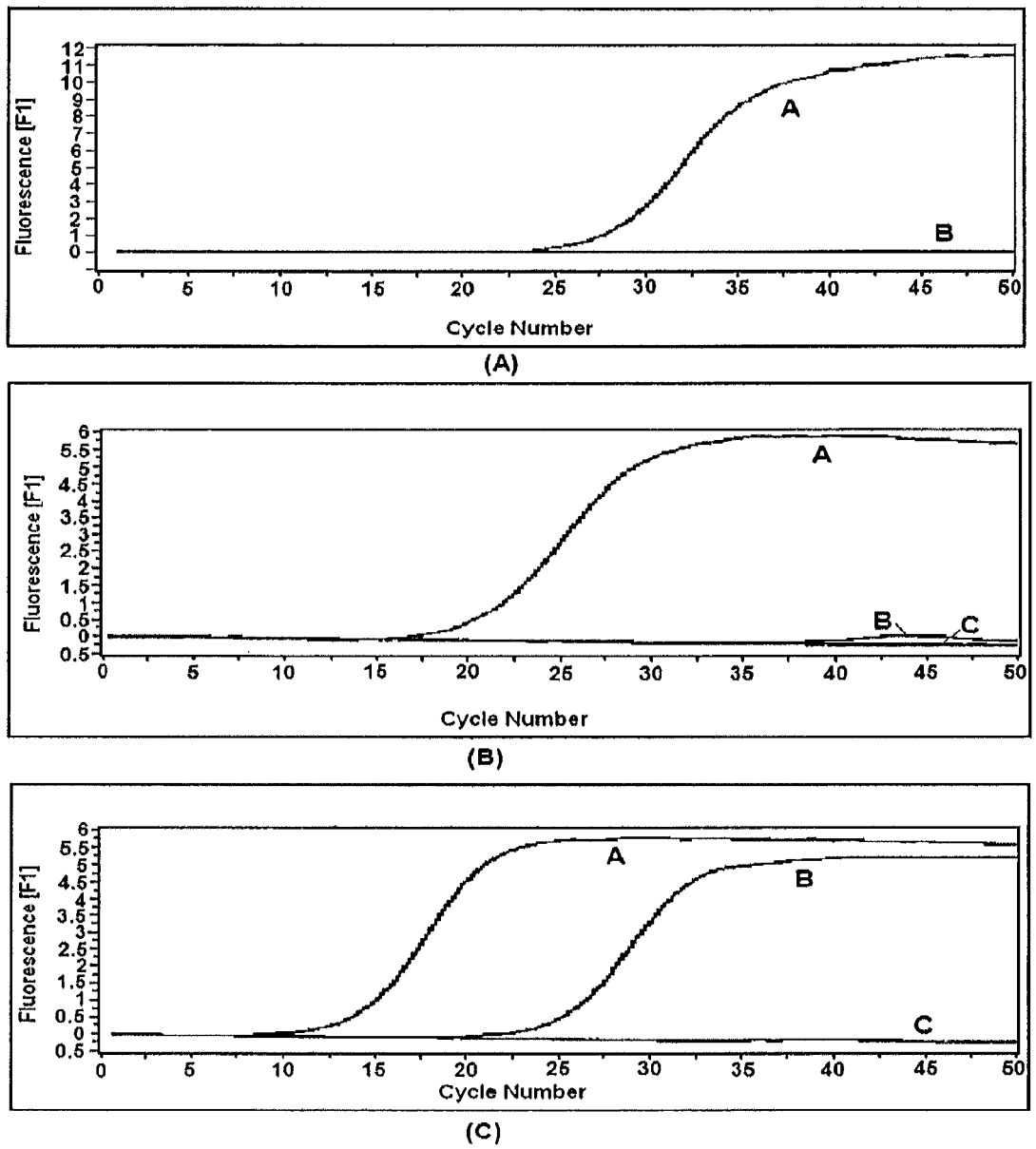
[FIG. 19]

Furthermore, in the patient B, no fungal infection was observed, and only an extremely small amount of bacterial infection was observed (FIG. 19). Also, when a blood culture bottle was confirmed, a large amount of bacteria proliferation was observed. As a result of quantification calculation of this bacterial infection, the following measurement values were obtained.

Patient B: $2.0 \times 10^5$ CFU/(blood)ml (converted value of *E. coli*)

Figure 20:
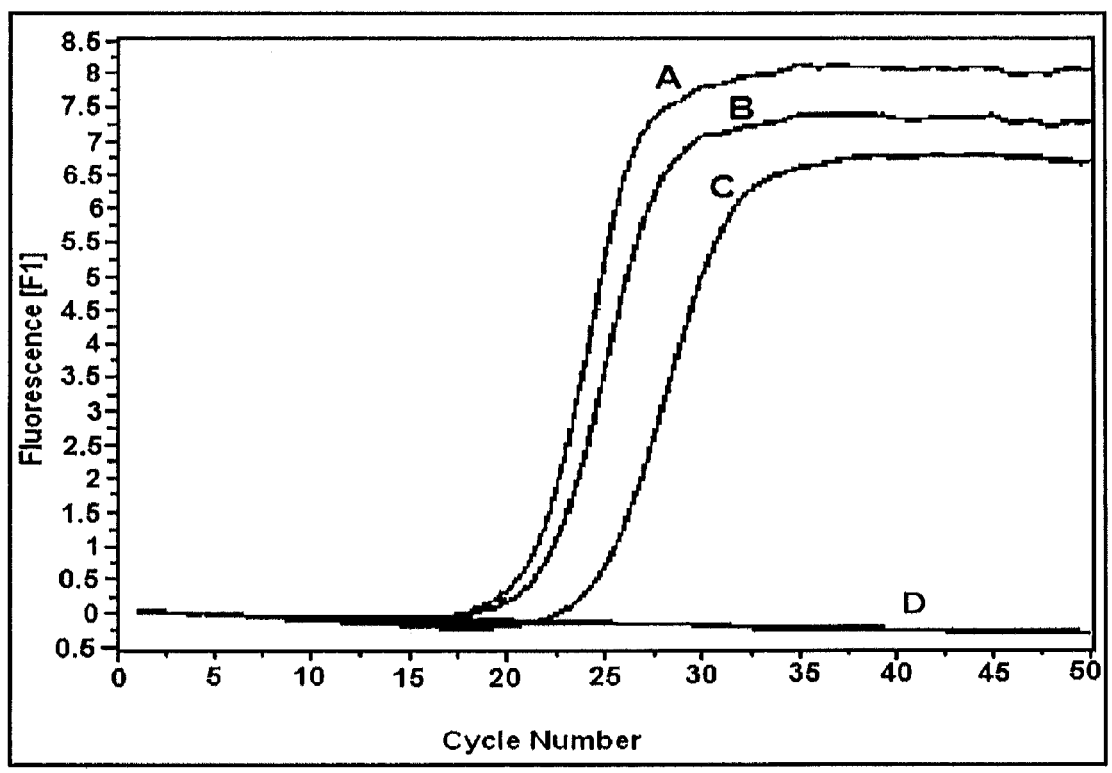
[FIG. 20]

Furthermore, FIG. 20 shows the results of real-time PCR carried out by using MRSA DNA as a template and the following Spa and mecA primers specific to MRSA.

```
Spa Forward Primer:
GCGATTGATGGTGATACGGTT      (SEQ ID NO: 46)

Spa Reverse Primer:
AGCCAAGCCTTGACGAACTAAAGC   (SEQ ID NO: 47)

mecA Forward Primer:
AAAATCGATGGTAAAGGTTGGC     (SEQ ID NO: 48)

mecA Reverse Primer:
AGTTCTGCACTACCGGATTTGC     (SEQ ID NO: 49)
```

Use of MRSA-specific primers in addition to the universal primers used in the above-mentioned Example made it possible to design an analysis targeting specific infectious bacteria/fungi.

Example 4

Drug Sensitivity Test Applying Highly Sensitive Quantification Method of Subject to be Detected A rapid liquid phase drug sensitivity test was tried by applying a highly sensitive quantification method using the e-DNAP and the non-display method in accordance with the present invention. In current drug sensitivity tests, it generally takes several days to obtain results. However, when the highly sensitive quantification method in accordance with the present invention is applied, results can be obtained in only four to six hours. Note here that the liquid phase drug sensitivity test is already described in a preceding patent (WO2002/052034), but it does not use a highly sensitive method. Accordingly, a sensitive test must be started once culture was carried out, so that it takes at least one day to obtain a result.

(1) Culture

An equal amount of each sample (for example, blood of septicemia) was infused into a liquid medium (BHI: Brain Heart Infusion), each sample medium was collected before culture, two hours after the culture, and four hours after the culture under the condition in which an antibiotic agent was added or not added, cells were subjected to centrifugation and pelletizing so as to obtain DNA, respectively. Furthermore, it is desirable that extraction of DNA is carried out by using an automatic nucleic acid extraction device.

(2) Quantification of Bacteria by Real-time PCR

A real-time PCR reagent for detecting bacteria, conditions and the primer constitution were the same as in Example 2.

(3) Determination Method

When calculation is carried out when the quantification result before culture is defined as 0 and the quantification result two hours after and four hours after culture in which an antibiotic agent was not added is respectively defined as 100

(an enrichment rate when an antibiotic agent was not added is defined as 100%), the enrichment rate was calculated two hours after and four hours after the culture in which an antibiotic agent was added.

For example, the amount of bacteria/fungi before culture is N0h, the amount of bacteria two hours after culture in which an antibiotic agent is not added is N2h, and the amount two hours after culture in which an antibiotic agent is added is K2h, the enrichment rate two hours after an antibiotic agent is added can be calculated by the following formula:

Enrichment rate two hours after an antibiotic agent is added=(K2h−N0h)/(N2h−N0h)×100 (%)

Alternatively, instead of comparing the enrichment rates, the amounts thereselves may be compared directly.

(4) Result 1: Comparison of Amount of Bacteria Itself

Figure 21:
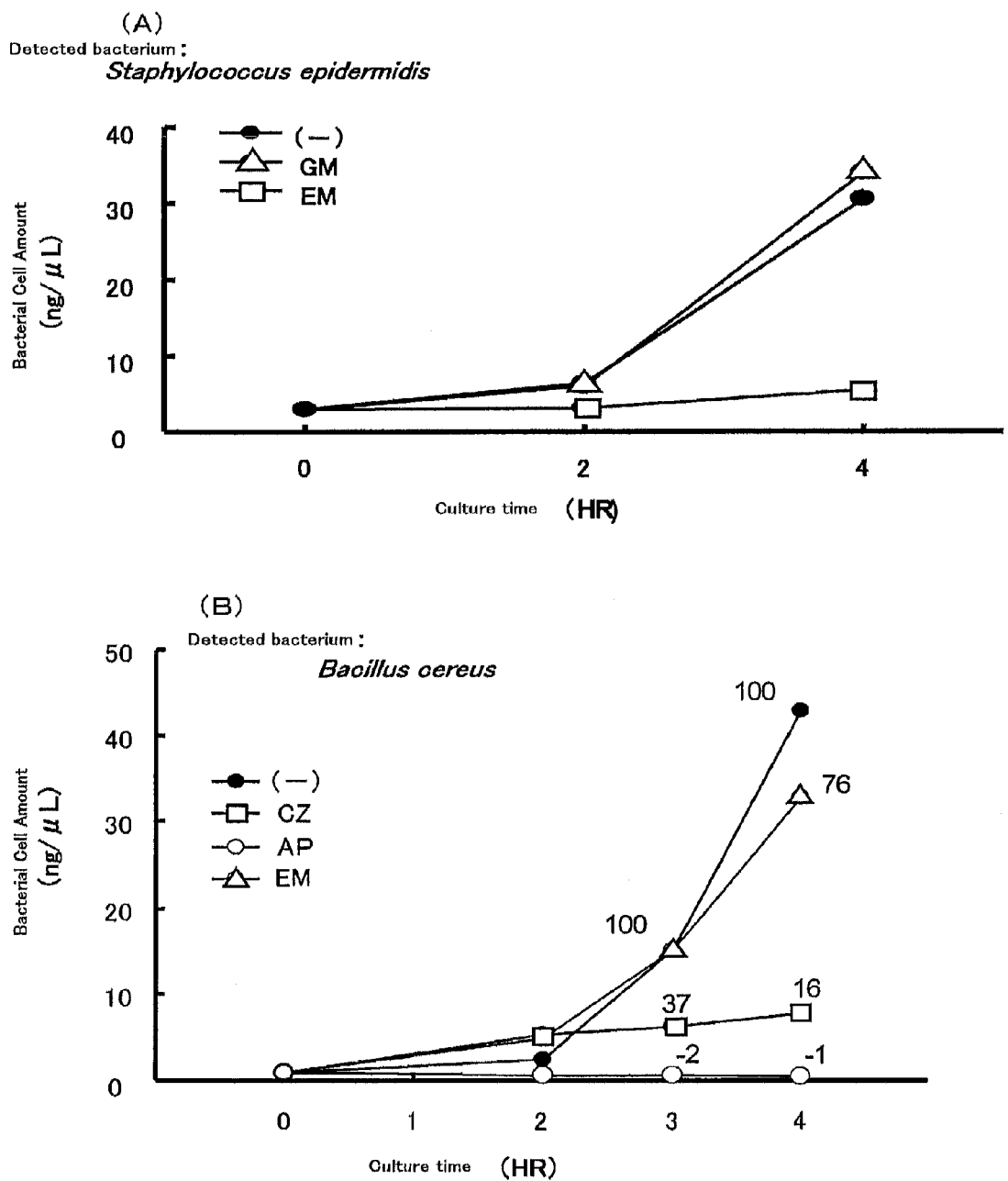
[FIG. 21]

With respect to the detected *Staphylococcus epidermidis*, the drug sensitivity with respect to each of 10 μg/mL of gentamicin (GM) and 10 μg/mL of erythromycin (EM) was evaluated two hours and four hours after culture, respectively. As a result, it was revealed that both two hours after and four hours after culture, the sensitivity to EM was observed, but sensitivity to GM was not observed (FIG. 21(A)). However, since *Staphylococcus epidermidis* was not much proliferated after two hour of culture, in order to evaluate more accurately, evaluation should be carried out after four hours of culture.

(5) Result 2: Calculation when Enrichment Rate without Adding Antibiotic Agent is Defined as 100%

With respect to the detected *Bacillus cereus*, the drug sensitivity with respect to each of 10 μg/mL of cefazolin (CZ), 10 μg/mL of ampicillin (AP) and 10 μg/mL of erythromycin (EM) was evaluated two, three, and four hours after culture, respectively. As a result, when evaluation after four hours when the enrichment is large, it is revealed that the sensitivity to AP was observed (enrichment rate: 0%) and the sensitivity to CZ was observed to some extent (enrichment rate: 16%), but the sensitivity to EM was hardly observed (enrichment rate: 76%) (FIG. 21(B)). Thus, since the "level" of the sensitivity is affected by the speed of proliferation of bacteria, uniform time setting is required. However, evaluation whether strong sensitivity to an antibiotic agent is shown or not shown at all can be determined even in an early stage such as two hours after culture.

Example 5

Amniotic Test of Intrauterine Infection Using Highly Sensitive Detection Method of Subject to be Detected By using a highly sensitive detection method using the e-DNAP and the non-display method in accordance with the present invention, a rapid and simple amniotic test of intrauterine infection was carried out. Since the greatest cause of premature birth is intrauterine infection, which have a risk that a fetus may die, an analysis method for rapidly determining the presence of infection has been demanded. In the intrauterine infection, the infection rate of infectious microorganisms such as of *Mycoplasma* and *Ureaplasma*, in addition to bacteria and fungi, is extremely high. Since the base sequences of the genus *Mycoplasma* and the genus *Ureaplasma* are extremely different from the base sequence of bacteria, they cannot be detected by using universal primers of bacteria. Accordingly, it is necessary to use a primer of each microorganism.

(1) Primer Set and Reagent for PCR

The real-time PCR reagent for detecting bacteria and fungi and the primer combinations are the same as in those in Example 3.

Hereinafter, the primer constitutions for detecting the genus *Mycoplasma* and the genus *Ureaplasma* are shown. For detection of the genus *Mycoplasma* and the genus *Ureaplasma*, a nested PCR method was used.

For detection of the genus *Mycoplasma* and the genus *Ureaplasma*, e-DNAP was used, and the PCR reagent the same as in Example 2 was used. The PCR program was the same as in Example 2.

```
Mycoplasma Forward Primer:
GATGATCATTAGTCGGTGG         (SEQ ID NO: 50)

Mycoplasma Reverse Primer:
CTACCTTAGGCGGTCGTC          (SEQ ID NO: 51)

Mycoplasma Forward nested Primer:
GACATCCTTCGCAAAGCTAT        (SEQ ID NO: 52)

Mycoplasma Reverse nested Primer:
CAGTTACCCAGGCAGTATCTC       (SEQ ID NO: 53)

Ureaplasma Forward Primer:
GAACGAAGCCTTTTAGGC          (SEQ ID NO: 54)

Ureaplasma Reverse Primer:
GATACAGCTAGACGTTAAGCATCTA   (SEQ ID NO: 55)

Ureaplasma Forward nested Primer:
TAACATCAATATCGCATGAGAAG     (SEQ ID NO: 56)

Ureaplasma Reverse nested Primer:
CAGTACAGCTACGCGTCATT        (SEQ ID NO: 57)
```

(2) PCR Detection Method

With the above-mentioned primer set, it is possible to determine whether any one of bacteria, fungi, the genus *Mycoplasma*, and the genus *Ureaplasma* is present in the amniotic fluid rapidly and simply. The detection method may use a real-time PCR method or may use a method of confirming by subjecting a PCR product to electrophoresis on an agarose gel. The method of Example 3 using e-DNAP enables bacteria and fungi to be detected with a high sensitivity, and the nested PCR method enables the genus *Mycoplasma* and the genus *Ureaplasma* to be detected with a high specificity.

(3) Results

From an amniotic fluid sample 1 suspected to have intrauterine infection, infection with a bacterium was confirmed (FIG. 22(A)). Furthermore, from an amniotic fluid sample 2 of threatened premature delivery, infection with the genus *Ureaplasma* was confirmed (FIG. 22(B)). These examinations can be carried out in about two hours rapidly and simply. Furthermore, the primer set of this Example can be used for examinations of contamination in, for example, an organism experiment environment such as a culture solution of the cultured cells (bacteria, fungus, and *Mycoplasma*).

As to the detected genus *Ureaplasma*, the base sequence of the amplification product was further analyzed, and as a result, it was confirmed that the detected genus *Ureaplasma* was the *Ureaplasma parvum*. In this way, the species level of the detected bacteria, fungi, the genus *Mycoplasma*, and the genus *Ureaplasma* can be identified by subjecting the PCR amplification products to sequencing. Alternatively, species can be identified by analyzing the combination of Tm values of a plurality of amplification products (WO2007/097323) or by using a strain-specific nested primers with respect to the further inner side of the amplification product by a universal primer (multiplex PCR by a plurality of primers may be possible).

Example 6

Detection Method Combining Highly Sensitive Detection Method and One Step Nested PCR Method of Subject to be Detected In addition to the highly sensitive detection method using e-DNAP and the non-display method in accordance with the present invention, by applying the "nested amplification method" or by devising an extension time, with one trial of the nested PCR, more highly sensitive detection can be carried out while a high sensitivity and rapidity are maintained.

(1) Primer Set and Reagent for PCR

Most of commercially available thermostable DNA polymerase produced by using bacteria as a host use *E. coli* as a host thereof. Therefore, when PCR is carried out for detecting strains of *E. coli* or the genus near *E. coli*, a risk of being pseudopositive naturally becomes higher. In order to solve such a problem, and to detect *E. coli* with high sensitivity and high specificity, by applying the "nested amplification method" or by devising an extension time together with the highly sensitive detection method using e-DNAP, the One Step semi-nested PCR using a primer specific to *E. coli* was carried out. The PCR reagent is the same as that in Example 3. Herein, the semi-nested primer set specific to *E. coli* is shown.

```
E. coli specific Forward Primer:
TAACGGCTCACCTAGGCGA           (SEQ ID NO: 58)

E. coli specific Reverse Primer:
GTGGACTACCAGGGTATCTAATCCTG    (SEQ ID NO: 59)

E. coli specific semi-nested Primer:
GCAATATTCCCCACTG              (SEQ ID NO: 60)
```

The primers were designed such that the Tm values of the primers SEQ ID NOs: 58 and 59 were 65° C., respectively, and the Tm value of the semi-nested primer of SEQ ID NO: 60 was 55° C.

(2-1) One Step Nested PCR Method by Applying the "Nested Amplification Method"

The length of the amplification product I by using the primer of SEQ ID NOs: 58 and 59 is 548 bp, and the length of the semi-nested PCR amplification product II is 110 bp. In this way, by clearly differentiating between the lengths of the amplification products, the positions of the primers were designed such that the difference of the Tm values between the amplification products is increased. As a result, the Tm value of the amplification product I was 87° C., and the Tm value of the amplification product II was 83° C. However, since GC % of the amplification product affects the Tm value, in designing primers, GC % of the amplification product must also be considered sufficiently. Furthermore, since the Tm value was affected by the salt concentration of PCR Buffer, the salt concentration should be always constant.

Next, the real-time PCR program was carried out in the conditions described in Table 3. In this condition setting, in addition to the highly sensitive detection method using e-DNAP and the non-display method, the nested PCR can be carried out by one trial by applying the "nested amplification method." In the program, setting of shifting to which the nested primer is bonded is added.

TABLE 3

| Program | Analysis Mode | Cycles | Segment | Target Temperature | Time | Fluorescence Acquisition Mode |
|---|---|---|---|---|---|---|
| Pre-incubation | None | 1 | 1 | 95° C. | 10 min | None |
| Amplification 1 | Quantification | 10 | Denaturation | 94° C. | 15 sec | — |
| | | | Annealing | 70° C. | 2 sec | — |
| | | | Extension | 72° C. | 20 sec | — |
| | | | 1 | 81° C. | 2 sec | single |
| shifting | Quantification | 2 | Denaturation | 94° C. | 10 sec | — |
| | | | Annealing | 60° C. | 2 sec | — |
| | | | Extension | 72° C. | 20 sec | — |
| | | | 1 | 81° C. | 2 sec | single |
| Amplification 2 | Quantification | 40 | Denaturation | 85° C. | 10 sec | — |
| | | | Annealing | 60° C. | 2 sec | — |
| | | | Extension | 72° C. | 20 sec | — |
| | | | 1 | 81° C. | 2 sec | single |
| Melting Curve Analysis | Melting Curves | 1 | Melting | 95° C. 0.1° C./sec. | 0 sec | Continue |
| Cooling | None | 1 | 1 | 40° C. | 30 sec | — |

(2-2) One Step Nested PCR Method by Devising Extension Time

The length of the amplification product I by using the primers of SEQ ID NOs: 58 and 59 is 548 bp, and the length of the semi-nested PCR amplification product II is 110 bp. In this way, the positions of the primers were designed so as to clearly differentiate in the length of the amplification products.

Next, the real-time PCR program was carried out in the conditions described in Table 4. In this condition setting, in addition to the highly sensitive detection method using e-DNAP and the non-display method, the nested PCR can be carried out by one trial by devising the extension time.

TABLE 4

| Program | Analysis Mode | Cycles | Segment | Target Temperature | Time | Fluorescence Acquisition Mode |
| --- | --- | --- | --- | --- | --- | --- |
| Pre-incubation | None | 1 | 1 | 95° C. | 10 min | None |
| Amplification 1 | Quantification | 10 | Denaturation | 94° C. | 15 sec | — |
| | | | Annealing | 70° C. | 2 sec | — |
| | | | Extension | 72° C. | 20 sec | — |
| | | | 1 | 81° C. | 2 sec | single |
| Amplification 2 | Quantification | 40 | Denaturation | 94° C. | 10 sec | — |
| | | | Annealing | 60° C. | 2 sec | — |
| | | | Extension | 72° C. | 2 sec | — |
| | | | 1 | 81° C. | 2 sec | single |
| Melting Curve Analysis | Melting Curves | 1 | Melting | 95° C. 0.1° C./sec. | 0 sec | Continue |
| Cooling | None | 1 | 1 | 40° C. | 30 sec | — |

(3) Results

The real-time PCR was carried out by the following program by mixing three primers including the semi-nested primer to confirm whether only the above-mentioned amplification product I or the amplification product II was amplified by the nested PCR, based on the Tm values of the amplification products or the sizes thereof by applying the "nested amplification method" and designing the extension time.

(3-1) Confirmation that Only Outer Amplification Product I is Amplified

Only the Amplification 1 program part shown in Tables 3 and 4 is tried 50 cycles, respectively. The point is an annealing temperature of 70° C. Since the Tm value of the outer primer is 65° C. and the Tm value of the inner semi-nested primer is 55° C., only the outer primer is bonded in the annealing at 70° C. As a result, only the outer amplification product I is amplified. Experiment results surely show that only an amplification product having a Tm value of the amplification product I of 87° C. and having the length of 548 bp is amplified (FIG. 23(B) and FIG. 25).

(3-2) Confirmation that Only Inner Amplification Product II is Amplified

Only the Amplification 2 program part shown in Tables 3 and 4 is tried 50 cycles, respectively. The point in applying the "nested amplification method" in Table 3 is the annealing temperature of 60° C. and the denaturation temperature of 85° C. In annealing at 60° C., all primers including the semi-nested primer are bonded, but when the denaturation temperature is 85° C., the inner amplification product II (Tm value: 83° C.) is denatured but the outer amplification product I (Tm value: 87° C.) is not denatured. As a result, only the inner amplification product II is amplified. Experiment results surely show that only an amplification product II (others are primer dimers) having 83° C. which are the Tm value and 110 bp is amplified (FIG. 23(A) and FIG. 25).

The point of devising the extension time in Table 4 is the extension time of two seconds. In annealing at 60° C., all the primers including the semi-nested primer are bonded, but when the extension time is two seconds, although the inner amplification product II (110 bp) extends, the outer amplification product I (548 bp) cannot extend. As a result, only the inner amplification product II is amplified. Experiment results surely show that only an amplification product II (others are primer dimers) having 83° C. which are the Tm value and 110 bp is amplified (FIG. 23(A) and FIG. 25).

(3-3) Confirmation of Highly Sensitive Quantification Method Using e-DNAP and Non-Display Method The real-time PCR was carried out according to the program setting in Tables 3 and 4. As a result, only in the presence of E. coli, amplification was observed, and in the presence of distilled water (D.W.), Staphylococcus aureus (S. aureus) and Human DNA, DNA proliferation was not observed at all (FIG. 24(A): only amplification of the amplification 2 of Tables 3 and 4 is shown). That is to say, even after 60 cycles in total, amplification was not observed in other than the case in which E. coli was used, it was confirmed that the highly sensitive quantification can be carried out by using e-DNAP and the non-display method.

(3-4) Confirmation of One Step Nested PCR

A product amplified by using DNA of E. coli as a template through the entire program described in Tables 3 and 4 was only one, and it had the Tm value of 83° C. and the length of 110 bp, that is, only the inner amplification product II was amplified (FIG. 24(B) and FIG. 25). As a result, it was confirmed that the nested PCR can be carried out by one trial (One Step) by applying the "nested amplification method" and by devising the extension time.

(3-5) Conclusion of Results

As a result mentioned above, it was confirmed that when the highly sensitive quantification method is carried out by using e-DNAP and the non-display method, and at the same time, the One Step nested PCR is combined by applying the "nested amplification method" and designing the extension time, a highly specific detection can be carried out by only devising the PCR program while high sensitivity and rapidity can be maintained. According to the nested PCR of these Examples, the primers specific to E. coli are combined, but, for example, a method of combing bacterial universal primers for inside and outside, and a method of using bacterial universal primer for the outside and a species-specific primer for the inside (multiplex PCR using a plurality of specific primers can also be carried out) can be combined. Furthermore, by incorporating both the nested amplification method and devising of the extension time into a PCR program, the One Step nested PCR method can be carried out more reliably.

Example 7

Highly Sensitive Quantification Identification Method for Subject Microorganism to be Detected Using e-DNAP PCR with respect to unknown infectious microorganisms is carried out by using universal primers, and the combination of Tm values of a plurality of amplification products is analyzed, so that the infectious microorganisms are identified rapidly and simply (WO2007/097323). When the infectious microorganism is a bacterium, since the universal primer of a bacterium is used in this identification method, if the e-DNAP is not used, the risk of pseudopositive occurs and therefore highly sensitive detection cannot be carried out. That is to say, it is desirable to use e-DNAP for identification of bacteria in this Example. Furthermore, as measurement equipment, it is desirable to use RotorGene6000 (Qiagen).

(1) Primer Set and Reagent for PCR

As the universal primers of bacteria, SEQ ID NOs: 15 to 28 are used. Thus, seven PCR amplification products can be produced. The reagent for PCR and PCR conditions are the same as those in Example 2.

(2) Analysis Method

After DNA is extracted from a blood sample of a septicemia patient, the above-mentioned real-time PCR is tried so as to obtain a Tm value of each of the seven PCR amplification products. The combination of the seven PCR amplification products is collated with the following database. At this time, quantification results by the trial of the real-time PCR can be obtained.

(3) Database

The combinations of the seven Tm values as to each of the 45 types of bacteria extracted from positive samples of septicemia for the past one year in Toyama University Hospital have been input. The seven Tm values are obtained by using primers of SEQ ID NOs: 15 to 28 and by using the reagent for PCR and PCR conditions that are the same as those in Example 2.

(4) Identification Method

The average value of seven Tm values obtained from patient samples is calculated, and a relative value is calculated from the average value (since this value is not an absolute value, plus/minus is generated). The seven relative values are denoted by $D1_{ref}$ to $D7_{ref}$. Similarly, the values are calculated as to each of the bacteria in the database, the seven relative values are denoted by $D1_{db}$ to $D7_{db}$. Then, as to all the bacteria in the database, the following calculation is carried out.

$$\text{Dist.} = \sqrt{(D1_{db}-D1_{ref})^2 + (D2_{db}-D2_{ref})^2 + \ldots + (D7_{db}-D7_{ref})^2}$$ [Expression 2]

A bacterium having the "Dist." that is closest to 0 is derived from the database, and this bacterium is identified to be a causative bacterium in the sample. Since the above-mentioned method is incorporated in an algorithm of the identification software of the computer, only by inputting the seven Tm values obtained from the patient samples, the identification results can be obtained instantly. By using the algorithm of this Example, measurement errors of the Tm value for every trial are completely corrected. In other words, even if an error of the temperature occurs for every measurement, such an error does not affect the identification. An error that cannot be corrected by this method is an error in measurement occurring between samples in the same trial. However, for example, when RotorGene6000 (Qiagen) as one of the real-time PCR equipment is used, since a measurement error between the samples is ±0.01° C., the error hardly affect identification, and therefore accurate identification can be carried out.

(5) Results

The seven Tm values in unknown bacteria obtained from patient samples were 84.98, 84.45, 84.84, 84.31, 81.20, 81.83, and 81.12, respectively. As a result of the calculation by the identification software, *Klebsiella pneumoniae* having Dist. of 0.05 was able to be instantly identified as a causative bacterium that is the closest to Dist.=0 (Table 5: calculation results by identification software). Furthermore, quantification was possible.

TABLE 5

| User: | user | | Name | Tryal | Dist. | Ave. | Std. | Bac. 1 | Bac. 2 | Bac. 3 | Bac. 4 | Bac. 5 | Bac. 6 | Bac. 7 |
|---|---|---|---|---|---|---|---|---|---|---|---|---|---|---|
| Bac. 1 | 84.98 | Info | *Kiebsiella pneumoniae* | 1 | 0.05 | 83.26 | | 85.02 | 84.48 | 84.85 | 84.29 | 81.20 | 81.84 | 81.14 |
| Bac. 2 | 84.45 | Info | *Enterobacter cloacae* | 1 | 0.26 | 83.25 | | 84.85 | 84.39 | 84.84 | 84.27 | 81.41 | 81.81 | 81.15 |
| Bac. 3 | 84.84 | Info | *Klebsiella okytoca* | 1 | 0.85 | 82.90 | | 84.84 | 83.46 | 84.43 | 83.84 | 81.08 | 81.42 | 81.21 |
| Bac. 4 | 84.31 | Info | *Citrobacter Freundii* | 1 | 0.89 | 83.46 | | 85.04 | 84.14 | 84.96 | 84.91 | 81.12 | 82.32 | 81.75 |
| Bac. 5 | 81.20 | Info | *Serratia marcescens* | 1 | 1.24 | 83.13 | | 84.76 | 83.82 | 84.27 | 84.01 | 80.92 | 82.48 | 81.65 |
| Bac. 6 | 81.83 | Info | *S. capitis.* Subsp. *capitis* | 1 | 1.39 | 82.06 | | 83.65 | 82.37 | 83.10 | 83.64 | 80.12 | 81.31 | 80.24 |
| Bac. 7 | 81.12 | Info | *Enterobacter aerogenes* | 1 | 1.41 | 83.18 | | 84.72 | 83.34 | 84.82 | 84.74 | 80.95 | 82.50 | 81.22 |
| Fungi | | Info | *Staphylococcus epidermidis* | 1 | 1.59 | 82.25 | | 83.63 | 82.59 | 83.10 | 83.75 | 80.67 | 81.61 | 80.41 |
| spa | | Info | *Staphylococcus epidermidis* (MRSE) | 1 | 1.59 | 82.25 | | 83.63 | 82.59 | 83.10 | 83.75 | 80.67 | 81.61 | 80.41 |
| mecA | | Info | *Staphylococcus hominis* | 1 | 1.70 | 82.12 | | 83.05 | 82.92 | 83.00 | 83.77 | 79.87 | 81.44 | 80.79 |
| Display Line Count | 10 | | | | | | | | | | | | | |
| Limit Distance Search | 2.50 | | | | | | | | | | | | | |

Furthermore, from the usual examination of bacteria, it was confirmed that *Klebsiella pneumonia* is detected from the patient sample, and that the identification result is the same as that by the usual method.

Note here that seven Tm values in the database of the *Klebsiella pneumonia* were 85.02, 84.48, 84.45, 84.29, 81.20, 81.84, and 81.14, respectively.

The identification method of this Example can be used for not only identification of bacteria but also identification of fungi and other organism species. Furthermore, it is clinically useful to examine the presence or absence of an antibiotic agent-resistant gene such as mecA together.

Industrial Applicability

A quantification and/or identification method of an organism to be detected in accordance with the present invention is applicable to daily life water examinations, food examinations, septicemia examinations, drug sensitivity tests, and the like. Basically, the method is applicable to any other samples which should be sterile and are related to infection. For example, it is thought that examinations of the cerebrospinal fluid, the amniotic fluid (intrauterine infection), and the like, have high social contribution, and the rapidity of this system (results are determined within two hours) is particularly useful.

Furthermore, wide range of practical use is possible not only in examinations in the field related to human, but also in examinations in the field of veterinarian, for example, infection of domestic animals, or examinations in an organism experiment environment, for example, contamination in cell culture solutions.

The invention claimed is:

1. A detection method for a subject organism to be detected in a sample, comprising:
   (1) an amplification step of performing a nucleic acid amplification reaction using nucleic acid prepared from the sample, primers for amplifying an intended gene specific for the subject organism to be detected, and a thermostable DNA polymerase preparation; and
   (2) a detection step of detecting an amplification product of the intended gene in amplification products in the amplification step,
   wherein the thermostable DNA polymerase preparation is the following (b):
      (b) a thermostable DNA polymerase preparation, wherein:
      (b-1) the thermostable DNA polymerase has contamination with 10 fg or less of bacterially-derived nucleic acid other than a gene encoding the thermostable DNA polymerase based on 1 unit of the thermostable DNA polymerase, and
      (b-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

2. The detection method according to claim 1, wherein the amplification products of the amplification step are quantified in the detection step and the subject organism to be detected in the sample is quantified from the quantification results obtained.

3. A quantification and/or identification method for a subject organism to be detected in a sample, comprising:
   (1) a first amplification step of performing a nucleic acid amplification reaction using nucleic acid prepared from the sample, primers, (B) and (M), for amplifying an intended gene specific for the subject organism to be detected, and a thermostable DNA polymerase preparation,
   (2) a first quantification and/or identification step of analyzing a combination of melting temperatures (Tm values) of a plurality of (3 to 10) amplification products in the first amplification step based on a combination of melting temperatures (Tm values) specific for amplification products of the intended gene to perform the quantification and/or identification of the subject organism to be detected in the sample,
   (3) a second amplification step of performing a nucleic acid amplification reaction using nucleic acid prepared from the sample, primers, (F), for amplifying an intended gene specific for the subject organism to be detected, and a thermostable DNA polymerase preparation produced using a bacterium as a host, and
   (4) a second quantification and/or identification step of analyzing a combination of melting temperatures (Tm values) of a plurality of (3 to 10) amplification products in the second amplification step based on a combination of melting temperatures (Tm values) specific for amplification products of the intended gene to quantify the amplification products in the first quantification and/or identification step of quantifying and/or identifying the subject organism to be detected and the second amplification step to perform the quantification and/or identification of the subject organism to be detected in the sample from the quantification results obtained,
   wherein the primers (B), (F) and (M) are:
   (B) a universal primer set capable of amplifying a plurality of regions of a gene of a bacterium and primers containing all or ⅓ or more of each of the base sequences of the primers,
   (F) a universal primer set capable of amplifying a plurality of regions of a gene of a fungus and primers containing all or ⅓ or more of each of the base sequences of the primers, and
   (M) a primer set specifically amplifying an antibiotic resistance gene reflecting an epidemic of the time such as a mec A gene exhibiting methicillin resistance
   wherein the thermostable DNA polymerase preparation in the first amplification step is the following (b):
      (b) a thermostable DNA polymerase preparation, wherein:
      (b-1) the thermostable DNA polymerase has contamination with 10 fg or less of bacterially-derived nucleic acid other than a gene encoding the thermostable DNA polymerase based on 1 unit of the thermostable DNA polymerase, and
      (b-2) no amplification products of the bacterially-derived nucleic acid are detected even when 32 cycles or more of gene amplification reaction are performed in the preparation under conditions containing no template using primers capable of amplifying only the bacterially-derived nucleic acid other than a gene encoding the thermostable DNA polymerase.

4. A quantification and/or identification method for a subject organism to be detected in a sample, comprising:
   (1) a first amplification step of performing a nucleic acid amplification reaction using nucleic acid prepared from the sample, primers, (B), for amplifying an intended gene specific for the subject organism to be detected, and a thermostable DNA polymerase preparation,
   (2) a first quantification and/or identification step of analyzing a combination of melting temperatures (Tm values) of a plurality of (3 to 10) amplification products in the first amplification step based on a combination of melting temperatures (Tm values) specific for amplification products of the intended gene to perform the quantification and/or identification of the subject organism to be detected in the sample,
   (3) a second amplification step of performing a nucleic acid amplification reaction using nucleic acid prepared from the sample, primers, (F), for amplifying an intended gene specific for the subject organism to be detected, and a thermostable DNA polymerase preparation produced using a bacterium as a host, (4) a second quantification and/or identification step of analyzing a combination of melting temperatures (Tm values) of a plurality of (3 to 10) amplification products in the second amplification step based on a combination of melting temperatures (Tm values) specific for amplification products of the intended gene to quantify the amplification products in the first quantification and/or identification step of quantifying and/or identifying the subject organism to be detected and the second amplification step to perform the quantification and/or identification of the subject organism to be detected in the sample from the quantification results obtained, (5) a third amplification step of performing a nucleic acid amplification reaction using nucleic acid prepared from the sample, primers, (M), for amplifying an intended gene specific for the subject organism to be detected, and a thermostable DNA polymerase preparation, and (6) a third quantification and/or identification step of analyzing melting temperatures (Tm values) of amplification products in the third amplification step based on melting temperatures (Tm values) specific for amplification products of the intended gene to perform the quantification and/or identification of the subject organism to be detected in the sample, wherein the primers (B), (F) and (M) are:

(B) a universal primer set capable of amplifying a plurality of regions of a gene of a bacterium and primers containing all or ⅓ or more of each of the base sequences of the primers, (F) a universal primer set capable of amplifying a plurality of regions of a gene of a fungus and primers containing all or ⅓ or more of each of the base sequences of the primers, and (M) a primer set specifically amplifying an antibiotic resistance gene reflecting an epidemic of the time such as a mecA gene exhibiting methicillin resistance wherein the thermostable DNA polymerase preparations in the first and third amplification steps are independently the following (b):

(b) a thermostable DNA polymerase preparation, wherein:

(b-1) the thermostable DNA polymerase has contamination with 10 fg or less of bacterially-derived nucleic acid other than a gene encoding the thermostable DNA polymerase based on 1 unit of the thermostable DNA polymerase, and (b-2) no amplification products of the bacterially-derived nucleic acid are detected even when 32 cycles or more of gene amplification reaction are performed in the preparation under conditions containing no template using primers capable of amplifying only the bacterially-derived nucleic acid other than a gene encoding the thermostable DNA polymerase.

5. The quantification and/or identification method according to claim 3, wherein amplification regions of the gene of a bacterium are 3 to 10 regions of the 16S rRNA gene.

6. The quantification and/or identification method according to claim 3, wherein amplification regions of the gene of a fungus are 3 to 10 regions of the 18S rRNA gene.

7. The quantification and/or identification method according to claim 3, further comprising the step of correcting the measurement errors of the Tm values of the amplification products by using a constant concentration of DNA of a standard strain of *Escherichia coli* as a template for a standard control to measure a standard Tm value each time using any one of a universal primer set capable of amplifying a plurality of regions of a gene of a bacterium and a primer set containing all or part of each of the base sequences of the primers.

8. The quantification and/or identification method according to claim 3, wherein the combination of melting temperatures ($Tm^{M1}$ to $Tm^{MN}$:N=3 to 10) of the amplification products based on the amplification regions are analyzed on the basis of the combination of melting temperatures ($Tm^{S1}$ to $Tm_{Sn}$:n=3 to 10) specific for the subject organism to be detected to quantify and/or identify the subject organism to be detected.

9. The quantification and/or identification method according to claim 8, further comprising the step of minimizing the influence of the measurement errors by identifying the subject organism to be detected using not only combinations of the Tm values but also combinations of differences between the Tm values for an algorithm for identifying the organism.

10. The quantification and/or identification method according to claim 4, wherein amplification regions of the gene of the bacterium are 3 to 10 regions of the 16S rRNA gene.

11. The quantification and/or identification method according to claim 4, wherein amplification regions of the gene of the fungus are 3 to 10 regions of the 18S rRNA gene.

12. The quantification and/or identification method according to claim 4, further comprising the step of correcting the measurement errors of the Tm values of the amplification products by using a constant concentration of DNA of a standard strain of *Escherichia coli* as a template for a standard control to measure a standard Tm value each time using any one of a primer set capable of amplifying a plurality of regions of the 16S rRNA genes of all bacteria and a primer set containing all or part of each of the base sequences of the primers.

13. The quantification and/or identification method according to claim 4, wherein the combination of melting temperatures ($Tm^{M1}$ to $Tm^{MN}$:N=3 to 10) of the amplification products based on the amplification regions are analyzed on the basis of the combination of melting temperatures ($Tm^{S1}$ to $Tm^{Sn}$:n=3 to 10) specific for the subject organism to be detected to quantify and/or identify the subject organism to be detected.

14. The quantification and/or identification method according to claim 13, further comprising the step of minimizing the influence of the measurement errors by identifying the subject organism to be detected using not only combinations of the Tm values but also combinations of differences between the Tm values for an algorithm for identifying the organism.

15. A detection method for an intended nucleic acid to be detected in a sample, comprising:

(1) an amplification step of performing a nucleic acid amplification reaction using nucleic acid prepared from the sample, primers for amplifying an intended nucleic acid to be detected, and a thermostable DNA polymerase preparation; and (2) a detection step of detecting the intended nucleic acid in amplification products in the amplification step, wherein the thermostable DNA polymerase preparation is the following (b):

(b) a thermostable DNA polymerase preparation, wherein:

(b-1) the thermostable DNA polymerase has contamination with 10 fg or less of bacterially-derived nucleic acid other than a gene encoding the thermostable DNA polymerase based on 1 unit of the thermostable DNA polymerase, and (b-2) no amplification products of the bacterially-derived nucleic acid are detected even when 32 cycles or more of gene amplification reaction are performed in the preparation under conditions containing no template using primers capable of amplifying only the bacterially-derived nucleic acid other than the gene encoding the thermostable DNA polymerase.

* * * * *

SEQUENCE LISTING

<160> NUMBER OF SEQ ID NOS: 95

<210> SEQ ID NO 1
<211> LENGTH: 2522
<212> TYPE: DNA
<213> ORGANISM: Thermus aquaticus
<220> FEATURE:
<223> OTHER INFORMATION: Gene encoding thermal resistant DNA polymerase
      derived from Thermus aquaticus

<400> SEQUENCE: 1

```
aagcttacgt atacaacatg agaggtatgc ttccattgtt cgaacctaaa ggtagagtat      60
tgttggttga tggtcatcat ctagcttaca gaactttcca cgctctaaaa ggtttaacaa     120
catcaagagg tgaacctgtt caagctgtat acggttttgc taagtcttta ctaaaagcat     180
tgaaggaaga cggtgacgcc gttattgttg ttttcgatgc taaggcacca agttttagac     240
atgaagcata cggtggttat aaggctggaa gagcaccaac tcctgaagac ttccctagac     300
aattggcact aatcaaggaa ctagtcgact tactaggtct tgcaagatta gaagtcccag     360
gttatgaggc agatgatgta ctagcctctt tagcaaagaa ggcagaaaag gagggttatg     420
aagttagaat tttaaccgct gataaggact tatatcaatt gctatctgat aggattcatg     480
tgttacaccc tgaaggttat ttgataactc cagcttggtt atgggagaag tacggtttga     540
ggccagacca atgggccgat tatagagctt taaccggcga cgagtcagac aatcttccag     600
gtgttaaagg aattggcgaa aagactgcta ggaagttgtt ggaagagtgg ggctccttgg     660
aggccttact taaaaatttg gacaggctaa aaccagcaat cagggaaaag atactagctc     720
acatggatga tcttaaattg tcttgggact tagccaaggt cagaactgat ttgcctttag     780
aggtcgactt cgctaagaga agggaacctg atagggaaag gttaagagcc ttcttggaaa     840
gacttgagtt tggatcatta ttgcatgaat ttggtttatt agaatcccct aaggccttgg     900
aagaagcacc atggccacct ccagaaggtg cctttgtagg cttcgtctta agcaggaaag     960
aaccaatgtg ggcagactta ttggctctag ctgctgccag aggaggaaga gtgcatagag    1020
ccccagaacc atataaagcc ttgagagact tgaaggaagc aagaggtttg ttagctaaag    1080
atttgagcgt attagccttg agggaaggtt taggactacc accaggtgac gacccaatgt    1140
tgcttgctta tttgcttgat ccatcaaaca caacacctga aggagtagct agaaggtatg    1200
gtggagaatg gactgaagag gctggagaga gagccgctct atctgagaga ttgtttgcta    1260
atttgtgggg tagacttgaa ggtgaggaaa gattgttgtg gctatacagg gaagtagaaa    1320
ggccattatc tgcagtattg gctcatatgg aggccacagg cgttagatta gatgttgctt    1380
```

```
acttaagagc tttgtcattg gaagtcgccg aagaaattgc aagacttgaa gctgaggtgt      1440
tcagacttgc cggtcatcca ttcaatctta atagtagaga ccagctagaa agagtgttat      1500
tcgacgagct tggattacca gcaatcggaa agacagaaaa gactggtaaa aggtctacaa      1560
gtgccgccgt tttggaagca ttagggaggg cccatccaat tgttgaaaag atattgcagt      1620
atagagaatt gacaaaatta aaatcaactt atatcgatcc acttccagac ttaatccatc      1680
caaggacagg cagattacac accaggttta accagaccgc aactgctaca ggcagattat      1740
catcttcaga tcctaactta caaaacattc ctgtaaggac tccactaggt cagagaatta      1800
gaagagcttt tatcgctgag gaaggctggt tgcttgtggc tttagattat agtcaaattg      1860
agttaagggt cttggctcac ttgtctggtg acgaaaatct tatcagagtt tttcaggaag      1920
gtagggatat acatacagag accgcctcat ggatgtttgg tgttccaagg gaggccgtcg      1980
atccactaat gaggagagca gccaaaacta ttaactttgg agtattgtat ggtatgagtg      2040
ctcacagatt atcccaagag ttggccatcc cttacgagga agcacaggct tttatagaaa      2100
ggtatttcca gtcttttcct aaggttagag catggattga aaagacacta gaggaaggta      2160
ggaggagggg ttacgtggag accttattcg gaagaaggag atacgttcca gacttagagg      2220
ctagagtgaa atcagttaga gaagccgcag agagaatggc attcaatatg ccagtacaag      2280
gcactgccgc agatttgatg aaactagcca tggttaagct atttccaaga ttggaagaaa      2340
tgggagctag aatgctatta caagttcatg atgaacttgt tttagaggct cctaaagaaa      2400
gggctgaagc agtggccagg ttagctaaag aagtaatgga gggcgtttac ccattggcag      2460
ttcctttaga ggtcgaagtg ggtataggtg aagactggct atctgcaaag gaataagaat      2520
tc                                                                    2522

<210> SEQ ID NO 2
<211> LENGTH: 21
<212> TYPE: DNA
<213> ORGANISM: Artificial Sequence
<220> FEATURE:
<223> OTHER INFORMATION: Reverse Primer

<400> SEQUENCE: 2
cccgtcaatt cctttgagtt t                                               21

<210> SEQ ID NO 3
<211> LENGTH: 21
<212> TYPE: DNA
<213> ORGANISM: Artificial Sequence
<220> FEATURE:
<223> OTHER INFORMATION: Forward Primer

<400> SEQUENCE: 3
aaactcaaag gaattgacgg g                                               21

<210> SEQ ID NO 4
<211> LENGTH: 15
<212> TYPE: DNA
<213> ORGANISM: Artificial Sequence
<220> FEATURE:
<223> OTHER INFORMATION: Reverse Primer

<400> SEQUENCE: 4
cgctcgttgc gggac                                                      15
```

-continued

```
<210> SEQ ID NO 5
<211> LENGTH: 15
<212> TYPE: DNA
<213> ORGANISM: Artificial Sequence
<220> FEATURE:
<223> OTHER INFORMATION: Forward Primer

<400> SEQUENCE: 5
gtcccgcaac gagcg                                                          15

<210> SEQ ID NO 6
<211> LENGTH: 21
<212> TYPE: DNA
<213> ORGANISM: Artificial Sequence
<220> FEATURE:
<223> OTHER INFORMATION: Reverse Primer

<400> SEQUENCE: 6
attgtagcac gtgtgtagcc c                                                   21

<210> SEQ ID NO 7
<211> LENGTH: 21
<212> TYPE: DNA
<213> ORGANISM: Artificial Sequence
<220> FEATURE:
<223> OTHER INFORMATION: Forward Primer

<400> SEQUENCE: 7
gggctacaca cgtgctacaa t                                                   21

<210> SEQ ID NO 8
<211> LENGTH: 17
<212> TYPE: DNA
<213> ORGANISM: Artificial Sequence
<220> FEATURE:
<223> OTHER INFORMATION: Reverse Primer

<400> SEQUENCE: 8
ccgggaacgt attcacc                                                        17

<210> SEQ ID NO 9
<211> LENGTH: 28
<212> TYPE: DNA
<213> ORGANISM: Artificial Sequence
<220> FEATURE:
<223> OTHER INFORMATION: Forward Primer

<400> SEQUENCE: 9
gaatgagtac aatgtaaata ccttaacg                                            28

<210> SEQ ID NO 10
<211> LENGTH: 25
<212> TYPE: DNA
<213> ORGANISM: Artificial Sequence
<220> FEATURE:
<223> OTHER INFORMATION: Reverse Primer

<400> SEQUENCE: 10
taactgcaac aactttaata tacgc                                               25

<210> SEQ ID NO 11
<211> LENGTH: 16
<212> TYPE: DNA
<213> ORGANISM: Artificial Sequence
<220> FEATURE:
<223> OTHER INFORMATION: Forward Primer
```

<400> SEQUENCE: 11
ctcctacggg aggcag                                                        16

<210> SEQ ID NO 12
<211> LENGTH: 22
<212> TYPE: DNA
<213> ORGANISM: Artificial Sequence
<220> FEATURE:
<223> OTHER INFORMATION: Reverse Primer

<400> SEQUENCE: 12
actaccaggg tatctaatcc tg                                                 22

<210> SEQ ID NO 13
<211> LENGTH: 30
<212> TYPE: DNA
<213> ORGANISM: Artificial Sequence
<220> FEATURE:
<223> OTHER INFORMATION: Forward Primer

<400> SEQUENCE: 13
attataaagc aatcgctaaa gaactaagta                                         30

<210> SEQ ID NO 14
<211> LENGTH: 26
<212> TYPE: DNA
<213> ORGANISM: Artificial Sequence
<220> FEATURE:
<223> OTHER INFORMATION: Reverse Primer

<400> SEQUENCE: 14
ccaataactg catcatcttt atagcc                                             26

<210> SEQ ID NO 15
<211> LENGTH: 20
<212> TYPE: DNA
<213> ORGANISM: Artificial Sequence
<220> FEATURE:
<223> OTHER INFORMATION: Forward Primer

<400> SEQUENCE: 15
agagtttgat catggctcag                                                    20

<210> SEQ ID NO 16
<211> LENGTH: 18
<212> TYPE: DNA
<213> ORGANISM: Artificial Sequence
<220> FEATURE:
<223> OTHER INFORMATION: Reverse Primer

<400> SEQUENCE: 16
cgtaggagtc tggaccgt                                                      18

<210> SEQ ID NO 17
<211> LENGTH: 17
<212> TYPE: DNA
<213> ORGANISM: Artificial Sequence
<220> FEATURE:
<223> OTHER INFORMATION: Forward Primer

<400> SEQUENCE: 17
gactcctacg ggaggca                                                       17

```
<210> SEQ ID NO 18
<211> LENGTH: 17
<212> TYPE: DNA
<213> ORGANISM: Artificial Sequence
<220> FEATURE:
<223> OTHER INFORMATION: Reverse Primer

<400> SEQUENCE: 18
tattaccgcg gctgctg                                                      17

<210> SEQ ID NO 19
<211> LENGTH: 16
<212> TYPE: DNA
<213> ORGANISM: Artificial Sequence
<220> FEATURE:
<223> OTHER INFORMATION: Forward Primer

<400> SEQUENCE: 19
agcagccgcg gtaata                                                       16

<210> SEQ ID NO 20
<211> LENGTH: 23
<212> TYPE: DNA
<213> ORGANISM: Artificial Sequence
<220> FEATURE:
<223> OTHER INFORMATION: Reverse Primer

<400> SEQUENCE: 20
ggactaccag ggtatctaat cct                                               23

<210> SEQ ID NO 21
<211> LENGTH: 23
<212> TYPE: DNA
<213> ORGANISM: Artificial Sequence
<220> FEATURE:
<223> OTHER INFORMATION: Forward Primer

<400> SEQUENCE: 21
aacaggatta gataccctgg tag                                               23

<210> SEQ ID NO 22
<211> LENGTH: 21
<212> TYPE: DNA
<213> ORGANISM: Artificial Sequence
<220> FEATURE:
<223> OTHER INFORMATION: Reverse Primer

<400> SEQUENCE: 22
aattaaacca catgctccac c                                                 21

<210> SEQ ID NO 23
<211> LENGTH: 21
<212> TYPE: DNA
<213> ORGANISM: Artificial Sequence
<220> FEATURE:
<223> OTHER INFORMATION: Forward Primer

<400> SEQUENCE: 23
tggtttaatt cgatgcaacg c                                                 21

<210> SEQ ID NO 24
<211> LENGTH: 17
<212> TYPE: DNA
<213> ORGANISM: Artificial Sequence
<220> FEATURE:
<223> OTHER INFORMATION: Reverse Primer
```

<400> SEQUENCE: 24
gagctgacga cagccat    17

<210> SEQ ID NO 25
<211> LENGTH: 16
<212> TYPE: DNA
<213> ORGANISM: Artificial Sequence
<220> FEATURE:
<223> OTHER INFORMATION: Forward Primer

<400> SEQUENCE: 25
ttgggttaag tcccgc    16

<210> SEQ ID NO 26
<211> LENGTH: 16
<212> TYPE: DNA
<213> ORGANISM: Artificial Sequence
<220> FEATURE:
<223> OTHER INFORMATION: Reverse Primer

<400> SEQUENCE: 26
cgtcatcccc accttc    16

<210> SEQ ID NO 27
<211> LENGTH: 20
<212> TYPE: DNA
<213> ORGANISM: Artificial Sequence
<220> FEATURE:
<223> OTHER INFORMATION: Forward Primer

<400> SEQUENCE: 27
ggctacacac gtgctacaat    20

<210> SEQ ID NO 28
<211> LENGTH: 17
<212> TYPE: DNA
<213> ORGANISM: Artificial Sequence
<220> FEATURE:
<223> OTHER INFORMATION: Reverse Primer

<400> SEQUENCE: 28
ccgggaacgt attcacc    17

<210> SEQ ID NO 29
<211> LENGTH: 26
<212> TYPE: DNA
<213> ORGANISM: Artificial Sequence
<220> FEATURE:
<223> OTHER INFORMATION: Forward Primer

<400> SEQUENCE: 29
gtggtaattc tagagctaat acatgc    26

<210> SEQ ID NO 30
<211> LENGTH: 17
<212> TYPE: DNA
<213> ORGANISM: Artificial Sequence
<220> FEATURE:
<223> OTHER INFORMATION: Reverse Primer

<400> SEQUENCE: 30
ggtagccgtt tctcagg    17

```
<210> SEQ ID NO 31
<211> LENGTH: 19
<212> TYPE: DNA
<213> ORGANISM: Artificial Sequence
<220> FEATURE:
<223> OTHER INFORMATION: Forward Primer

<400> SEQUENCE: 31
gcctgagaaa cggctacca                                                  19

<210> SEQ ID NO 32
<211> LENGTH: 22
<212> TYPE: DNA
<213> ORGANISM: Artificial Sequence
<220> FEATURE:
<223> OTHER INFORMATION: Reverse Primer

<400> SEQUENCE: 32
cctccaattg ttcctcgtta ag                                              22

<210> SEQ ID NO 33
<211> LENGTH: 22
<212> TYPE: DNA
<213> ORGANISM: Artificial Sequence
<220> FEATURE:
<223> OTHER INFORMATION: Forward Primer

<400> SEQUENCE: 33
ttaacgagga acaattggag gg                                              22

<210> SEQ ID NO 34
<211> LENGTH: 23
<212> TYPE: DNA
<213> ORGANISM: Artificial Sequence
<220> FEATURE:
<223> OTHER INFORMATION: Reverse Primer

<400> SEQUENCE: 34
gcctgctttg aacactctaa ttt                                             23

<210> SEQ ID NO 35
<211> LENGTH: 21
<212> TYPE: DNA
<213> ORGANISM: Artificial Sequence
<220> FEATURE:
<223> OTHER INFORMATION: Forward Primer

<400> SEQUENCE: 35
ataccgtcgt agtcttaacc a                                               21

<210> SEQ ID NO 36
<211> LENGTH: 24
<212> TYPE: DNA
<213> ORGANISM: Artificial Sequence
<220> FEATURE:
<223> OTHER INFORMATION: Reverse Primer

<400> SEQUENCE: 36
gtcaattcct ttaagtttca gcct                                            24

<210> SEQ ID NO 37
<211> LENGTH: 19
<212> TYPE: DNA
<213> ORGANISM: Artificial Sequence
<220> FEATURE:
<223> OTHER INFORMATION: Forward Primer
```

```
<400> SEQUENCE: 37
catggccgtt cttagttgg                                                  19

<210> SEQ ID NO 38
<211> LENGTH: 18
<212> TYPE: DNA
<213> ORGANISM: Artificial Sequence
<220> FEATURE:
<223> OTHER INFORMATION: Reverse Primer

<400> SEQUENCE: 38
gggcatcaca gacctgtt                                                   18

<210> SEQ ID NO 39
<211> LENGTH: 19
<212> TYPE: DNA
<213> ORGANISM: Artificial Sequence
<220> FEATURE:
<223> OTHER INFORMATION: Forward Primer

<400> SEQUENCE: 39
aggtctgtga tgcccttag                                                  19

<210> SEQ ID NO 40
<211> LENGTH: 17
<212> TYPE: DNA
<213> ORGANISM: Artificial Sequence
<220> FEATURE:
<223> OTHER INFORMATION: Reverse Primer

<400> SEQUENCE: 40
cgggcggtgt gtacaaa                                                    17

<210> SEQ ID NO 41
<211> LENGTH: 2499
<212> TYPE: DNA
<213> ORGANISM: Thermus aquaticus
<220> FEATURE:
<223> OTHER INFORMATION: Gene encoding thermal resistant DNA polymerase
      derived from Thermus aquaticus

<400> SEQUENCE: 41
atgagaggca tgctgccact gttcgagcca aagggaaggg tgctgctggt ggacggacac      60
catctggcct acagaacttt tcacgctctg aagggactga ccacatcacg ggggagcca      120 gtgcaggctg tgtatggatt cgctaaaagc ctgctgaagg ccctgaaaga ggacggagat     180
gctgtgatcg tggtgttcga tgctaaggcc cctagcttta acatgaggc ctacggcgga     240 tataaagccg acgcgctcc aaccccgag gactttccaa ggcagctggc cctgattaag      300
gaactggtgg atctgctggg actggctagg ctggaggtgc ccggctacga agctgacgat    360
gtgctggcct ccctggctaa gaaagccgag aggaaggct acgaggtgcg catcctgaca    420
gccgacaaag atctgtatca gctgctgtct gacaggatcc acgtgctgca tcccgagggg    480
tatctgatta ctcctgcctg gctgtgggaa aagtacggcc tgagaccaga ccagtgggct    540
gattatcggg ccctgactgg cgacgagtca gataacctgc ccggagtgaa aggcatcgga    600
gaaaaaaccg ccaggaagct gctggaggaa tggggcagcc tggaggctct gctgaaaaat    660
ctggatagac tgaagcccgc catccgggag aaaattctgg ctcacatgga cgatctgaag    720
ctgtcttggg acctggccaa agtgagaacc gacctgcctc tggaggtgga tttcgccaag    780
```

| | |
|---|---|
| aggagagagc cagatcggga acgcctgagg gctttcctgg agcggctgga atttgggtca | 840 |
| ctgctgcatg agtttggcct gctggaaagc ccaaaggctc tggaggaagc tccatggcca | 900 |
| cctccagagg gagccttcgt gggatttgtg ctgtccagga agaaccaat gtgggctgac | 960 |
| ctgctggctc tggctgctgc cagaggggga cgggtgcacc gcgcccctga gccatacaag | 1020 |
| gctctgcgcg acctgaaaga agccagggggg ctgctggcta aggatctgtc agtgctggct | 1080 |
| ctgagggagg gactgggact gcccctggc gacgatccaa tgctgctggc ctacctgctg | 1140 |
| gatccaagca acactacccc agagggagtg gctaggagat atggagggga atggaccgag | 1200 |
| gaagctgggg agagagctgc cctgtccgaa cggctgttcg ctaatctgtg ggaaggctg | 1260 |
| gagggagagg aaaggctgct gtggctgtac cgggaggtgg aacgccctct gtccgctgtg | 1320 |
| ctggctcaca tggaggctac aggcgtgcgc ctggacgtgg cttatctgag ggccctgtct | 1380 |
| ctggaggtgg ctgaggaaat cgccagactg gaggctgaag tgttccggct ggccggacat | 1440 |
| ccctttaacc tgaatagcag ggaccagctg gagagagtgc tgttcgatga actggggctg | 1500 |
| cctgccattg gcaagaccga gaaacaggg aagcgctcaa caagcgctgc tgtgctggag | 1560 |
| gctctgaggg aagctcaccc catcgtggag aagattctgc agtacagaga actgactaag | 1620 |
| ctgaaatcca cctatatcga cccctgcct gatctgattc ccctaggac aggcagactg | 1680 |
| catactcgct tcaaccagac agctactgcc accggaaggc tgagctcctc tgacccaaac | 1740 |
| ctgcagaata tccctgtgag aaccccactg ggacagcgga tcaggagagc ttttattgct | 1800 |
| gaggaaggat ggctgctggt ggctctggat tactcccaga ttgagctgag ggtgctggct | 1860 |
| cacctgtctg ggacgaaaa cctgatccgc gtgttccagg agggcaggga tattcataca | 1920 |
| gaaactgcca gctggatgtt tggagtgcct cgcgaggctg tggacccact gatgaggagg | 1980 |
| gctgccaaga caatcaattt cggagtgctg tatgggatgt ccgcccacag gctgtctcag | 2040 |
| gagctggcta tccctacga ggaagctcag gccttcatcg aaagatactt ccagtctttc | 2100 |
| cctaaggtgc gggcctggat tgagaaaacc ctggaggaag gcaggagacg gggatacgtg | 2160 |
| gaaacactgt tcggccgcag gagatatgtg cctgacctgg aggccagggt gaagtcagtg | 2220 |
| cgcgaggctg ccgaaaggat ggctttcaat atgcctgtgc agggaaccgc tgccgacctg | 2280 |
| atgaaactgg ccatggtgaa gctgtttcca cgcctggagg aaatgggggc taggatgctg | 2340 |
| ctgcaggtgc atgatgagct ggtgctggaa gccccaaagg agagagctga gccgtggct | 2400 |
| cggctggcca agaagtgat ggaaggcgtg tacccctgg ctgtgcctct ggaggtggaa | 2460 |
| gtgggaatcg gggaggactg gctgtccgcc aaggaatga | 2499 |

<210> SEQ ID NO 42

<400> SEQUENCE: 42

000

<210> SEQ ID NO 43
<211> LENGTH: 23
<212> TYPE: DNA
<213> ORGANISM: Artificial Sequence
<220> FEATURE:
<223> OTHER INFORMATION: Forward Primer

<400> SEQUENCE: 43
caaactacgg taacattgat cgc        23

```
<210> SEQ ID NO 44
<211> LENGTH: 22
<212> TYPE: DNA
<213> ORGANISM: Artificial Sequence
<220> FEATURE:
<223> OTHER INFORMATION: Reverse Primer

<400> SEQUENCE: 44
atgtatgctt tggtctttct gc                                              22

<210> SEQ ID NO 45
<211> LENGTH: 23
<212> TYPE: DNA
<213> ORGANISM: Artificial Sequence
<220> FEATURE:
<223> OTHER INFORMATION: Reverse Primer

<400> SEQUENCE: 45
gctttcgcag tagttagtct tca                                             23

<210> SEQ ID NO 46
<211> LENGTH: 21
<212> TYPE: DNA
<213> ORGANISM: Artificial Sequence
<220> FEATURE:
<223> OTHER INFORMATION: Forward Primer

<400> SEQUENCE: 46
gcgattgatg gtgatacggt t                                               21

<210> SEQ ID NO 47
<211> LENGTH: 24
<212> TYPE: DNA
<213> ORGANISM: Artificial Sequence
<220> FEATURE:
<223> OTHER INFORMATION: Reverse Primer

<400> SEQUENCE: 47
agccaagcct tgacgaacta aagc                                            24

<210> SEQ ID NO 48
<211> LENGTH: 22
<212> TYPE: DNA
<213> ORGANISM: Artificial Sequence
<220> FEATURE:
<223> OTHER INFORMATION: Forward Primer

<400> SEQUENCE: 48
aaaatcgatg gtaaaggttg gc                                              22

<210> SEQ ID NO 49
<211> LENGTH: 22
<212> TYPE: DNA
<213> ORGANISM: Artificial Sequence
<220> FEATURE:
<223> OTHER INFORMATION: Reverse Primer

<400> SEQUENCE: 49
agttctgcac taccggattt gc                                              22

<210> SEQ ID NO 50
<211> LENGTH: 19
<212> TYPE: DNA
<213> ORGANISM: Artificial Sequence
<220> FEATURE:
<223> OTHER INFORMATION: Forward Primer
```

<400> SEQUENCE: 50
gatgatcatt agtcggtgg                                              19

<210> SEQ ID NO 51
<211> LENGTH: 18
<212> TYPE: DNA
<213> ORGANISM: Artificial Sequence
<220> FEATURE:
<223> OTHER INFORMATION: Reverse Primer

<400> SEQUENCE: 51
ctaccttagg cggtcgtc                                               18

<210> SEQ ID NO 52
<211> LENGTH: 20
<212> TYPE: DNA
<213> ORGANISM: Artificial Sequence
<220> FEATURE:
<223> OTHER INFORMATION: Forward Primer

<400> SEQUENCE: 52
gacatccttc gcaaagctat                                             20

<210> SEQ ID NO 53
<211> LENGTH: 21
<212> TYPE: DNA
<213> ORGANISM: Artificial Sequence
<220> FEATURE:
<223> OTHER INFORMATION: Reverse Primer

<400> SEQUENCE: 53
cagttaccca ggcagtatct c                                           21

<210> SEQ ID NO 54
<211> LENGTH: 18
<212> TYPE: DNA
<213> ORGANISM: Artificial Sequence
<220> FEATURE:
<223> OTHER INFORMATION: Forward Primer

<400> SEQUENCE: 54
gaacgaagcc ttttaggc                                               18

<210> SEQ ID NO 55
<211> LENGTH: 25
<212> TYPE: DNA
<213> ORGANISM: Artificial Sequence
<220> FEATURE:
<223> OTHER INFORMATION: Reverse Primer

<400> SEQUENCE: 55
gatacagcta gacgttaagc atcta                                       25

<210> SEQ ID NO 56
<211> LENGTH: 23
<212> TYPE: DNA
<213> ORGANISM: Artificial Sequence
<220> FEATURE:
<223> OTHER INFORMATION: Forward Primer

<400> SEQUENCE: 56
taacatcaat atcgcatgag aag                                         23

```
<210> SEQ ID NO 57
<211> LENGTH: 20
<212> TYPE: DNA
<213> ORGANISM: Artificial Sequence
<220> FEATURE:
<223> OTHER INFORMATION: Reverse Primer

<400> SEQUENCE: 57
cagtacagct acgcgtcatt                                              20

<210> SEQ ID NO 58
<211> LENGTH: 19
<212> TYPE: DNA
<213> ORGANISM: Artificial Sequence
<220> FEATURE:
<223> OTHER INFORMATION: Forward Primer

<400> SEQUENCE: 58
taacggctca cctaggcga                                               19

<210> SEQ ID NO 59
<211> LENGTH: 26
<212> TYPE: DNA
<213> ORGANISM: Artificial Sequence
<220> FEATURE:
<223> OTHER INFORMATION: Reverse Primer

<400> SEQUENCE: 59
gtggactacc agggtatcta atcctg                                       26

<210> SEQ ID NO 60
<211> LENGTH: 16
<212> TYPE: DNA
<213> ORGANISM: Artificial Sequence
<220> FEATURE:
<223> OTHER INFORMATION: E. Coli specific semi-nested Primer

<400> SEQUENCE: 60
gcaatattcc ccactg                                                  16

<210> SEQ ID NO 61
<211> LENGTH: 39
<212> TYPE: DNA
<213> ORGANISM: Artificial Sequence
<220> FEATURE:
<223> OTHER INFORMATION: Primer

<400> SEQUENCE: 61
gattcttgcc ttcgcgatcg caaccctcta tcacgaagg                         39

<210> SEQ ID NO 62
<211> LENGTH: 39
<212> TYPE: DNA
<213> ORGANISM: Artificial Sequence
<220> FEATURE:
<223> OTHER INFORMATION: Primer

<400> SEQUENCE: 62
ccttcgtgat agagggttgc gatcgcgaag gcaagaatc                         39

<210> SEQ ID NO 63
<211> LENGTH: 41
<212> TYPE: DNA
<213> ORGANISM: Artificial Sequence
<220> FEATURE:
<223> OTHER INFORMATION: Primer
```

-continued

<400> SEQUENCE: 63
gatgctcgcc ttcgcgatcg caacgctcta tcacgagggc g    41

<210> SEQ ID NO 64
<211> LENGTH: 41
<212> TYPE: DNA
<213> ORGANISM: Artificial Sequence
<220> FEATURE:
<223> OTHER INFORMATION: Primer

<400> SEQUENCE: 64
cgccctcgtg atagagcgtt gcgatcgcga aggcgagcat c    41

<210> SEQ ID NO 65
<211> LENGTH: 2509
<212> TYPE: DNA
<213> ORGANISM: Thermus aquaticus
<220> FEATURE:
<223> OTHER INFORMATION: Gene encoding thermal resistant DNA polymerase
      derived from Thermus aquaticus

<400> SEQUENCE: 65

| | |
|---|---|
| atgaggggga tgttgccatt gttttgaacct aaagggaggg ttttactcgt ggatggccat | 60 |
| caccttgctt atcgtacttt ccacgctctc aaaggtttaa caacctctag gggagagcca | 120 |
| gttcaagctg tgtacgggtt tgcaaagtca ctccttaaag ccttgaagga ggacggtgat | 180 |
| gccgttatcg tggtattcga tgctaaagca ccaagtttta gacacgaggc ttacggaggc | 240 |
| tataaggctg acgtgcacc aactcccgag gatttcccaa gacaactcgc cctgataaag | 300 |
| gagttggttg acctacttgg attggctagg ttagaagttc ccggttacga agctgacgac | 360 |
| gttttggcct cacttgctaa gaaagcagaa aaggagggct acgaagttcg tatactcaca | 420 |
| gccgataaag acttgtatca actgttatct gataggattc atgtgcttca ccccgaaggg | 480 |
| taccttatca cccctgcctg gctgtgggaa agtacgggc tcagacctga ccagtgggct | 540 |
| gattaccgtg cactcaccgg tgacgagagt gacaatcttc ctggcgtgaa aggaataggt | 600 |
| gaaaagacag ctagaaaatt gctagaagag tggggtccc tcgaggcact ttttgaagaac | 660 |
| cttgataggt aaaaccagc tattagagaa aagatactgg cccatatgga tgacttgaaa | 720 |
| ctatcatggg acttagctaa agtcagaacc gatttacctt tggaagtgga ttttgctaag | 780 |
| agaaggggaac cagatagaga gaggcttaga gcattcttgg agcgtctgga atttggatct | 840 |
| ttactccacg agttcggttt gcttgagtct cccaaggcac tggaagaggc accatggcct | 900 |
| ccacctgaag gcgcttttgt tgggttcgtt ctcagtagga aggaacctat gtgggcagac | 960 |
| ttgctcgccc tagcagctgc aagaggggga agagtgcata ggctcccga accttataag | 1020 |
| gcactcagag atcttaagga ggctaggggc ctcttggcaa aggacctatc cgtgcttgca | 1080 |
| ctcagggaag gattgggact cccacccggt gatgaccta gttattggc ttacttgctt | 1140 |
| gacccatcca ataccacacc cgaggagtt gcccgtaggt atgggggcga gtggactgag | 1200 |
| gaagctggtg agagggccgc attgagtgag aggctatttg ccaacttatg ggggaggttg | 1260 |
| gagggggagg aacgtctgct atggctttac agagaggtgg agcgtccctt gagtgctgta | 1320 |
| ttagctcaca tggaagctac aggcgtccgt ctagatgttg cttacttaag ggctctaagt | 1380 |
| ttggaagttg cagaagagat cgccagatta gaagctgaag ttttcaggtt agcaggacac | 1440 |
| cctttttaatc tcaatagtag ggaccaactc gaacgtgtgt tatttgatga actgggcctc | 1500 |
| cccgctatag ggaaaaccga gaaaacaggg aaaaggtcca catctgcagc tgtattggaa | 1560 |

```
gcccttagag aagcacatcc tattgtggag aaaatactac agtacaggga gctaaccaaa    1620
ttaaagagta cctacataga tccattgcct gatcttattc acccaaggac cggaaggctt    1680
cacacccgtt tcaatcaaac cgcaacagct actgggaggt tatcatcttc cgaccctaac    1740
ttgcaaaata tacctgttcg tacccactc ggacagagaa tacgtagagc tttcattgcc     1800
gaagagggat ggctcttggt tgctttggat tatagtcaga ttgaacttag agttctagca    1860
caccttagtg gcgacgaaaa cctcatcagg gtgtttcagg aggggagaga tatacacacc    1920
gaaactgctt catggatgtt tggggtgccc agggaagccg tagacccct catgagaagg     1980 gctgctaaaa caattaattt cggcgtgttg tacggaatgt ccgctcacag gctatcacaa    2040
gagttggcaa tcccctatga agaggctcaa gccttcattg agaggtattt tcagtccttt    2100
ccaaaggtgc gtgcttggat agagaaaact ttagaggaag gtagaaggag agggtatgtg    2160
gaaactctat ttggcagacg taggtacgtt cctgacctcg aagctagagt taagtccgtc    2220
agagaggcag ctgaacgtat ggcattcaat atgcctgttc aaggaacagc tgcagactta    2280
atgaaattag ctatggtgaa gttgttccca aggttagagg aaatgggtgc aagaatgctc    2340
ctacaggtcc atgatgagct agtgttggaa gcacctaaag agagggcaga ggcagtagcc    2400
aggttggcaa aggaggttat ggaagggggtg tatccacttg ctgtcccctt ggaggtggaa   2460
gtcgggatcg gtgaggactg gttatccgca aaggaatgag ctcactagt              2509

<210> SEQ ID NO 66
<211> LENGTH: 799
<212> TYPE: DNA
<213> ORGANISM: Artificial Sequence
<220> FEATURE:
<223> OTHER INFORMATION: TEF promoter

<400> SEQUENCE: 66
gcggccgcgg gtgcaaacgg tggtcaaagg atggttcaga tacaaattag caacaggcca      60
ggctagacgc gcgactatcc actgcggcaa atggtgagct gcaagcaacg gtaagatgtg     120
acaggacgag cggtgtgccg ggaaaaaaat tggaggagcg caaagcggcg gctgtccctc     180
agtggtgccc aaacgttatc gatagtacac caagcatggg cagtgagcgg ctatacagag    240
ggaataatag gcatatcggc acgactagat tcggtagaaa gcatcgaaga gcaattcatt    300
gagcatatta tcacgtggaa tgcgatagct gtggccaggt tgagacaccg caagtgaaag    360
atacacacat agattctcga ttcgagcggt ttgcctccgc caccgcagtg catagcaagc    420
aaagaaacga cagttggctc atcatccgtt acatcatttt ttctactggc tccgctcggt    480
gggctcccaa cgaagcagca aaaagtgag agaaaaaaac tagcttggcg gggcaacaga    540
agctagaccc tttggctcgc ttagtcagtg cgcccactca ctcacactca aaaggccac    600 ccctcccgca ccctcttctc atcaccgtct tcataccacg gttcgtcaag caatcgtatc    660
tggtaagctt tgacctcctc gagcgggctc cactttgcta tttcttggat ctgctctttc    720
ttttctctct acctcttttt ctaacctctc ttcagaaagt tcaaccgtac ttcactccat    780
cttcctacgt cactctaga                                                  799

<210> SEQ ID NO 67
<211> LENGTH: 230
<212> TYPE: DNA
<213> ORGANISM: Artificial Sequence
<220> FEATURE:
<223> OTHER INFORMATION: TEF promoter
```

<400> SEQUENCE: 67

```
taaagcggcg tgctctgcac ataacacgtg tcgtgtttgg gttcggtatg ggtaatggcg    60
aatggggaca tgcatttatg ggatagggggg ctgggttggt gtaatcaaat gtgcatacag   120
accagctgat acgaatacta caacttaccc cgacacacgc attcatgtga cgcccaacac   180
ctcgtctaac tcatcggggc aactcacctc aatccgattc agcctcccgg              230
```

<210> SEQ ID NO 68
<211> LENGTH: 28
<212> TYPE: DNA
<213> ORGANISM: Artificial Sequence
<220> FEATURE:
<223> OTHER INFORMATION: Primer

<400> SEQUENCE: 68

```
gcggccgcgg gtgcaaacgg tggtcaaa                                       28
```

<210> SEQ ID NO 69
<211> LENGTH: 28
<212> TYPE: DNA
<213> ORGANISM: Artificial Sequence
<220> FEATURE:
<223> OTHER INFORMATION: Primer

<400> SEQUENCE: 69

```
atatctagag tgacgtagga agatggag                                       28
```

<210> SEQ ID NO 70
<211> LENGTH: 40
<212> TYPE: DNA
<213> ORGANISM: Artificial Sequence
<220> FEATURE:
<223> OTHER INFORMATION: Primer

<400> SEQUENCE: 70

```
gtttaaacag atctcccggg taaagcggcg tgctctgcac                          40
```

<210> SEQ ID NO 71
<211> LENGTH: 26
<212> TYPE: DNA
<213> ORGANISM: Artificial Sequence
<220> FEATURE:
<223> OTHER INFORMATION: Primer

<400> SEQUENCE: 71

```
tatggtaccg ggaggctgaa tcggat                                         26
```

<210> SEQ ID NO 72
<211> LENGTH: 57
<212> TYPE: DNA
<213> ORGANISM: Artificial Sequence
<220> FEATURE:
<223> OTHER INFORMATION: Primer

<400> SEQUENCE: 72

```
atagtttaaa catgcgattat aaggatgacg atgacaagat gagaggcatg ctgccac      57
```

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
atggtaccgg gaggctgaat cggat					25

<210> SEQ ID NO 74
<400> SEQUENCE: 74

000

<210> SEQ ID NO 75
<400> SEQUENCE: 75

000

<210> SEQ ID NO 76
<400> SEQUENCE: 76

000

<210> SEQ ID NO 77
<400> SEQUENCE: 77

000

<210> SEQ ID NO 78
<400> SEQUENCE: 78

000

<210> SEQ ID NO 79
<400> SEQUENCE: 79

000

<210> SEQ ID NO 80
<211> LENGTH: 24
<212> TYPE: DNA
<213> ORGANISM: Artificial Sequence
<220> FEATURE:
<223> OTHER INFORMATION: Forward Primer

<400> SEQUENCE: 80
gattagatac cctggtagtc cacg					24

<210> SEQ ID NO 81
<211> LENGTH: 2328
<212> TYPE: DNA
<213> ORGANISM: Pyrococcus furiosus
<220> FEATURE:
<223> OTHER INFORMATION: Gene encoding thermal resistant DNA polymerase
      derived from Pyrococcus furiosus

<400> SEQUENCE: 81
atgattttag atgtggatta cataactgaa gaaggaaaac ctgttattag gctattcaaa			60 aaagagaacg gaaaatttaa gatagagcat gatagaactt ttagaccata catttacgct			120 cttctcaggg atgattcaaa gattgaagaa gttaagaaaa taacggggga aaggcatgga			180 aagattgtga gaattgttga tgtagagaag gttgagaaaa agtttctcgg caagcctatt			240 accgtgtgga aactttattt ggaacatccc caagatgttc ccactattag agaaaaagtt			300

| | |
|---|---|
| agagaacatc cagcagttgt ggacatcttc gaatacgata ttccatttgc aaagagatac | 360 |
| ctcatcgaca aaggcctaat accaatggag ggggaagaag agctaaagat tcttgccttc | 420 |
| gatatagaaa ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat ttctcaggat tatcagggag | 600 |
| aaggatcctg acattatagt tacttataat ggagactcat tcgacttccc atatttagcg | 660 |
| aaaagggcag aaaaacttgg gattaaatta accattggaa gagatggaag cgagcccaag | 720 |
| atgcagagaa taggcgatat gacggctgta gaagtcaagg gaagaataca tttcgacttg | 780 |
| tatcatgtaa taacaaggac aataaatctc ccaacataca cactagaggc tgtatatgaa | 840 |
| gcaattttg gaaagccaaa ggagaaggta tacgccgacg agatagcaaa agcctgggaa | 900 |
| agtggagaga accttgagag agttgccaaa tactcgatgg aagatgcaaa ggcaacttat | 960 |
| gaactcggga agaattcct tccaatggaa attcagcttt caagattagt tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aaagagccag aaaaggggtt gtgggaaaac | 1200 |
| atagtatacc tagattttag agccctatat ccctcgatta taattaccca caatgtttct | 1260 |
| cccgatactc taaatcttga gggatgcaag aactatgata tcgctcctca agtaggccac | 1320 |
| aagttctgca aggacatccc tggttttata ccaagtctct tgggacattt gttagaggaa | 1380 |
| agacaaaaga ttaagacaaa aatgaaggaa actcaagatc ctatagaaaa aatactcctt | 1440 |
| gactatagac aaaaagcgat aaaactctta gcaaattctt tctacggata ttatggctat | 1500 |
| gcaaaagcaa gatggtactg taaggagtgt gctgagagcg ttactgcctg gggaagaaag | 1560 |
| tacatcgagt tagtatggaa ggagctcgaa gaaaagtttg gatttaaagt cctctacatt | 1620 |
| gacactgatg gtctctatgc aactatccca ggaggagaaa gtgaggaaat aaagaaaaag | 1680 |
| gctctagaat ttgtaaaata cataaattca aagctccctg gactgctaga gcttgaatat | 1740 |
| gaagggtttt ataagagggg attcttcgtt acgaagaaga ggtatgcagt aatagatgaa | 1800 |
| gaaggaaaag tcattactcg tggtttagag atagttagga gagattggag tgaaattgca | 1860 |
| aaagaaactc aagctagagt tttggagaca atactaaaac acggagatgt tgaagaagct | 1920 |
| gtgagaatag taaagaagt aatacaaaag cttgccaatt atgaaattcc accagagaag | 1980 |
| ctcgcaatat atgagcagat aacaagacca ttacatgagt ataaggcgat aggtcctcac | 2040 |
| gtagctgttg caaagaaact agctgctaaa ggagttaaaa taaagccagg aatggtaatt | 2100 |
| ggatacatag tacttagagg cgatggtcca attagcaata gggcaattct agctgaggaa | 2160 |
| tacgatccca aaaagcacaa gtatgacgca gaatattaca ttgagaacca ggttcttcca | 2220 |
| gcggtactta ggatattgga gggatttgga tacagaaagg aagacctcag ataccaaaag | 2280 |
| acaagacaag tcggcctaac ttcctggctt aacattaaaa aatcctag | 2328 |

<210> SEQ ID NO 82
<211> LENGTH: 2322
<212> TYPE: DNA
<213> ORGANISM: Thermococcus gorgonarius
<220> FEATURE:
<221> NAME/KEY: misc_feature
<222> LOCATION: (277)..(279)
<223> OTHER INFORMATION: n can be any
      Thermococcus gorgonarius

```
<400> SEQUENCE: 82
atgatcctcg atacagacta cataactgag gatggaaagc ccgtcatcag gatcttcaag      60
aaggagaacg gcgagttcaa aatagactac gacagaaact ttgagccata catctacgcg     120
ctcttgaagg acgactctgc gattgaggac gtcaagaaga taactgccga gaggcacggc     180
actaccgtta gggttgtcag ggccgagaaa gtgaagaaga agttcctagg caggccgata     240
gaggtctgga agctctactt cactcaccc caggacnnnc ccgcaatcag ggacaagata     300
aaggagcatc ctgccgttgt ggacatctac gagtacgaca tcccccttcgc gaagcgctac     360 ctcatagaca aaggcttaat cccgatggag ggcgacgagg aacttaagat gctcgccttc     420
gacatcgaga cgctctatca cgagggcgag gagttcgccg aagggcctat cctgatgata     480
agctacgccg acgaggaagg ggcgcgcgtt attacctgga agaatatcga ccttccctat     540
gtcgacgtcg tttccaccga aaggagatg ataaagcgct tcctcaaggt cgtcaaggaa     600
aaggatcccg acgtcctcat aacctacaac ggcgacaact tcgacttcgc ctacctcaag     660
aagcgctccg agaagctcgg agtcaagttc atcctcggaa gggaagggag cgagccgaaa     720
atccagcgca tgggcgatcg ctttgcggtg gaggtcaagg gaaggattca cttcgacctc     780
taccccgtca ttaggagaac gattaacctc cccacttaca cccttgaggc agtatatgaa     840 gccatcttg acagccgaa ggagaaggtc tacgctgagg agatagcgca ggcctgggaa     900
acgggcgagg gattagaaag ggtggcccgc tactcgatgg aggacgcaaa ggtaacctat     960
gaactcggaa aagagttctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca acagggaggg ttgtgaggag tacgacgtgg ctcctcaggt aggccataag    1320
ttctgcaagg acttccccgg cttcatccca agcctcctcg gagacctctt ggaggagaga    1380
cagaaggtaa agaagaagat gaaggccact atagacccaa tcgagaagaa actcctcgat    1440
tacaggcaac gagcaatcaa aatccttgct aatagcttct acggttacta cggctatgca    1500
aaggcccgct ggtactgcaa ggagtgcgcc gagagcgtta ccgcttgggg caggcagtac    1560
atcgagacca cgataaggga aatagaggag aaatttggct ttaaagtcct ctacgcggac    1620
acagatggat ttttcgcaac aatacctgga gcggacgccg aaaccgtcaa aaagaaggca    1680
aaggagttcc tggactacat caacgccaaa ctgcccggcc tgctcgaact cgaatacgag    1740
ggcttctaca gcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaagggg ataaaaatcc ggcccggaac ggtcataagc    2100
tacatcgtgc tcaaaggctc gggaaggatt ggggacaggg ctatacccctt tgacgaattt    2160 gacccccgcaa agcacaagta cgatgcagaa tactacatcg agaaccaggt tcttccagct    2220
gtggagagga ttctgagggc ctttggttac cgtaaagaag attaaggta tcagaaaacg    2280 cggcaggttg gcttgggggc gtggctaaaa cctaagacat ga                       2322
```

-continued

```
<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
gatgagttcg tgtccgtaca act                                              23

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
ggttatcgaa atcagccaca gcgcc                                            25

<210> SEQ ID NO 85
<211> LENGTH: 15
<212> TYPE: DNA
<213> ORGANISM: Artificial Sequence
<220> FEATURE:
<223> OTHER INFORMATION: Primer

<400> SEQUENCE: 85
agcagccgcg gtaat                                                       15

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
ggactaccag ggtatctaat cct                                              23

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
cccgaattca tgagggggat gttgccattg                                       30

<210> SEQ ID NO 88
<211> LENGTH: 30
<212> TYPE: DNA
<213> ORGANISM: Artificial Sequence
<220> FEATURE:
<223> OTHER INFORMATION: Primer

<400> SEQUENCE: 88
aaagcggccg ctcattcctt tgcggataac                                       30

<210> SEQ ID NO 89
<211> LENGTH: 30
<212> TYPE: DNA
<213> ORGANISM: Artificial Sequence
<220> FEATURE:
<223> OTHER INFORMATION: Primer
```

-continued

<400> SEQUENCE: 89
gggggtacca tgattttaga tgtggattac　　　　　　　　　　　　　　　　　30

<210> SEQ ID NO 90
<211> LENGTH: 27
<212> TYPE: DNA
<213> ORGANISM: Artificial Sequence
<220> FEATURE:
<223> OTHER INFORMATION: Primer

<400> SEQUENCE: 90
cccgcggccg cctaggattt tttaatg　　　　　　　　　　　　　　　　　　27

<210> SEQ ID NO 91
<211> LENGTH: 27
<212> TYPE: DNA
<213> ORGANISM: Artificial Sequence
<220> FEATURE:
<223> OTHER INFORMATION: Primer

<400> SEQUENCE: 91
gggggtacca tgatcctcga tacagac　　　　　　　　　　　　　　　　　　27

<210> SEQ ID NO 92
<211> LENGTH: 29
<212> TYPE: DNA
<213> ORGANISM: Artificial Sequence
<220> FEATURE:
<223> OTHER INFORMATION: Primer

<400> SEQUENCE: 92
cccgcggccg ctcatgtctt aggttttag　　　　　　　　　　　　　　　　　29

<210> SEQ ID NO 93
<211> LENGTH: 832
<212> TYPE: PRT
<213> ORGANISM: Thermus aquaticus
<220> FEATURE:
<223> OTHER INFORMATION: Amino acid sequence for thermal resistant DNA
      polymerase derived from Thermus aquaticus

<400> SEQUENCE: 93

Met Arg Gly Met Leu Pro Leu Phe Glu Pro Lys Gly Arg Val Leu
1               5                   10                  15

Leu Val Asp Gly His His Leu Ala Tyr Arg Thr Phe His Ala Leu
                20                  25                  30

Lys Gly Leu Thr Thr Ser Arg Gly Glu Pro Val Gln Ala Val Tyr
                35                  40                  45

Gly Phe Ala Lys Ser Leu Leu Lys Ala Leu Lys Glu Asp Gly Asp
                50                  55                  60

Ala Val Ile Val Val Phe Asp Ala Lys Ala Pro Ser Phe Arg His
                65                  70                  75

Glu Ala Tyr Gly Gly Tyr Lys Ala Gly Arg Ala Pro Thr Pro Glu
                80                  85                  90

Asp Phe Pro Arg Gln Leu Ala Leu Ile Lys Glu Leu Val Asp Leu
                95                  100                 105

Leu Gly Leu Ala Arg Leu Glu Val Pro Gly Tyr Glu Ala Asp Asp
                110                 115                 120

Val Leu Ala Ser Leu Ala Lys Lys Ala Glu Lys Glu Gly Tyr Glu
                125                 130                 135

```
Val Arg Ile Leu Thr Ala Asp Lys Asp Leu Tyr Gln Leu Leu Ser
            140                 145                 150

Asp Arg Ile His Val Leu His Pro Glu Gly Tyr Leu Ile Thr Pro
            155                 160                 165

Ala Trp Leu Trp Glu Lys Tyr Gly Leu Arg Pro Asp Gln Trp Ala
            170                 175                 180

Asp Tyr Arg Ala Leu Thr Gly Asp Glu Ser Asp Asn Leu Pro Gly
            185                 190                 195

Val Lys Gly Ile Gly Glu Lys Thr Ala Arg Lys Leu Leu Glu Glu
            200                 205                 210

Trp Gly Ser Leu Glu Ala Leu Leu Lys Asn Leu Asp Arg Leu Lys
            215                 220                 225

Pro Ala Ile Arg Glu Lys Ile Leu Ala His Met Asp Asp Leu Lys
            230                 235                 240

Leu Ser Trp Asp Leu Ala Lys Val Arg Thr Asp Leu Pro Leu Glu
            245                 250                 255

Val Asp Phe Ala Lys Arg Arg Glu Pro Asp Arg Glu Arg Leu Arg
            260                 265                 270

Ala Phe Leu Glu Arg Leu Glu Phe Gly Ser Leu Leu His Glu Phe
            275                 280                 285

Gly Leu Leu Glu Ser Pro Lys Ala Leu Glu Glu Ala Pro Trp Pro
            290                 295                 300

Pro Pro Glu Gly Ala Phe Val Gly Phe Val Leu Ser Arg Lys Glu
            305                 310                 315

Pro Met Trp Ala Asp Leu Leu Ala Leu Ala Ala Ala Arg Gly Gly
            320                 325                 330

Arg Val His Arg Ala Pro Glu Pro Tyr Lys Ala Leu Arg Asp Leu
            335                 340                 345

Lys Glu Ala Arg Gly Leu Leu Ala Lys Asp Leu Ser Val Leu Ala
            350                 355                 360

Leu Arg Glu Gly Leu Gly Leu Pro Pro Gly Asp Asp Pro Met Leu
            365                 370                 375

Leu Ala Tyr Leu Leu Asp Pro Ser Asn Thr Thr Pro Glu Gly Val
            380                 385                 390

Ala Arg Arg Tyr Gly Gly Glu Trp Thr Glu Glu Ala Gly Glu Arg
            395                 400                 405

Ala Ala Leu Ser Glu Arg Leu Phe Ala Asn Leu Trp Gly Arg Leu
            410                 415                 420

Glu Gly Glu Glu Arg Leu Leu Trp Leu Tyr Arg Glu Val Glu Arg
            425                 430                 435

Pro Leu Ser Ala Val Leu Ala His Met Glu Ala Thr Gly Val Arg
            440                 445                 450

Leu Asp Val Ala Tyr Leu Arg Ala Leu Ser Leu Glu Val Ala Glu
            455                 460                 465

Glu Ile Ala Arg Leu Glu Ala Glu Val Phe Arg Leu Ala Gly His
            470                 475                 480

Pro Phe Asn Leu Asn Ser Arg Asp Gln Leu Glu Arg Val Leu Phe
            485                 490                 495

Asp Glu Leu Gly Leu Pro Ala Ile Gly Lys Thr Glu Lys Thr Gly
            500                 505                 510
```

```
Lys Arg Ser Thr Ser Ala Ala Val Leu Glu Ala Leu Arg Glu Ala
            515                 520                 525

His Pro Ile Val Glu Lys Ile Leu Gln Tyr Arg Glu Leu Thr Lys
        530                 535                 540

Leu Lys Ser Thr Tyr Ile Asp Pro Leu Pro Asp Leu Ile His Pro
    545                 550                 555

Arg Thr Gly Arg Leu His Thr Arg Phe Asn Gln Thr Ala Thr Ala
560                 565                 570

Thr Gly Arg Leu Ser Ser Ser Asp Pro Asn Leu Gln Asn Ile Pro
            575                 580                 585

Val Arg Thr Pro Leu Gly Gln Arg Ile Arg Arg Ala Phe Ile Ala
        590                 595                 600

Glu Glu Gly Trp Leu Leu Val Ala Leu Asp Tyr Ser Gln Ile Glu
    605                 610                 615

Leu Arg Val Leu Ala His Leu Ser Gly Asp Glu Asn Leu Ile Arg
620                 625                 630

Val Phe Gln Glu Gly Arg Asp Ile His Thr Glu Thr Ala Ser Trp
            635                 640                 645

Met Phe Gly Val Pro Arg Glu Ala Val Asp Pro Leu Met Arg Arg
        650                 655                 660

Ala Ala Lys Thr Ile Asn Phe Gly Val Leu Tyr Gly Met Ser Ala
    665                 670                 675

His Arg Leu Ser Gln Glu Leu Ala Ile Pro Tyr Glu Glu Ala Gln
680                 685                 690

Ala Phe Ile Glu Arg Tyr Phe Gln Ser Phe Pro Lys Val Arg Ala
            695                 700                 705

Trp Ile Glu Lys Thr Leu Glu Glu Gly Arg Arg Arg Gly Tyr Val
        710                 715                 720

Glu Thr Leu Phe Gly Arg Arg Arg Tyr Val Pro Asp Leu Glu Ala
    725                 730                 735

Arg Val Lys Ser Val Arg Glu Ala Ala Glu Arg Met Ala Phe Asn
740                 745                 750

Met Pro Val Gln Gly Thr Ala Ala Asp Leu Met Lys Leu Ala Met
            755                 760                 765

Val Lys Leu Phe Pro Arg Leu Glu Glu Met Gly Ala Arg Met Leu
        770                 775                 780

Leu Gln Val His Asp Glu Leu Val Leu Glu Ala Pro Lys Glu Arg
    785                 790                 795

Ala Glu Ala Val Ala Arg Leu Ala Lys Glu Val Met Glu Gly Val
800                 805                 810

Tyr Pro Leu Ala Val Pro Leu Glu Val Glu Val Gly Ile Gly Glu
            815                 820                 825

Asp Trp Leu Ser Ala Lys Glu
                830

<210> SEQ ID NO 94
<211> LENGTH: 775
<212> TYPE: PRT
<213> ORGANISM: Pyrococcus furiosus
<220> FEATURE:
<223> OTHER INFORMATION: Amino acid sequence for thermal resistant DNA
      polymerase derived from Pyrococcus furiosus
```

```
<400> SEQUENCE: 94

Met Ile Leu Asp Val Asp Tyr Ile Thr Glu Glu Gly Lys Pro Val
1               5                  10                  15

Ile Arg Leu Phe Lys Lys Glu Asn Gly Lys Phe Lys Ile Glu His
                20                  25                  30

Asp Arg Thr Phe Arg Pro Tyr Ile Tyr Ala Leu Leu Arg Asp Asp
                35                  40                  45

Ser Lys Ile Glu Glu Val Lys Lys Ile Thr Gly Glu Arg His Gly
                50                  55                  60

Lys Ile Val Arg Ile Val Asp Val Glu Lys Val Glu Lys Lys Phe
                65                  70                  75

Leu Gly Lys Pro Ile Thr Val Trp Lys Leu Tyr Leu Glu His Pro
                80                  85                  90

Gln Asp Val Pro Thr Ile Arg Glu Lys Val Arg Glu His Pro Ala
                95                  100                 105

Val Val Asp Ile Phe Glu Tyr Asp Ile Pro Phe Ala Lys Arg Tyr
                110                 115                 120

Leu Ile Asp Lys Gly Leu Ile Pro Met Glu Gly Glu Glu Glu Leu
                125                 130                 135

Lys Ile Leu Ala Phe Asp Ile Glu Thr Leu Tyr His Glu Gly Glu
                140                 145                 150

Glu Phe Gly Lys Gly Pro Ile Ile Met Ile Ser Tyr Ala Asp Glu
                155                 160                 165

Asn Glu Ala Lys Val Ile Thr Trp Lys Asn Ile Asp Leu Pro Tyr
                170                 175                 180

Val Glu Val Val Ser Ser Glu Arg Glu Met Ile Lys Arg Phe Leu
                185                 190                 195

Arg Ile Ile Arg Glu Lys Asp Pro Asp Ile Ile Val Thr Tyr Asn
                200                 205                 210

Gly Asp Ser Phe Asp Phe Pro Tyr Leu Ala Lys Arg Ala Glu Lys
                215                 220                 225

Leu Gly Ile Lys Leu Thr Ile Gly Arg Asp Gly Ser Glu Pro Lys
                230                 235                 240

Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu
                260                 265                 270

Pro Thr Tyr Thr Leu Glu Ala Val Tyr Glu Ala Ile Phe Gly Lys
                275                 280                 285

Pro Lys Glu Lys Val Tyr Ala Asp Glu Ile Ala Lys Ala Trp Glu
                290                 295                 300

Ser Gly Glu Asn Leu Glu Arg Val Ala Lys Tyr Ser Met Glu Asp
                305                 310                 315

Ala Lys Ala Thr Tyr Glu Leu Gly Lys Glu Phe Leu Pro Met Glu
                320                 325                 330

Ile Gln Leu Ser Arg Leu Val Gly Gln Pro Leu Trp Asp Val Ser
                335                 340                 345

Arg Ser Ser Thr Gly Asn Leu Val Glu Trp Phe Leu Leu Arg Lys
                350                 355                 360

Ala Tyr Glu Arg Asn Glu Val Ala Pro Asn Lys Pro Ser Glu Glu
                365                 370                 375

Glu Tyr Gln Arg Arg Leu Arg Glu Ser Tyr Thr Gly Gly Phe Val
                380                 385                 390
```

```
Lys Glu Pro Glu Lys Gly Leu Trp Glu Asn Ile Val Tyr Leu Asp
            395                 400                 405
Phe Arg Ala Leu Tyr Pro Ser Ile Ile Ile Thr His Asn Val Ser
            410                 415                 420
Pro Asp Thr Leu Asn Leu Glu Gly Cys Lys Asn Tyr Asp Ile Ala
            425                 430                 435
Pro Gln Val Gly His Lys Phe Cys Lys Asp Ile Pro Gly Phe Ile
            440                 445                 450
Pro Ser Leu Leu Gly His Leu Leu Glu Glu Arg Gln Lys Ile Lys
            455                 460                 465
Thr Lys Met Lys Glu Thr Gln Asp Pro Ile Glu Lys Ile Leu Leu
            470                 475                 480
Asp Tyr Arg Gln Lys Ala Ile Lys Leu Leu Ala Asn Ser Phe Tyr
            485                 490                 495
Gly Tyr Tyr Gly Tyr Ala Lys Ala Arg Trp Tyr Cys Lys Glu Cys
            500                 505                 510
Ala Glu Ser Val Thr Ala Trp Gly Arg Lys Tyr Ile Glu Leu Val
            515                 520                 525
Trp Lys Glu Leu Glu Glu Lys Phe Gly Phe Lys Val Leu Tyr Ile
            530                 535                 540
Asp Thr Asp Gly Leu Tyr Ala Thr Ile Pro Gly Gly Glu Ser Glu
            545                 550                 555
Glu Ile Lys Lys Lys Ala Leu Glu Phe Val Lys Tyr Ile Asn Ser
            560                 565                 570
Lys Leu Pro Gly Leu Leu Glu Leu Glu Tyr Glu Gly Phe Tyr Lys
            575                 580                 585
Arg Gly Phe Phe Val Thr Lys Lys Arg Tyr Ala Val Ile Asp Glu
            590                 595                 600
Glu Gly Lys Val Ile Thr Arg Gly Leu Glu Ile Val Arg Arg Asp
            605                 610                 615
Trp Ser Glu Ile Ala Lys Glu Thr Gln Ala Arg Val Leu Glu Thr
            620                 625                 630
Ile Leu Lys His Gly Asp Val Glu Glu Ala Val Arg Ile Val Lys
            635                 640                 645
Glu Val Ile Gln Lys Leu Ala Asn Tyr Glu Ile Pro Pro Glu Lys
            650                 655                 660
Leu Ala Ile Tyr Glu Gln Ile Thr Arg Pro Leu His Glu Tyr Lys
            665                 670                 675
Ala Ile Gly Pro His Val Ala Val Ala Lys Lys Leu Ala Ala Lys
            680                 685                 690
Gly Val Lys Ile Lys Pro Gly Met Val Ile Gly Tyr Ile Val Leu
            695                 700                 705
Arg Gly Asp Gly Pro Ile Ser Asn Arg Ala Ile Leu Ala Glu Glu
            710                 715                 720
Tyr Asp Pro Lys Lys His Lys Tyr Asp Ala Glu Tyr Tyr Ile Glu
            725                 730                 735
Asn Gln Val Leu Pro Ala Val Leu Arg Ile Leu Glu Gly Phe Gly
            740                 745                 750
Tyr Arg Lys Glu Asp Leu Arg Tyr Gln Lys Thr Arg Gln Val Gly
            755                 760                 765
Leu Thr Ser Trp Leu Asn Ile Lys Lys Ser
            770                 775
```

```
<210> SEQ ID NO 95
<211> LENGTH: 773
<212> TYPE: PRT
<213> ORGANISM: Thermococcus gorgonarius
<220> FEATURE:
<223> OTHER INFORMATION: Amino acid sequence for thermal resistant DNA
      polymerase derived from Thermococcus gorgonarius

<400> SEQUENCE: 95

Met Ile Leu Asp Thr Asp Tyr Ile Thr Glu Asp Gly Lys Pro Val
1               5                   10                  15

Ile Arg Ile Phe Lys Lys Glu Asn Gly Glu Phe Lys Ile Asp Tyr
                20                  25                  30

Asp Arg Asn Phe Glu Pro Tyr Ile Tyr Ala Leu Leu Lys Asp Asp
                35                  40                  45

Ser Ala Ile Glu Asp Val Lys Lys Ile Thr Ala Glu Arg His Gly
                50                  55                  60

Thr Thr Val Arg Val Val Arg Ala Glu Lys Val Lys Lys Lys Phe
                65                  70                  75

Leu Gly Arg Pro Ile Glu Val Trp Lys Leu Tyr Phe Thr His Pro
                80                  85                  90

Gln Asp Val Pro Ala Ile Arg Asp Lys Ile Lys Glu His Pro Ala
                95                  100                 105

Val Val Asp Ile Tyr Glu Tyr Asp Ile Pro Phe Ala Lys Arg Tyr
                110                 115                 120

Leu Ile Asp Lys Gly Leu Ile Pro Met Glu Gly Asp Glu Glu Leu
                125                 130                 135

Lys Met Leu Ala Phe Asp Ile Glu Thr Leu Tyr His Glu Gly Glu
                140                 145                 150

Glu Phe Ala Glu Gly Pro Ile Leu Met Ile Ser Tyr Ala Asp Glu
                155                 160                 165

Glu Gly Ala Arg Val Ile Thr Trp Lys Asn Ile Asp Leu Pro Tyr
                170                 175                 180

Val Asp Val Val Ser Thr Glu Lys Glu Met Ile Lys Arg Phe Leu
                185                 190                 195

Lys Val Val Lys Glu Lys Asp Pro Asp Val Leu Ile Thr Tyr Asn
                200                 205                 210

Gly Asp Asn Phe Asp Phe Ala Tyr Leu Lys Lys Arg Ser Glu Lys
                215                 220                 225

Leu Gly Val Lys Phe Ile Leu Gly Arg Glu Gly Ser Glu Pro Lys
                230                 235                 240

Ile Gln Arg Met Gly Asp Arg Phe Ala Val Glu Val Lys Gly Arg
                245                 250                 255

Ile His Phe Asp Leu Tyr Pro Val Ile Arg Arg Thr Ile Asn Leu
                260                 265                 270

Pro Thr Tyr Thr Leu Glu Ala Val Tyr Glu Ala Ile Phe Gly Gln
                275                 280                 285

Pro Lys Glu Lys Val Tyr Ala Glu Ile Ala Gln Ala Trp Glu
                290                 295                 300

Thr Gly Glu Gly Leu Glu Arg Val Ala Arg Tyr Ser Met Glu Asp
                305                 310                 315

Ala Lys Val Thr Tyr Glu Leu Gly Lys Glu Phe Phe Pro Met Glu
                320                 325                 330

Ala Gln Leu Ser Arg Leu Val Gly Gln Ser Leu Trp Asp Val Ser
                335                 340                 345
```

-continued

```
Arg Ser Ser Thr Gly Asn Leu Val Glu Trp Phe Leu Leu Arg Lys
            350                 355                 360
Ala Tyr Glu Arg Asn Glu Leu Ala Pro Asn Lys Pro Asp Glu Arg
            365                 370                 375
Glu Leu Ala Arg Arg Glu Ser Tyr Ala Gly Gly Tyr Val Lys
            380                 385                 390
Glu Pro Glu Arg Gly Leu Trp Glu Asn Ile Val Tyr Leu Asp Phe
            395                 400                 405
Arg Ser Leu Tyr Pro Ser Ile Ile Ile Thr His Asn Val Ser Pro
            410                 415                 420
Asp Thr Leu Asn Arg Glu Gly Cys Glu Glu Tyr Asp Val Ala Pro
            425                 430                 435
Gln Val Gly His Lys Phe Cys Lys Asp Phe Pro Gly Phe Ile Pro
            440                 445                 450
Ser Leu Leu Gly Asp Leu Leu Glu Glu Arg Gln Lys Val Lys Lys
            455                 460                 465
Lys Met Lys Ala Thr Ile Asp Pro Ile Glu Lys Lys Leu Leu Asp
            470                 475                 480
Tyr Arg Gln Arg Ala Ile Lys Ile Leu Ala Asn Ser Phe Tyr Gly
            485                 490                 495
Tyr Tyr Gly Tyr Ala Lys Ala Arg Trp Tyr Cys Lys Glu Cys Ala
            500                 505                 510
Glu Ser Val Thr Ala Trp Gly Arg Gln Tyr Ile Glu Thr Thr Ile
            515                 520                 525
Arg Glu Ile Glu Glu Lys Phe Gly Phe Lys Val Leu Tyr Ala Asp
            530                 535                 540
Thr Asp Gly Phe Phe Ala Thr Ile Pro Gly Ala Asp Ala Glu Thr
            545                 550                 555
Val Lys Lys Lys Ala Lys Glu Phe Leu Asp Tyr Ile Asn Ala Lys
            560                 565                 570
Leu Pro Gly Leu Leu Glu Leu Glu Tyr Glu Gly Phe Tyr Lys Arg
            575                 580                 585
Gly Phe Phe Val Thr Lys Lys Lys Tyr Ala Val Ile Asp Glu Glu
            590                 595                 600
Asp Lys Ile Thr Thr Arg Gly Leu Glu Ile Val Arg Arg Asp Trp
            605                 610                 615
Ser Glu Ile Ala Lys Glu Thr Gln Ala Arg Val Leu Glu Ala Ile
            620                 625                 630
Leu Lys His Gly Asp Val Glu Glu Ala Val Arg Ile Val Lys Glu
            635                 640                 645
Val Thr Glu Lys Leu Ser Lys Tyr Glu Val Pro Pro Glu Lys Leu
            650                 655                 660
Val Ile Tyr Glu Gln Ile Thr Arg Asp Leu Lys Asp Tyr Lys Ala
            665                 670                 675
Thr Gly Pro His Val Ala Val Ala Lys Arg Leu Ala Ala Arg Gly
            680                 685                 690
Ile Lys Ile Arg Pro Gly Thr Val Ile Ser Tyr Ile Val Leu Lys
            695                 700                 705
Gly Ser Gly Arg Ile Gly Asp Arg Ala Ile Pro Phe Asp Glu Phe
            710                 715                 720
Asp Pro Ala Lys His Lys Tyr Asp Ala Glu Tyr Tyr Ile Glu Asn
            725                 730                 735
```

```
Gln Val Leu Pro Ala Val Glu Arg Ile Leu Arg Ala Phe Gly Tyr
            740                 745                 750

Arg Lys Glu Asp Leu Arg Tyr Gln Lys Thr Arg Gln Val Gly Leu
            755                 760                 765

Gly Ala Trp Leu Lys Pro Lys Thr
            770
```